(12) United States Patent
Macheda et al.

(10) Patent No.: US 9,862,776 B2
(45) Date of Patent: Jan. 9, 2018

(54) ANTIBODIES AGAINST HUMAN RYK AND USES THEREFOR

(71) Applicant: Peter MacCallum Cancer Institute, East Melbourne (AU)

(72) Inventors: Maria Luisa Macheda, St. Albans (AU); Michael Maurice Halford, Kangaroo Ground (AU); Steven Stacker, North Balwyn (AU); Clare Louise Parish, Thornbury (AU); Edouard Collins Nice, Docklands (AU)

(73) Assignee: Peter MacCallum Cancer Institute, East Melbourne (AU)

( * ) Notice: Subject to any disclaimer, the term of this patent is extended or adjusted under 35 U.S.C. 154(b) by 0 days.

(21) Appl. No.: 14/781,195

(22) PCT Filed: Apr. 2, 2014

(86) PCT No.: PCT/AU2014/000353
§ 371 (c)(1),
(2) Date: Sep. 29, 2015

(87) PCT Pub. No.: WO2014/161037
PCT Pub. Date: Oct. 9, 2014

(65) Prior Publication Data
US 2016/0053022 A1 Feb. 25, 2016

(30) Foreign Application Priority Data
Apr. 3, 2013 (AU) ................................ 2013901150

(51) Int. Cl.
*C07K 16/28* (2006.01)
*C07K 16/40* (2006.01)
*G01N 33/574* (2006.01)

(52) U.S. Cl.
CPC .......... *C07K 16/40* (2013.01); *C07K 16/2863* (2013.01); *G01N 33/57492* (2013.01); *C07K 2317/14* (2013.01); *C07K 2317/21* (2013.01); *C07K 2317/34* (2013.01); *C07K 2317/51* (2013.01); *C07K 2317/515* (2013.01); *C07K 2317/565* (2013.01); *C07K 2317/622* (2013.01); *C07K 2317/76* (2013.01); *C07K 2317/92* (2013.01)

(58) Field of Classification Search
CPC .......... G01N 33/57492; C07K 16/2863; C07K 2317/51; C07K 2317/515; C07K 2317/565; C07K 2317/622; C07K 2317/76; C07K 2317/21; C07K 2317/92
See application file for complete search history.

(56) References Cited

U.S. PATENT DOCUMENTS 9,040,669 B2 * 5/2015 Cheung ................ C07K 16/085
530/387.3

FOREIGN PATENT DOCUMENTS

WO WO 2005/040347 5/2005

OTHER PUBLICATIONS

Casset et al. ((2003) BBRC 307, 198-205).*
De Pascalis et al. The Journal of Immunology (2002) 169, 3076-3084.*
Lamminmaki et al. (JBC 2001,276:36687-36694).*
Ward et al. (Nature 341:544-546 (1989)).*
Brummell et al. (Biochemistry 32:1180-1187 (1993)).*
Jang et al. (Molec. Immunol. 35:1207-1217 (1998)).*
Colman (Research in Immunol. 145:33-36 (1994)).*
Smith-Gill et al. (J. Immunol. 139:4135-4144 (1987)).*
Liu, et al., "Repulsive Wnt Signaling Inhibits Axon Regeneration after CNS Injury", J. Neurosci. Aug. 13, 2008, (28):8376-8382.

* cited by examiner

*Primary Examiner* — Daniel C Gamett
(74) *Attorney, Agent, or Firm* — Cesari and McKenna, LLP

(57) ABSTRACT

The present invention relates to antibodies and antigen-binding fragments thereof that bind RYK, in particular human RYK and their use in regulating RYK-associated activities. Specifically there is provided an isolated monoclonal antibody or antigen-binding fragment or derivative thereof that specifically binds to the extracellular domain of human RYK, in particular, the antibody or antigen-binding fragment thereof, binds specifically to the WIF domain of human RYK. Preferably, the antibodies of the present invention modulate RYK-associated activity, which includes RYK mediated signal transduction activity and modulation of the interaction of Wnts with RYK and, preferably, modulate Wnt induced signaling. In particular, the antibodies inhibit the binding of Wnt5a and inhibit Wnt induced phosphorylation of Dishevelled (Dvl) 2 and/or Dvl3 proteins.

2 Claims, 21 Drawing Sheets

FIGURE 7

Homo sapiens receptor-like tyrosine kinase (RYK), transcript variant 1: (SEQ ID NO: 41)

```
   1 cggctcgggg ctgtgagcgg ctcggggccg ggggtgggcg gcggtgcggc gggcggccga
  61 cgctcctctt cggcggcggc ggcggcggcc atgcgtgggg cggcgcggct ggggcggccg
 121 ggccggagtt gcctcccggg ggccgcggc ctgagggccc cgccgccgcc gccgctgctg
 181 cttctgcttg cgctgttgcc gctgctgccc gcgcctggcg ctgccgccgc cccgccccg
 241 cggccccgg agctgcagtc ggcttccgcg gggcccagcg tgagtctcta cctgagcgag
 301 gacgaggtgc gccggctgat cggtcttgat gcagaacttt attatgtgag aaatgacctt
 361 attagtcact acgctctatc ctttagtctg ttagtaccca gtgagacaaa tttcctgcac
 421 ttcacctggc atgcgaagtc caaggttgaa tataagctgg gattccaagt ggacaatgtt
 481 ttggcaatgg atatgcccca ggtcaacatt tctgttcagg gggaagttcc acgcacttta
 541 tcagtgtttc gggtagagct ttcctgtact ggcaaagtag attctgaagt tatgatacta
 601 atgcagctca acttgacagt aaattcttca aaaaatttta ccgtcttaaa tttttaaacga
 661 aggaaaatgt gctacaaaaa acttgaagaa gtaaaaactt cagccttgga caaaaacact
 721 agcagaacta tttatgatcc tgtacatgca gctccaacca ctctacgcg tgtgttttat
 781 attagtgtag gggtttgttg tgcagtaata tttctcgtag caataatatt agctgtttg
 841 caccttcata gtatgaaaag gattgaactg gatgacagca ttagtgccag cagtagttcc
 901 caagggctgt ctcagccatc cacccagacg actcagtatc tgagagcaga cacgcccaac
 961 aatgcaactc ctatcaccag ctcctaggt tatcctacct tgcggataga gaagaacgac
1021 ttgagaagtg tcactctttt ggaggccaaa ggcaaggtga aggatatagc aatatccaga
1081 gagaggataa ctctaaaaga tgtactccaa gaaggtactt ttgggcgtat tttccatggg
1141 attttaatag atgaaaaaga tccaaataaa gaaaaacaag catttgtcaa aacagttaaa
1201 gatcaagctt ctgaaattca ggtgacaatg atgctcactg aaagttgtaa gctgcgaggt
1261 cttcatcaca gaaatcttct tcctattact catgtgtgta tagaagaagg agaaaagccc
1321 atggtgatat tgccttacat gaattggggg aatcttaaat tgttttacg acagtgcaag
1381 ttagtagagg ccaataatcc acaggcaatt tctcagcaag acctggtaca catggctatt
1441 cagattgcct gtggaatgag ctacctggcc agaagggaag tcatccacaa agacctggct
1501 gccaggaact gtgtcattga tgacacactt caagttaaga tcacagacaa tgccctctcc
1561 agagacttgt tccccatgga ctatcactgt ctggggggaca atgaaaacag gccagttcgt
1621 tggatggctc ttgaaagtct ggttaataac gagttctcta gcgctagtga tgtgtgggcc
1681 tttggagtga cgctgtggga actcatgact ctgggccaga ctccctacgt ggacattgac
1741 cccttcgaga tggccgcata cctgaaagat ggttaccgaa tagcccagcc aatcaactgt
1801 cctgatgaat tatttgctgt gatggcctgt tgctgggcct tagatccaga ggagaggccc
1861 aagtttcagc agctggtaca gtgcctaaca gagtttcatg cagccctggg ggcctacgtc
1921 tgactcctct ccaatcccac accatcagga agaaggtgcc tgtcgggcct cacttgaagc
1981 ctgtcaggga tgcttgtat ctaacacaac gccaacagaa gcacatttgt cttccagaac
2041 accgtgcctt agaaatgctt tagaatctga acttttttaag acagacttaa taatgtggca
2101 tattttctag atatcacttt tattaggttg aactgaaagg gtttttgtaa attttttggc
2161 caaaattttt taaaacatac ttactttgga ctagggtac attcttacaa aataaataaa
2221 cagtttttaa aattgtttag acacagatat ttggaattag ctatcttagt gccaactgct
2281 tttatttt ttactccatc aaggtgatgt aagtgactca cctttaaagt tttttagtg
2341 ttatttttta tcactactct gggaaatggt ttgtcttcaa gatgcaatac ttttcttagt
2401 aaaggaaaaa cagcataaaa agataccctgg tctgccttgt acaagaaaag gcaatattag
2461 aggaagaaaa tttaaagaaa agctagagga aaaaaaatt tttttaaaaa tacttattag
2521 aagcaaactg cccttgcatg gaaaactgtt tattttttc agtgaaaaggg aattctgctt
2581 tcgtgttttt gggaaagcag gaactgagtt cattacatct ttaatttggc agaaattagc
2641 ctttctgtga accagatgtg gtttgggca gatctgtagt aaacaatggt gattttattt
2701 atttttactc tctggaaaag gagataatac aattccagaa agtgaactca tatttctaag
2761 gttaagattc cctttattg cacctagaat agtgctatgc acagagcggg tgcttgagtt
2821 gttgtcgttt ttgttttgtt ttttaaatgt aaactggtaa atttgtgct tatcttcaag
2881 gctggcttaa gtataaaatt gttttttaaa cacttgaaaa attaaaggat ttgtttata
2941 tt
```

FIGURE 7 CONT'D

Homo sapiens receptor-like tyrosine kinase (RYK), protein variant 1: SEQ ID NO: 42

```
1    MRGAARLGRP GRSCLPGARG LRAPPPPPLL LLLALLPLLP APGAAAAPAP RPPELQSASA
61   GPSVSLYLSE DEVRRLIGLD AELYYVRNDL ISHYALSFSL LVPSETNFLH FTWHAKSKVE
121  YKLGFQVDNV LAMDMPQVNI SVQGEVPRTL SVFRVELSCT GKVDSEVMIL MQLNLTVNSS
181  KNFTVLNFKR RKMCYKKLEE VKTSALDKNT SRTIYDPVHA APTTSTRVFY ISVGVCCAVI
241  FLVAIILAVL HLHSMKRIEL DDSISASSSS QGLSQPSTQT TQYLRADTPN NATPITSSLG
301  YPTLRIEKND LRSVTLLEAK GKVKDIAISR ERITLKDVLQ EGTFGRIFHG ILIDEKDPNK
361  EKQAFVKTVK DQASEIQVTM MLTESCKLRG LHHRNLLPIT HVCIEEGEKP MVILPYMNWG
421  NLKLFLRQCK LVEANNPQAI SQQDLVHMAI QIACGMSYLA RREVIHKDLA ARNCVIDDTL
481  QVKITDNALS RDLFPMDYHC LGDNENRPVR WMALESLVNN EFSSASDVWA FGVTLWELMT
541  LGQTPYVDID PFEMAAYLKD GYRIAQPINC PDELFAVMAC CWALDPEERP KFQQLVQCLT
601  EFHAALGAYV
```

Homo sapiens receptor-like tyrosine kinase (RYK), transcript variant 2: SEQ ID NO: 43

```
   1 cggctcgggg ctgtgagcgg ctcggggccg ggggtgggcg gcggtgcggc gggcggccga
  61 cgctcctctt cggcggcggc ggcggcggcc atgcgtgggg cggcgcggct ggggcggcg
 121 ggccggagtt gcctcccggg ggcccgcggc ctgagggccc cgccgccgcc gccgctgctg
 181 cttctgcttg cgctgttgcc gctgctgccc gcgcctggcg ctgccgccgc cccgccccg
 241 cggccccgg agctgcagtc ggcttccgcg gggcccagcg tgagtctcta cctgagcgag
 301 gacgaggtgc gccggctgat cggtcttgat gcagaacttt attatgtgag aaatgacctt
 361 attagtcact acgctctatc cttagtctg ttagtaccca gtgagacaaa tttcctgcac
 421 ttcacctggc atgcgaagtc caaggttgaa tataagctgg gattccaagt ggacaatgtt
 481 ttggcaatgg atatgccca ggtcaacatt tctgttcagg gcgaagttcc acgcacttta
 541 tcagtgtttc gggtagagct ttcctgtact ggcaaagtag attctgaagt tatgatacta
 601 atgcagctca acttgacagt aaattcttca aaaaatttta ccgtcttaaa ttttaaacga
 661 aggaaaatgt gctacaaaaa acttgaagaa gtaaaaactt cagccttgga caaaaacact
 721 agcagaacta tttatgatcc tgtacatgca gctccaacca ctctacgcg tgtgttttat
 781 attagtgtag gggttgttg tgcagtaata tttctcgtag caataatatt agctgttttg
 841 caccttcata gtatgaaaag gattgaactg gatgacagca ttagtgccag cagtagttcc
 901 caaggcgtgt ctcagccatc cacccagacg actcagtatc tgagagcaga cacgcccaac
 961 aatgcaactc ctatcaccag ttatcctacc ttgcggatag agaagaacga cttgagaagt
1021 gtcactcttt tggaggccaa aggcaaggtg aaggatatag caatatccag agagaggata
1081 actctaaaag atgtactcca agaaggtact tttgggcgta ttttccatgg gattttaata
1141 gatgaaaaag atccaaataa agaaaaacaa gcatttgtca aaacagttaa agatcaagct
1201 tctgaaattc aggtgacaat gatgctcact gaaagttgta agctgcgagg tcttcatcac
1261 agaaatcttc ttcctattac tcatgtgtgt atagaagaag gagaaaagcc catggtgata
1321 ttgccttaca tgaattgggg gaatcttaaa ttgttttttac gacagtgcaa gttagtagag
1381 gccaataatc cacaggcaat ttctcagcaa gacctggtac acatggctat tcagattgcc
1441 tgtggaatga gctacctggc cagaagggaa gtcatccaca aagccctggc tgccaggaac
1501 tgtgtcattg atgacacact tcaagttaag atcacagaca atgccctctc cagagacttg
1561 ttcccccatgg actatcactg tctgggggac aatgaaaaca ggccagttcg ttggatggct
1621 cttgaaagtc tggttaataa cgagttctct agcgctagtg atgtgtgggc ctttggagtg
```

```
1681 acgctgtggg aactcatgac tctgggccag actccctacg tggacattga cccttcgag
1741 atggccgcat acctgaaaga tggttaccga atagcccagc caatcaactg tcctgatgaa
```

FIGURE 7 CONT'D

```
1801 ttatttgctg tgatggcctg ttgctgggcc ttagatccag aggagaggcc caagtttcag
1861 cagctggtac agtgcctaac agagtttcat gcagccctgg gggcctacgt ctgactcctc
1921 tccaatccca caccatcagg aagaaggtgc ctgtcggggc tcacttgaag cctgtcaggg
1981 atgctttgta tctaacacaa cgccaacaga agcacatttg tcttccagaa caccgtgcct
2041 tagaaatgct ttagaatctg aacttttaa gacagactta ataatgtggc atattttcta
2101 gatatcactt ttattaggtt gaactgaaag ggttttttgta aatttttttgg ccaaaatttt
2161 ttaaaacata cttactttgg actaggggta cattcttaca aaataaataa acagttttta
2221 aaatgtttta gacacagata tttggaatta gctatcttag tgccaactgc ttttratttt
2281 tttacttcat caaggtgatg taagtgactc acctttaaag ttttttttagt gttattttttt
2341 atcactactc tgggaaatgg tttgtcttca agatgcaata cttttcttag taaaggaaaa
2401 acagcataaa aagatacctg gtctgccttg tacaagaaaa ggcaatatta gaggaagaaa
2461 atttaaagaa aagctagagg aaaaaaaaat ttttttaaaa atacttatta gaagcaaact
2521 gcccttgcat ggaaactgt ttatttttt cagtgaaaag gaattctgct ttcgtgtttt
2581 tgggaaagca ggaactgagt tcattacatc tttaatttgg cagaaattag cctttctgtg
2641 aaccagatgt ggtttggggc agatctgtag taaacaatgg tgattttatt tatttttact
2701 ctctggaaaa ggagataata caattccaga aagtgaactc atatttctaa ggttaagatt
2761 cccttttatt gcacctagaa tagtgctatg cacagagcgg gtgcttgagt tgttgtcgtt
2821 ttttgttttgt tttttaaatg taaactggta aattttgtgc ttatcttcaa ggctggctta
2881 agtataaaat tgttttttaa acacttgaaa aattaaagga tttgtttttat att
```

Homo sapiens receptor-like tyrosine kinase (RYK) protein variant 2: SEQ ID NO: 44

```
1    MRGAARLGRP GRSCLPGARG LRAPPPPPLL LLLALLPLLP APGAAAAPAP RPPELQSASA
61   GPSVSLYLSE DEVRRLIGLD AELYYVRNDL ISHYALSFSL LVPSETNFLH FTWHAKSKVE
121  YKLGFQVDNV LAMDMPQVNI SVQGEVPRTL SVFRVELSCT GKVDSEVMIL MQLNLTVNSS
181  KNFTVLNFKR RKMCYKKLEE VKTSALDKNT SRTIYDPVHA APTTSTRVFY ISVGVCCAVI
241  FLVAIILAVL HLHSMKRIEL DDSISASSSS QGLSQPSTQT TQYLRADTPN NATPITSYPT
301  LRIEKNDLRS VTLLEAKGKV KDIAISRERI TLKDVLQEGT FGRIFHGILI DEKDPNKEKQ
361  AFVKTVKDQA SEIQVTMMLT ESCKLRGLHH RNLLPITHVC IEEGEKPMVI LPYMNWGNLK
421  LFLRQCKLVE ANNPQAISQQ DLVHMAIQIA CGMSYLARRE VIHKDLAARN CVIDDTLQVK
481  ITDNALSRDL FPMDYHCLGD NENRPVRWMA LESLVNNEFS SASDVWAFGV TLWELMTLGQ
541  TPYVDIDPFE MAAYLKDGYR IAQPINCPDE LFAVMACCWA LDPEERPKFQ QLVQCLTEFH
601  AALGAYV
```

FIGURE 8 scFv3
SEQ ID No. 1
```
1    EVQLLESGGG LVQPGGSLRL SCAASGFTFS SYAMSWVRQA PGKGLEWVSL
51   IHKAGHTT*Y ADSVKGRFTI SRDNSKNTLY LQMNSLRAED TAVYYCAKGY
101  RHFDYWGQGT LVTVSSGGGG SGGGGSGGGG STDIQMTQSP SSLSASVGDR
151  VAITCRASQS ISSYLNWYQQ KPGKAPKLLI YRASNLQSGV PSRFSGSGSG
201  TDFTLTISSL QPEDFATYYC QQAVGSPRTF GQGTKVEIKR
```

SEQ ID No. 21
```
5'-gaggtgcagctgttggagtctgggggaggcttggtacagcctggggggtccctgagactctcctgtgc
agcctctggattcacctttagcagctatgccatgagctgggtccgccaggctccagggaaggggctggagt
gggtctcactgattcataaggctggtcatactacacagtacgcagactccgtgaagggccggttcaccatc
tccagagacaattccaagaacacgctgtatctgcaaatgaacagcctgagagccgaggacacggccgtata
ttactgtgcgaaaggttatcgtcattttgactactggggccagggaaccctggtcaccgtctcgagcggtg
gaggcggttcaggcggaggtggcagcggcggtggcggtcgacggacatccagatgacccagtctccatcc
tccctgtctgcatctgtaggagacagagtcgccatcacttgccgggcaagtcagagcattagcagctattt
aaattggtatcagcagaaaccagggaaagcccctaagctcctgatctatcgggcatccaatttgcaaagtg
gggtcccatcaaggttcagtggcagtggatctgggacagatttcactctcaccatcagcagtctgcaacct
gaagattttgcaacttactactgtcaacaggctgttggttctcctcgtacgttcggccaagggaccaaggt
ggaaatcaaacgg -3'
``` scFv3 VH
SEQ ID No. 22

```
5'- gaggtgcagctgttggagtctgggggaggcttggtacagcctggggggtccctgagactctcctgtgc
agcctctggattcacctttagcagctatgccatgagctgggtccgccaggctccagggaaggggctggagt
gggtctcactgattcataaggctggtcatactacacagtacgcagactccgtgaagggccggttcaccatc
tccagagacaattccaagaacacgctgtatctgcaaatgaacagcctgagagccgaggacacggccgtata
ttactgtgcgaaaggttatcgtcattttgactactggggccagggaaccctggtcaccgtctcgagc-3'
``` scFv3 VL
SEQ ID No. 23
```
5'-gacatccagatgacccagtctccatcctccctgtctgcatctgtaggagacagagtcgccatcac
ttgccgggcaagtcagagcattagcagctatttaaattggtatcagcagaaaccagggaaagcccta
agctcctgatctatcgggcatccaatttgcaaagtggggtcccatcaaggttcagtggcagtggatct
gggacagatttcactctcaccatcagcagtctgcaacctgaagattttgcaacttactactgtcaaca
ggctgttggttctcctcgtacgttcggccaagggaccaaggtggaaatcaaacgg-3'
``` scFv3 CDRH1
SEQ ID No. 24
5'-agctatgccatgagc-3' scFv3 CDRH2
SEQ ID No. 25
5'- ctgattcataaggctggtcatactacacagtacgcagactccgtgaagggc-3'

FIGURE 8 CONT'D scFv3 CDRH3
SEQ ID No. 26
5'-ggttatcgtcattttgac-3' scFv3 CDRL1
SEQ ID No. 27
5'-cgggcaagtcagagcattagcagctatttaaat-3' scFv3 CDRL2
SEQ ID No. 28
5'-cgggcatccaatttgcaaagtggggtcccatca-3' scFv3 CDRL3
SEQ ID No. 29
5'-gctgttggttctcctcgtacg-3' scFvN3
SEQ ID No. 10
```
1   EVQLLESGGG LV*PGGSLRL SCAASGFTFS SYAMSWVRQA PGKGLEWVST
51  ISRVGFPTVY ADSVKGRFTI SRDNSKNTLY LQMNSLRAED TAVYYCAKRG
101 HPFDYWGQGT LVTVSSGGGG SGGGGSGGGG STDIQMTQSP SSLSASVGDR
151 VTITCRASQS ISSYLNWYQQ KPGKAPKLLI YQASVLQSGV PSRFSGSGSG
201 TDFTLTISSL QPEDFATYYC QQPGPAPPTF GQGTKVEIKR
```

SEQ ID No. 30
5'-gaggtgcagctgttggagtctggggggaggcttggtatagcctgggggtccctgagactctcctgtgc
agcctctggattcacctttagcagctatgccatgagctgggtccgccaggctccagggaaggggctggagt
gggtctcaacgatttcgcgggttggttttccgacagtttacgcagactccgtgaagggccggttcaccatc
tccagagacaattccaagaacacgctgtatctgcaaatgaacagcctgagagccgaggacacggccgtata
ttactgtgcgaaacgtggtcatccgtttgactactggggccagggaaccctggtcaccgtctcgagcggtg
gaggcggttcaggcggaggtggcagcggcggtggcgggtcgacggacatccagatgacccagtctccatcc
tccctgtctgcatctgtaggagacagagtcaccatcacttgccgggcaagtcagagcattagcagctattt
aaattggtatcagcagaaaccagggaaagcccctaagctcctgatctatcaggcatccgttttgcaaagtg
gggtcccatcaaggttcagtggcagtggatctgggacagatttcactctcaccatcagcagtctgcaacct
gaagattttgcaacttactactgtcaacagccgggtcctgctcctccgacgttcggccaagggaccaaggt
ggaaatcaaacgg-3' scFvN3 VH
SEQ ID No. 31
5'-gaggtgcagctgttggagtctggggggaggcttggtatagcctgggggtccctgagactctcctgtg
cagcctctggattcacctttagcagctatgccatgagctgggtccgccaggctccagggaaggggctggag
tgggtctcaacgatttcgcgggttggttttccgacagtttacgcagactccgtgaagggccggttccacat
ctccagagacaattccaagaacacgctgtatctgcaaatgaacagcctgagagccgaggacacggccgtat
attactgtgcgaaacgtggtcatccgtttgactactggggccagggaaccctggtcaccgtctcgagc-3' scFvN3 VL
SEQ ID No. 32
5'-gacatccagatgacccagtctccatcctccctgtctgcatctgtaggagacagagtcaccatcacttg
ccgggcaagtcagagcattagcagctatttaaattggtatcagcagaaaccagggaaagcccctaagctcc
tgatctatcaggcatccgttttgcaaagtggggtcccatcaaggttcagtggcagtggatctgggacagat
ttcactctcaccatcagcagtctgcaacctgaagattttgcaacttactactgtcaacagccgggtcctgc
tcctccgacgttcggccaagggaccaaggtggaaatcaaacgg-3'

FIGURE 8 CONT'D scFvN3 CDRH1
SEQ ID No. 33
5'-agctatgccatgagc-3' scFvN3 CDRH2
SEQ ID No. 34
5'-acgatttcgcgggttggttttccgacagtttacgcagactccgtgaagggccggttcacc-3' scFvN3 CDRH3
SEQ ID No. 35
5'-cgtggtcatccgtttgac-3' scFvN3 CDRL1
SEQ ID No. 36
5'-cgggcaagtcagagcattagcagctatttaaat-3' scFvN3 CDRL2
SEQ ID No. 37
5'-caggcatccgttttgcaaagtggggtcccatcaaggttcagt-3' scFvN3 CDRL3
SEQ ID No. 38
5'-ccgggtcctgctcctccgacgttcggccaa-3'

FIGURE 9

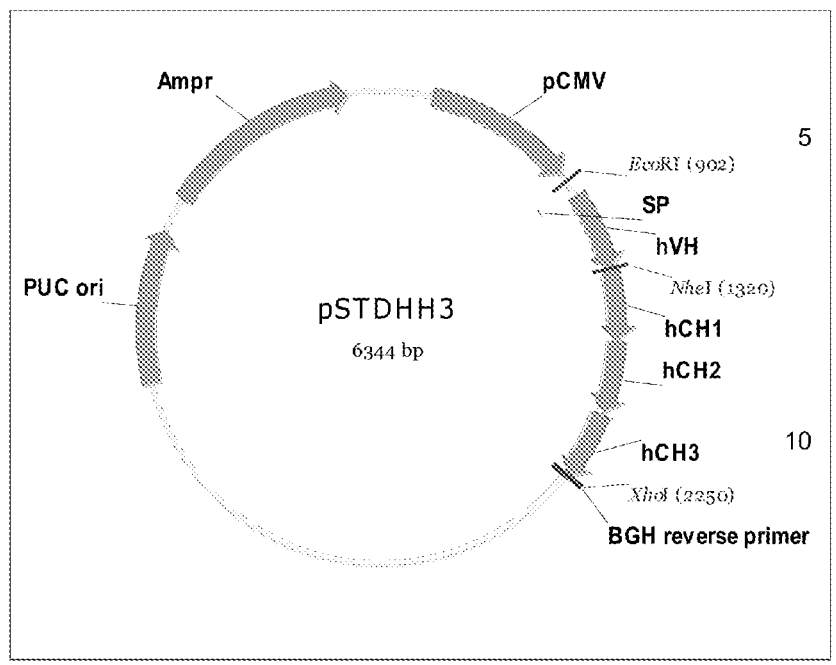

Heavy chain Sequence of N3 IgG1: SEQ ID NO: 45 <u>SP-VH-CH1-CH2-CH3</u>:

```
            M   E   L   G   L   S   W   I   F   L   L   A   I   L   K
  1        ATG GAA CTG GGC CTG AGC TGG ATC TTC CTG CTG GCC ATC CTG AAG
           TAC CTT GAC CCG GAC TCG ACC TAG AAG GAC GAC CGG TAG GAC TTC
            G   V   Q   C   E   V   Q   L   L   E   S   G   G   G   L
  46       GGC GTG CAG TGC GAG GTG CAG CTG TTG GAG TCT GGG GGA GGC TTG
           CCG CAC GTC ACG CTC CAC GTC GAC AAC CTC AGA CCC CCT CCG AAC
            V   Q   P   G   G   S   L   R   L   S   C   A   A   S   G
  91       GTA CAG CCT GGG GGG TCC CTG AGA CTC TCC TGT GCA GCC TCT GGA
           CAT GTC GGA CCC CCC AGG GAC TCT GAG AGG ACA CGT CGG AGA CCT
            F   T   F   S   S   Y   A   M   S   W   V   R   Q   A   P
  136      TTC ACC TTT AGC AGC TAT GCC ATG AGC TGG GTC CGC CAG GCT CCA
           AAG TGG AAA TCG TCG ATA CGG TAC TCG ACC CAG GCG GTC CGA GGT
            G   K   G   L   E   W   V   S   L   I   H   K   A   G   H
  181      GGG AAG GGG CTG GAG TGG GTC TCA CTG ATT CAT AAG GCT GGT CAT
```

FIGURE 9 CONT'D

```
              CCC TTC CCC GAC CTC ACC CAG AGT GAC TAA GTA TTC CGA CCA GTA

T   T   Q   Y   A   D   S   V   K   G   R   F   T   I   S
        226   ACT ACA CAG TAC GCA GAC TCC GTG AAG GGC CGG TTC ACC ATC TCC
              TGA TGT GTC ATG CGT CTG AGG CAC TTC CCG GCC AAG TGG TAG AGG
              R   D   N   S   K   N   T   L   Y   L   Q   M   N   S   L
        271   AGA GAC AAT TCC AAG AAC ACG CTG TAT CTG CAA ATG AAC AGC CTG
              TCT CTG TTA AGG TTC TTG TGC GAC ATA GAC GTT TAC TTG TCG GAC
              R   A   E   D   T   A   V   Y   Y   C   A   K   G   Y   R
        316   AGA GCC GAG GAC ACG GCC GTA TAT TAC TGT GCG AAA GGT TAT CGT
              TCT CGG CTC CTG TGC CGG CAT ATA ATG ACA CGC TTT CCA ATA GCA
              H   F   D   Y   W   G   Q   G   T   L   V   T   V   S   S
        361   CAT TTT GAC TAC TGG GGC CAG GGA ACC CTG GTC ACC GTC TCC AGC
              GTA AAA CTG ATG ACC CCG GTC CCT TGG GAC CAG TGG CAG AGG TCG
              A   S   T   K   G   P   S   V   F   P   L   A   P   S   S
        406   GCT AGC ACC AAG GGC CCA TCG GTC TTC CCC CTG GCA CCC TCC TCC
              CGA TCG TGG TTC CCG GGT AGC CAG AAG GGG GAC CGT GGG AGG AGG
              K   S   T   S   G   G   T   A   A   L   G   C   L   V   K
        451   AAG AGC ACC TCT GGG GGC ACA GCG GCC CTG GGC TGC CTG GTC AAG
              TTC TCG TGG AGA CCC CCG TGT CGC CGG GAC CCG ACG GAC CAG TTC
              D   Y   F   P   E   P   V   T   V   S   W   N   S   G   A
        496   GAC TAC TTC CCC GAA CCG GTG ACG GTG TCG TGG AAC TCA GGC GCC
              CTG ATG AAG GGG CTT GGC CAC TGC CAC AGC ACC TTG AGT CCG CGG
              L   T   S   G   V   H   T   F   P   A   V   L   Q   S   S
        541   CTG ACC AGC GGC GTG CAC ACC TTC CCG GCT GTC CTA CAG TCC TCA
              GAC TGG TCG CCG CAC GTG TGG AAG GGC CGA CAG GAT GTC AGG AGT
              G   L   Y   S   L   S   S   V   V   T   V   P   S   S   S
        586   GGA CTC TAC TCC CTC AGC AGC GTG GTG ACC GTG CCC TCC AGC AGC
              CCT GAG ATG AGG GAG TCG TCG CAC CAC TGG CAC GGG AGG TCG TCG
              L   G   T   Q   T   Y   I   C   N   V   N   H   K   P   S
        631   TTG GGC ACC CAG ACC TAC ATC TGC AAC GTG AAT CAC AAG CCC AGC
              AAC CCG TGG GTC TGG ATG TAG ACG TTG CAC TTA GTG TTC GGG TCG
              N   T   K   V   D   K   K   V   E   P   K   S   C   D   K
        676   AAC ACC AAG GTG GAC AAG AAA GTT GAG CCC AAA TCT TGT GAC AAA
              TTG TGG TTC CAC CTG TTC TTT CAA CTC GGG TTT AGA ACA CTG TTT
              T   H   T   C   P   P   C   P   A   P   E   L   L   G   G
        721   ACT CAC ACA TGC CCA CCG TGC CCA GCA CCT GAA CTC CTG GGG GGA
              TGA GTG TGT ACG GGT GGC ACG GGT CGT GGA CTT GAG GAC CCC CCT
              P   S   V   F   L   F   P   P   K   P   K   D   T   L   M
        766   CCG TCA GTC TTC CTC TTC CCC CCA AAA CCC AAG GAC ACC CTC ATG
              GGC AGT CAG AAG GAG AAG GGG GGT TTT GGG TTC CTG TGG GAG TAC
              I   S   R   T   P   E   V   T   C   V   V   V   D   V   S
        811   ATC TCC CGG ACC CCT GAG GTC ACA TGC GTG GTG GTG GAC GTG AGC
```

TAG AGG GCC TGG GGA CTC CAG TGT ACG CAC CAC CAC CTG CAC TCG

FIGURE 9 CONT'D

```
         H   E   D   P   E   V   K   F   N   W   Y   V   D   G   V
  856   CAC GAA GAC CCT GAG GTC AAG TTC AAC TGG TAC GTG GAC GGC GTG
        GTG CTT CTG GGA CTC AG TTC AAG TTG ACC ATG CAC CTG CCG CAC
         E   V   H   N   A   K   T   K   P   R   E   E   Q   Y   N
  901   GAG GTG CAT AAT GCC AAG ACA AAG CCG CGG GAG GAG CAG TAC AAC
        CTC CAC GTA TTA CGG TTC TGT TTC GGC GCC CTC CTC GTC ATG TTG
         S   T   Y   R   V   V   S   V   L   T   V   L   H   Q   D
  946   AGC ACG TAC CGT GTG GTC AGC GTC CTC ACC GTC CTG CAC CAG GAC
        TCG TGC ATG GCA CAC CAG TCG CAG GAG TGG CAG GAC GTG GTC CTG
         W   L   N   G   K   E   Y   K   C   K   V   S   N   K   A
  991   TGG CTG AAT GGC AAG GAG TAC AAG TGC AAG GTC TCC AAC AAA GCC
        ACC GAC TTA CCG TTC CTC ATG TTC ACG TTC CAG AGG TTG TTT CGG
         L   P   A   P   I   E   K   T   I   S   K   A   K   G   Q
 1036   CTC CCA GCC CCC ATC GAG AAA ACC ATC TCC AAA GCC AAA GGG CAG
        GAG GGT CGG GGG TAG CTC TTT TGG TAG AGG TTT CGG TTT CCC GTC
         P   R   E   P   Q   V   Y   T   L   P   P   S   R   E   E
 1081   CCC CGA GAA CCA CAG GTG TAC ACC CTG CCC CCA TCC CGG GAG GAG
        GGG GCT CTT GGT GTC CAC ATG TGG GAC GGG GGT AGG GCC CTC CTC
         M   T   K   N   Q   V   S   L   T   C   L   V   K   G   F
 1126   ATG ACC AAG AAC CAG GTC AGC CTG ACC TGC CTG GTC AAA GGC TTC
        TAC TGG TTC TTG GTC CAG TCG GAC TGG ACG GAC CAG TTT CCG AAG
         Y   P   S   D   I   A   V   E   W   E   S   N   G   Q   P
 1171   TAT CCC AGC GAC ATC GCC GTG GAG TGG GAG AGC AAT GGG CAG CCG
        ATA GGG TCG CTG TAG CGG CAC CTC ACC CTC TCG TTA CCC GTC GGC
         E   N   N   Y   K   T   T   P   P   V   L   D   S   D   G
 1216   GAG AAC AAC TAC AAG ACC ACG CCT CCC GTG CTG GAC TCC GAC GGC
        CTC TTG TTG ATG TTC TGG TGC GGA GGG CAC GAC CTG AGG CTG CCG
         S   F   F   L   Y   S   K   L   T   V   D   K   S   R   W
 1261   TCC TTC TTC CTC TAC AGC AAG CTC ACC GTG GAC AAG AGC AGG TGG
        AGG AAG AAG GAG ATG TCG TTC GAG TGG CAC CTG TTC TCG TCC ACC
         Q   Q   G   N   V   F   S   C   S   V   M   H   E   A   L
 1306   CAG CAG GGG AAC GTC TTC TCA TGC TCC GTG ATG CAT GAG GCT CTG
        GTC GTC CCC TTG CAG AAG AGT ACG AGG CAC TAC GTA CTC CGA GAC
         H   N   H   Y   T   Q   K   S   L   S   L   S   P   G   K
 1351   CAC AAC CAC TAC ACG CAG AAG AGC CTC TCC CTG TCT CCG GGT AAA
        GTG TTG GTG ATG TGC GTC TTC TCG GAG AGG GAC AGA GGC CCA TTT
         *
 1396   TGA
        ACT
```

FIGURE 9 CONT'D

RWD1 heavy chain
SEQ ID No. 39

5'-
atggaactgggcctgagctggatcttcctgctggccatcctgaagggcgtgcagtgcgaggt
gcagctgttggagtctgggggaggcttggtacagcctggggggtccctgagactctcctgtg
cagcctctggattcacctttagcagctatgccatgagctgggtccgccaggctccagggaag
gggctggagtgggtctcactgattcataaggctggtcatactacacagtacgcagactccgt
gaagggccggttcaccatctccagagacaattccaagaacacgctgtatctgcaaatgaaca
gcctgagagccgaggacacggccgtatattactgtgcgaaaggttatcgtcattttgactac
tggggccagggaaccctggtcaccgtctccagcgctagcaccaagggcccatcggtcttccc
cctggcaccctcctccaagagcacctctggggcacagcggccctgggctgcctggtcaagg
actacttccccgaaccggtgacggtgtcgtggaactcaggcgccctgaccagcggcgtgcac
accttcccggctgtcctacagtcctcaggactctactccctcagcagcgtggtgaccgtgcc
ctccagcagcttgggcacccagacctacatctgcaacgtgaatcacaagcccagcaacacca
aggtggacaagaaagttgagcccaaatcttgtgacaaaactcacacatgcccaccgtgccca
gcacctgaactcctggggggaccgtcagtcttcctcttccccccaaaacccaaggacaccct
catgatctcccggacccctgaggtcacatgcgtggtggtggacgtgagccacgaagaccctg
aggtcaagttcaactggtacgtggacggcgtggaggtgcataatgccaagacaaagccgcgg
gaggagcagtacaacagcacgtaccgtgtggtcagcgtcctcaccgtcctgcaccaggactg
gctgaatggcaaggagtacaagtgcaaggtctccaacaaagccctcccagcccccatcgaga
aaaccatctccaaagccaaagggcagccccgagaaccacaggtgtacaccctgcccccatcc
cgggaggagatgaccaagaaccaggtcagcctgacctgcctggtcaaaggcttctatcccag
cgacatcgccgtggagtgggagagcaatgggcagccggagaacaactacaagaccacgcctc
ccgtgctggactccgacggctccttcttcctctacagcaagctcaccgtggacaagagcagg
tggcagcaggggaacgtcttctcatgctccgtgatgcatgaggctctgcacaaccactacac
gcagaagagcctctccctgtctccgggtaaa-3'

FIGURE 10

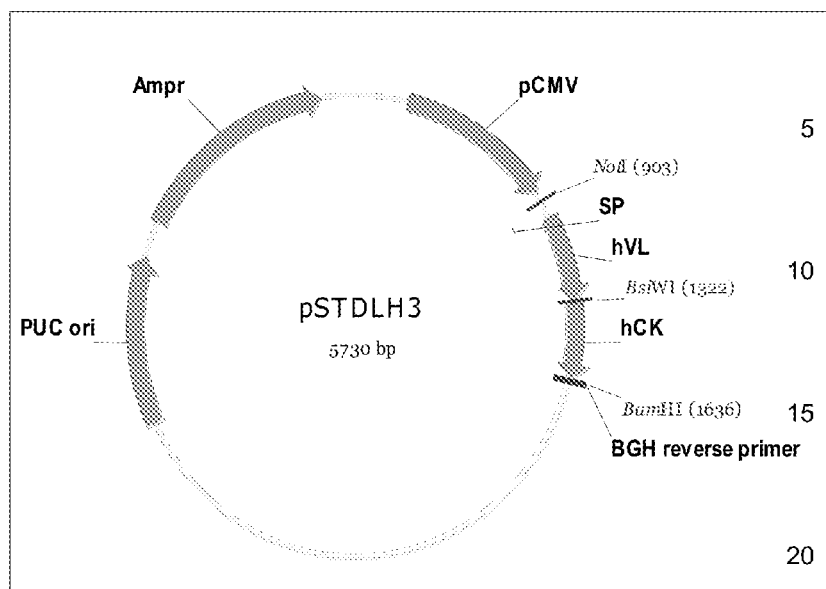

Light chain Sequence of N3 IgG1: SEQ ID NO: 46 SP-VL-CK:

```
           M   R   V   P   A   Q   L   L   G   L   L   L   L   W   L
  1       ATG CGC GTG CCT GCC CAG CTG CTG GGC CTG CTC CTG CTG TGG CTG
          TAC GCG CAC GGA CGG GTC GAC GAC CCG GAC GAG GAC GAC ACC GAC
           P   G   T   R   C   D   I   Q   M   T   Q   S   P   S   S
  46      CCC GGC ACC CGG TGC GAC ATC CAG ATG ACC CAG TCT CCA TCC TCC
          GGG CCG TGG GCC ACG CTG TAG GTC TAC TGG GTC AGA GGT AGG AGG
           L   S   A   S   V   G   D   R   V   A   I   T   C   R   A
  91      CTG TCT GCA TCT GTA GGA GAC AGA GTC GCC ATC ACT TGC CGG GCA
          GAC AGA CGT AGA CAT CCT CTG TCT CAG CGG TAG TGA ACG GCC CGT
           S   Q   S   I   S   S   Y   L   N   W   Y   Q   Q   K   P
 136      AGT CAG AGC ATT AGC AGC TAT TTA AAT TGG TAT CAG CAG AAA CCA
          TCA GTC TCG TAA TCG TCG ATA AAT TTA ACC ATA GTC GTC TTT GGT
           G   K   A   P   K   L   L   I   Y   R   A   S   N   L   Q
 181      GGG AAA GCC CCT AAG CTC CTG ATC TAT CGG GCA TCC AAT TTG CAA
          CCC TTT CGG GGA TTC GAG GAC TAG ATA GCC CGT AGG TTA AAC GTT
           S   G   V   P   S   R   F   S   G   S   G   S   G   T   D
 226      AGT GGG GTC CCA TCA AGG TTC AGT GGC AGT GGA TCT GGG ACA GAT
          TCA CCC CAG GGT AGT TCC AAG TCA CCG TCA CCT AGA CCC TGT CTA
           F   T   L   T   I   S   S   L   Q   P   E   D   F   A   T
 271      TTC ACT CTC ACC ATC AGC AGT CTG CAA CCT GAA GAT TTT GCA ACT
```

FIGURE 10 CONT'D

```
            AAG TGA GAG TGG TAG TCG TCA GAC GTT GGA CTT CTA AAA CGT TGA
             Y   Y   C   Q   Q   A   V   G   S   P   R   T   F   G   Q
     316    TAC TAC TGT CAA CAG GCT GTT GGT TCT CCT CGT ACC TTC GGC CAA
            ATG ATG ACA GTT GTC CGA CAA CCA AGA GGA GCA TGG AAG CCG GTT
             G   T   K   V   E   I   K   R   T   V   A   A   P   S   V
     361    GGG ACC AAG GTG GAA ATC AAA CGA ACT GTG GCT GCA CCA TCT GTC
            CCC TGG TTC CAC CTT TAG TTT GCT TGA CAC CGA CGT GGT AGA CAG
             F   I   F   P   P   S   D   E   Q   L   K   S   G   T   A
     406    TTC ATC TTC CCG CCA TCT GAT GAG CAG TTG AAA TCT GGA ACT GCC
            AAG TAG AAG GGC GGT AGA CTA CTC GTC AAC TTT AGA CCT TGA CGG
             S   V   V   C   L   L   N   N   F   Y   P   R   E   A   K
     451    TCT GTT GTG TGC CTG CTT AAT AAC TTC TAT CCC AGG GAG GCC AAA
            AGA CAA CAC ACG GAC GAA TTA TTG AAG ATA GGG TCC CTC CGG TTT
             V   Q   W   K   V   D   N   A   L   Q   S   G   N   S   Q
     496    GTA CAG TGG AAG GTG GAT AAC GCC CTC CAA TCG GGT AAC TCC CAG
            CAT GTC ACC TTC CAC CTA TTG CGG GAG GTT AGC CCA TTG AGG GTC
             E   S   V   T   E   Q   D   S   K   D   S   T   Y   S   L
     541    GAG AGT GTC ACA GAG CAG GAC AGC AAG GAC AGC ACC TAC AGC CTC
            CTC TCA CAG TGT CTC GTC CTG TCG TTC CTG TCG TGG ATG TCG GAG
             S   S   T   L   T   L   S   K   A   D   Y   E   K   H   K
     586    AGC AGC ACC CTG ACG CTG AGC AAA GCA GAC TAC GAG AAA CAC AAA
            TCG TCG TGG GAC TGC GAC TCG TTT CGT CTG ATG CTC TTT GTG TTT
             V   Y   A   C   E   V   T   H   Q   G   L   S   L   P   V
     631    GTC TAC GCC TGC GAA GTC ACC CAT CAG GGC CTG AGC TTG CCC GTC
            CAG ATG CGG ACG CTT CAG TGG GTA GTC CCG GAC TCG AAC GGG CAG
             T   K   S   F   N   R   G   E
     676    ACA AAG AGC TTC AAC AGG GGA GAG
            TGT TTC TCG AAG TTG TCC CCT CTC
```

FIGURE 10 CONT'D

RWD1 light chain
SEQ ID No. 40

5'-
atgcgcgtgcctgcccagctgctgggcctgctcctgctgtggctgcccggcacccggtgcga
catccagatgacccagtctccatcctccctgtctgcatctgtaggagacagagtcgccatca
cttgccgggcaagtcagagcattagcagctatttaaattggtatcagcagaaaccagggaaa
gcccctaagctcctgatctatcgggcatccaatttgcaaagtggggtcccatcaaggttcag
tggcagtggatctgggacagatttcactctcaccatcagcagtctgcaacctgaagattttg
caacttactactgtcaacaggctgttggttctcctcgtaccttcggccaagggaccaaggtg
gaaatcaaacgaactgtggctgcaccatctgtcttcatcttcccgccatctgatgagcagtt
gaaatctggaactgcctctgttgtgtgcctgcttaataacttctatcccagggaggccaaag
tacagtggaaggtggataacgcctccaatcgggtaactcccaggagagtgtcacagagcag
gacagcaaggacagcacctacagcctcagcagcaccctgacgctgagcaaagcagactacga
gaaacacaaagtctacgcctgcgaagtcacccatcagggcctgagcttgcccgtcacaaaga
gcttcaacaggggagag-3'

ANTIBODIES AGAINST HUMAN RYK AND USES THEREFOR

CROSS REFERENCE TO RELATED APPLICATIONS

This application is the National Stage of International Application No. PCT/AU2014/000353, filed on Apr. 2, 2014, which claims the benefit of Australian Application No. 2013901150, filed on Apr. 3, 2013. The contents of both applications are hereby incorporated by reference in their entirety.

FIELD OF THE INVENTION

The present invention relates to antibodies and antigen-binding fragments thereof that bind RYK, in particular human RYK and their use in regulating RYK-associated activities. The antibodies disclosed herein are useful in treatment of cancer, inflammation and other chronic diseases and nerve injury, including peripheral nerve injury and spinal cord injury.

BACKGROUND OF THE INVENTION

RYK is a unique member of the receptor tyrosine kinase (RTK) family and is a putative pseudokinase. It is part of a small but biologically significant group of RTKs that has a functionally inactive protein tyrosine kinase (PTK) domain, due to substitution of conserved residues required for tyrosine kinase activity. It binds to the Wnt family of ligands via its Wnt inhibitory factor (WIF) domain, and regulates important biological processes including cell differentiation, migration, and axon pathfinding and target selection.

RYK is a cell surface receptor with a single transmembrane domain, a small extracellular region and a tyrosine kinase-like domain located within the cytoplasm. The RYK extracellular domain has a single identified domain, the Wnt inhibitory factor (WIF) domain. This domain was originally described in the soluble WIF-1 protein, which carries out its biological functions by sequestering members of the Wnt or Hedgehog ligand families. RYK has previously been shown to function as a Wnt receptor, and recently to function in mammalian planar cell polarity (PCP) signaling pathways.

Progress in defining the biological role of RYK has trailed many of the other RTK members due to the unusual nature of the ligands and to RYK having no detectable kinase activity. The generation of RYK-deficient mice has shed some light on its functions. RYK$^{-/-}$ mice demonstrated a key role for RYK in craniofacial development and palate closure. RYK is required for neural progenitor cell differentiation into neurons and axon extension, and is critical for correct axon guidance in the developing nervous system. Importantly, RYK was shown to mediate Wnt-induced axon repulsion. In rat models of spinal cord injury, injection of an anti-RYK polyclonal antibody prevented corticospinal tract axon retraction from the lesion, caused sprouting of axons at and caudal to the lesion, and enhanced functional recovery after injury.

Although RYK has an established role in the transduction of Wnt-initiated signals, elucidation of the exact mechanisms by which RYK functions at a molecular and cellular level has remained elusive. It has been shown that RYK can signal via the small GTPase RhoA, though the downstream mediators have not been identified. However, the effects of this pathway are unknown. Inhibiting RYK function with conventional PTK inhibitors has not been possible due to lack of intrinsic kinase activity. While some interactive partners have been identified, they have not yet provided a specific mechanism to antagonize RYK function. Attempts to generate inhibitory antibodies to RYK have been hampered by poor immunogenicity of the receptor extracellular domain, lack of characterized ligands, and lack of structural information as to how the receptor interacts with its ligands and co-receptors.

Previously, monoclonal antibodies to RYK were generated using a soluble version of the entire human RYK extracellular domain expressed in a mammalian expression system (Halford M M, et al., 1999, *J. Biol. Chem.* 274: 7379-7390). While some monoclonal antibodies were made to this region, they were of the IgM isotype, indicating a failure of the immune system to switch to the high-affinity IgG isotype, which is typically seen with antigens that poorly stimulate the immune response.

It has been previously demonstrated that RYK is processed in two steps. A first cleavage event removes the extracellular domain, while a second cleavage is catalyzed by the γ-secretase complex and acts to liberate the RYK intracellular domain (RYK-ICD) (Lyu J, et al., 2008, *Dev Cell* 15: 773-780).

The poor immunogenicity and the constitutive proteolytic processing of the RYK extracellular domain, and potentially reduced availability of the WIF domain associated therewith, have posed a challenge for the generation of inhibitory anti-RYK antibodies. Accordingly, there exists a need to provide a high affinity monoclonal antibody that binds human RYK, in particular the WIF domain of the extracellular domain of RYK.

SUMMARY OF THE INVENTION

In an aspect of the invention, there is provided an isolated monoclonal antibody or antigen-binding fragment or derivative thereof that specifically binds to the extracellular domain of human RYK, in particular, the antibody or antigen-binding fragment thereof, binds specifically to the WIF domain of human RYK.

In one embodiment, the antibodies of the invention are human or humanized antibodies. In another embodiment, the antibodies of the invention may or may not be conjugated to a detectable substance or a therapeutic agent.

In a preferred embodiment, the antibodies of the present invention modulate RYK-associated activity, which includes RYK mediated signal transduction activity and modulation of the interaction of Wnts with RYK and, preferably, modulate Wnt induced signaling. In particular, the antibodies inhibit the binding of Wnt5a and inhibit Wnt induced phosphorylation of Dishevelled (Dvl) 2 and/or Dvl3 proteins. In one embodiment, the antibody of the invention is RWD1, as herein described.

According to another aspect, the present invention provides a method for identifying antibodies that bind to the extracellular domain of human RYK protein, preferably to the WIF domain of human RYK. These antibodies may be screened for the ability to preferentially bind a protein construct that contains the WIF domain of RYK, lacking the carboxyl-terminal cleavage site. Preferably, the antibodies are monoclonal antibodies.

In another aspect, the invention features a pharmaceutical composition containing at least one human anti-RYK antibody and a pharmaceutically acceptable carrier. The pharmaceutical composition can further include a combination of at least one anti-RYK antibody and at least one therapeutic agent. Combinations of the anti-RYK antibody and a therapeutic agent are also within the scope of the invention. The compositions and combinations of the invention can be used to regulate RYK-associated conditions.

In another aspect, the invention features a method of treating a subject with a RYK-associated condition. The method includes administering a therapeutically effective dose of the anti-RYK antibody according to the invention to the subject. In one embodiment, a therapeutically effective dose of an anti-RYK antibody is an amount sufficient to substantially inhibit interaction between RYK and a Wnt protein, thereby substantially modulating Wnt signaling.

In another aspect, the invention provides a method for detecting the presence of RYK in a sample in vitro. Samples may include biological samples such as serum, plasma, tissue and biopsy. The method can be used to diagnose a condition or disorder, such as a RYK-associated condition as described herein. The method includes: (1) contacting the sample or a control sample with an anti-RYK antibody, and (2) detecting formation of a complex between the anti-RYK antibody and the sample or the control sample, wherein a statistically significant change in the formation of the complex in the sample relative to a control sample, is indicative of the presence of RYK in the sample.

In another aspect, the invention provides a method for detecting the presence of RYK in vivo (e.g., in vivo imaging in a subject). The method can be used to diagnose a disorder, a RYK-associated condition as described herein. The method includes: (1) administering an anti-RYK antibody to a subject or a control subject under conditions that allow binding of the antibody to RYK, and (2) detecting formation of a complex between the antibody and RYK, wherein a statistically significant change in the formation of the complex in the subject relative to a control, e.g., a control subject, is indicative of the presence of RYK.

The antibody may be directly or indirectly labeled with a detectable substance to facilitate detection of the bound or unbound antibody. Suitable detectable substances include various enzymes, prosthetic groups, fluorescent materials, luminescent materials and radioactive materials.

According to another aspect, the invention provides diagnostic methods using the anti-RYK antibodies of the invention to detect cancer or evaluate the efficacy of cancer treatment. In particular embodiments, the diagnostic methods of the invention provide methods of imaging and localizing metastases and methods of diagnosis and prognosis using tissues and fluids distal to a primary tumor site, for example, whole blood, sputum, urine, serum, fine needle aspirates (i.e., biopsies). In other embodiments, the diagnostic methods of the invention provide methods of imaging and localizing metastases and methods of diagnosis and prognosis in vivo. In such embodiments, primary and/or metastatic tumors are detected using an antibody of the invention. The antibodies of the invention may also be used for immunohistochemical analyses of frozen or fixed cells or tissue assays.

In another embodiment, the present invention provides kits comprising the pharmaceutical compositions or diagnostic reagents of the invention.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

DESCRIPTION OF THE FIGURES

FIG. 7 shows the amino acid and nucleotide sequences of human RYK.

FIG. 8 shows the amino acid and nucleotide sequences of scFv3 and scFvN3 (underlined codons or residues have been changed from stop codons to glutamine (Q) codons or residues).

FIG. 9 shows the vector map, amino acid and nucleotide sequences of encoding the heavy chain of RWD1.

FIG. 10 shows the vector map, amino acid and nucleotide sequences of encoding the light chain of RWD1.

DETAILED DESCRIPTION OF THE INVENTION

Figure 1:
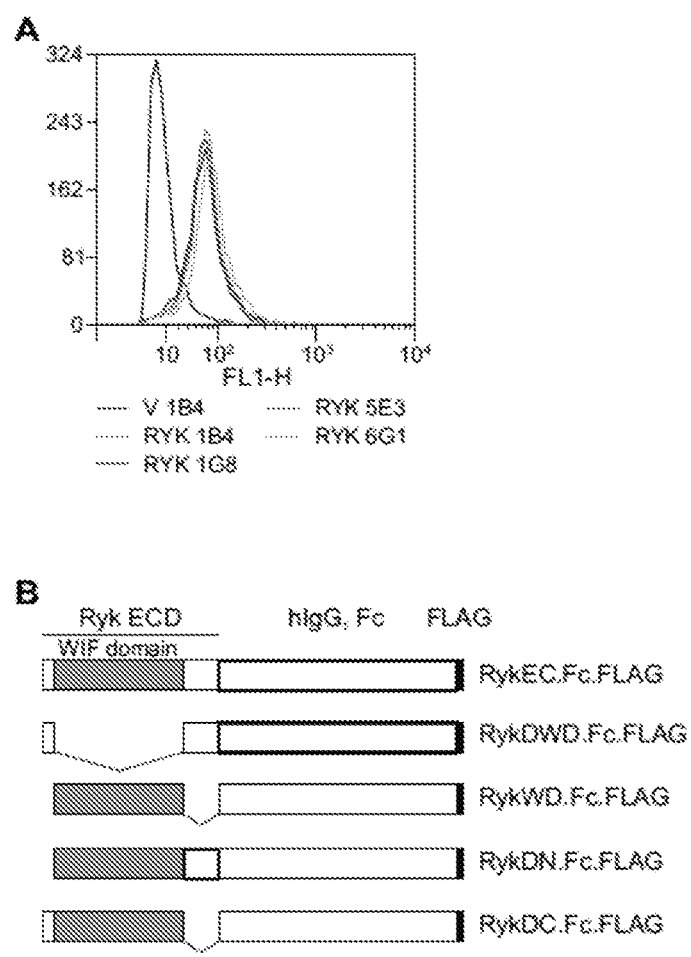
FIG. 1 shows the generation of monoclonal antibodies to the RYK extracellular domain and epitope mapping. (A) Flow cytometry using purified anti-RYK mouse monoclonal antibodies 1B4, 1G8, 5E3 and 6G1. (B) Schematic of the mouse RYK deletion constructs used in this study. (C) Western blot analysis of purified mouse RYK deletion constructs using anti-RYK monoclonal antibodies 1B4 and 6G1. (D) ELISA results using anti-RYK monoclonal antibodies 1B4 and 6G1 on an immobilized peptide library of the entire human RYK extracellular domain.
Figure 1:
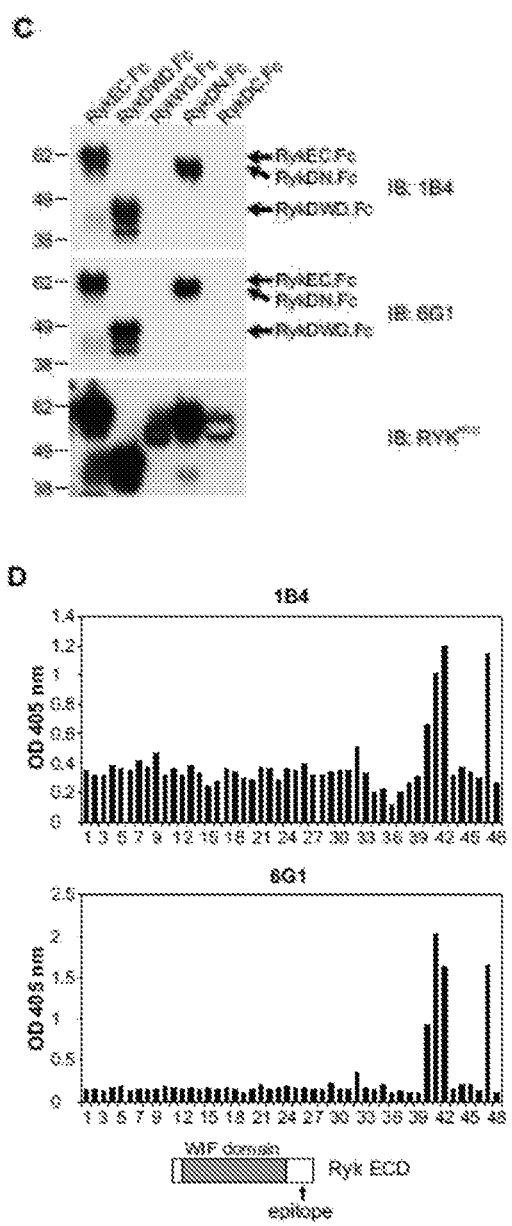

In a first aspect of the present invention, there is provided an isolated monoclonal antibody or antigen-binding fragment or derivative thereof, that specifically binds to the extracellular domain of human RYK, wherein the antibody or antigen-binding fragment thereof, specifically binds to the Wnt inhibitory factor (WIF) domain of human RYK.

Previous attempts to generate monoclonal antibodies to RYK used a soluble version of the entire human RYK extracellular domain (H-RYK-FLAG) expressed in a mammalian expression system. While some monoclonal antibodies were made to this region, they were of the IgM isotype, indicating a failure of the immune system to switch to the high-affinity IgG isotype.

Moreover, as will be demonstrated herein, the extracellular domain of RYK is likely to be proteolytically processed by a matrix metalloprotease to generate a short extracellular domain attached to the transmembrane and cytoplasmic domain of RYK.

Furthermore, antibody mapping has revealed that the IgM antibody binds to a small portion of extracellular domain that remains after proteolytic cleavage of the extracellular domain containing the WIF domain.

Given that only IgM antibodies were able to be generated to the extracellular domain of RYK, the extracellular domain, including the WIF domain, can be considered to be poorly immunogenic. This is further supported by data generated by the inventors which demonstrates that attempts to generate antibodies to the RYK WIF domain alone in mice and rabbits failed to produce any monoclonal antibodies to RYK in the animals' serum.

Therefore, the poor immunogenicity of the extracellular domain of RYK including the WIF domain, combined with the constitutive cleavage of the extracellular domain have proved problematic in the generation of monoclonal antibodies to the RYK extracellular domain, in particular the WIF domain.

The term "antibody" refers to an immunoglobulin or fragment thereof, and encompasses any polypeptide comprising an antigen-binding fragment or an antigen binding domain. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')2, Fv, scFv, Fd, dAb, and other antibody fragments that retain antigen-binding function. Typically, such fragments would comprise an antigen-binding domain.

The terms "antigen-binding fragment" and "antigen-binding domain" refer to a part of an antibody molecule that comprises amino acids responsible for the specific binding between antibody and antigen. The part of the antigen that is specifically recognized and bound by the antibody is referred to as the "epitope." An antigen-binding domain may comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of antigen-binding fragments of an antibody include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) a Fd fragment having the two VH and CH1 domains; (4) a Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv). Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). These antibody fragments are obtained using conventional techniques known to those with skill in the art, and the fragments are evaluated for function in the same manner as are intact antibodies.

The term "human antibody" includes antibodies having variable and constant regions corresponding substantially to human germline immunoglobulin sequences known in the art, including, for example, those described by Kabat et al. (See Kabat, et al. (1991) *Sequences of Proteins of Immunological Interest*, Fifth Edition, U.S. Department of Health and Human Services, NIH Publication No. 913242). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The term "derivative" as used herein refers to a polypeptide that comprises an amino acid sequence of an antibody that specifically binds to a RYK polypeptide, or an antibody fragment that specifically binds to a RYK polypeptide, which has been altered by the introduction of amino acid residue substitutions, deletions or additions (i.e., mutations). In some embodiments, an antibody derivative or fragment thereof comprises amino acid residue substitutions, deletions or additions in one or more CDRs. The antibody derivative may have substantially the same binding, better binding, or worse binding when compared to a non-derivative antibody. In specific embodiments, one, two, three, four, or five amino acid residues of the CDR have been substituted, deleted or added (i.e., mutated). The term "derivative" as used herein also refers to an antibody that specifically binds to a RYK polypeptide, or an antibody fragment that specifically binds to a RYK polypeptide, which has been modified, i.e., by the covalent attachment of any type of molecule to the polypeptide. For example, but not by way of limitation, an antibody or an antibody fragment may be modified, such as by glycosylation, acetylation, pegylation, phosphorylation, amidation, derivatization by known protecting/blocking groups, proteolytic cleavage, linkage to a cellular ligand or other protein, etc. A derivative may also be modified by chemical modifications using techniques known to those of skill in the art, including, but not limited to specific chemical cleavage, acetylation, formylation, metabolic synthesis of tunicamycin, etc. Further, a derivative may contain one or more non-classical amino acids. In one embodiment, a derivative possesses a similar or identical function as an antibody, or antibody fragment described herein. In another embodiment, a derivative has an altered activity when compared to an unaltered polypeptide. For example, a derivative antibody or antibody fragment can bind to its epitope more tightly or be more resistant to proteolysis.

The "fragments" described herein include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, at least 250 contiguous amino acid residues, at least 300 contiguous amino acid residues, at least 350 contiguous amino acid residues, or at least 400 contiguous amino acid residues of the amino acid sequence of an antibody that specifically binds to the WIF domain of human RYK. That is, a "fragment" can include a peptide or polypeptide comprising an amino acid sequence of contiguous amino acid sequences having at least 35%, preferably at least 40%, at least 45%, at least 50%, at least 55%, at least 60%, at least 65%, at least 70%, at least 75%, at least 80%, at least 85%, at least 90%, at least 95%, or at least 99% identity with an antibody that specifically binds to the WIF domain of human RYK.

The terms "specific binding" or "specifically binds" refers to two molecules forming a complex that is relatively stable under physiologic conditions. Specific binding is characterized by a high affinity and a low to moderate capacity as distinguished from nonspecific binding which usually has a low affinity with a moderate to high capacity. If necessary, nonspecific binding can be reduced without substantially affecting specific binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques.

The present invention provides antibodies that specifically bind to the human RYK WIF domain, said antibodies comprising derivatives of the VH domains, VH CDRs, VL domains, or VL CDRs described herein that specifically bind to the human RYK WIF domain. Preferably, the antibodies of the present invention can modulate RYK function. More preferably, the antibodies can substantially modulate Wnt signaling, preferably, the antibodies can substantially modulate Wnt signaling mediated by Wnt5a.

As used herein, the term "modulate" or "modulating" refers to adjusting, changing, or manipulating, for example an increase or decrease, the amount, quality, response or effect of a particular activity, function or molecule. As used herein, the "inhibit" or "inhibition" or "inhibiting" variants thereof refer to decreasing, reducing, suppressing, blocking or preventing.

As used herein, the term "substantially" refers to the qualitative condition of exhibiting total or near-total extent or degree of a characteristic or property of interest. The skilled addressee will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The amino acid sequences describing the antibodies, or antigen-binding fragments or derivatives of the antibodies of the present invention are set forth in Table 1 below.

TABLE 1

Note: (*) has been substituted with a glutamine residue (Q)

| Sequence Identifier | Sequence | Seq ID No: |
|---|---|---|
| scFv3 | EVQLLESGGGLVQPGGSLRLSCAASGFTFSS YAMSWVRQAPGKGLEWVSLIHKAGHTT*YAD SVKGRFTISRDNSKNTLYLQMNSLRAEDTAV YYCAKGYRHFDYWGQGTLVTVSSGGGGSGG GSGGGGSTDIQMTQSPSSLSASVGDRVAITC RASQSISSYLNWYQQKPGKAPKLLIYRASNL QSGVPSRFSGSGSGTDFTLTISSLQPEDFAT YYCQQAVGSPRTFGQGTKVEIKR | SEQ ID No. 1 |
| scFv3 VH | EVQLLESGGGLVQPGGSLRLSCAASGFTFSS YAMSWVRQAPGKGLEWVSLIHKAGHTTQYAD SVKGRFTISRDNSKNTLYLQMNSLRAEDTAV YYCAKGYRHFDYWGQGTLVTVSS | SEQ ID No. 2 |
| scFv3 VL | DIQMTQSPSSLSASVGDRVAITCRASQSISS YLNWYQQKPGKAPKLLIYRASNLQSGVPSRF SGSGSGTDFTLTISSLQPEDFATYYCQQAVG SPRTFGQGTKVEIKR | SEQ ID No. 3 |
| scFv3 CDRH1 | SYAMS | SEQ ID No. 4 |
| scFv3 CDRH2 | LIHKAGHTTQYADSVKGV | SEQ ID No. 5 |
| scFv3 CDRH3 | GYRHFD | SEQ ID No. 6 |
| scFv3 CDRL1 | RASQSISSYLN | SEQ ID No. 7 |
| scFv3 CDRL2 | RASNLQSGVPS | SEQ ID No. 8 |
| scFv3 CDRL3 | AVGSPRT | SEQ ID No. 9 |
| scFvN3 | EVQLLESGGGLV*PGGSLRLSCAASGFTFSS YAMSWVRQAPGKGLEWVSTISRVGFPTVYAD SVKGRFTISRDNSKNTLYLQMNSLRAEDTAV YYCAKRGHPFDYVVGQGTLVTVSSGGGGSGG GGSGGGGSTDIQMTQSPSSLSASVGDRVTIT CRASQSISSYLNWYQQKPGKAPKLLIYQASV LQSGVPSRFSGSGSGTDFTLTISSLQPEDFA TYYCQQPGPAPPTFGQGTKVEIKR | SEQ ID No. 10 |
| scFvN3 VH | EVQLLESGGGLV*PGGSLRLSCAASGFTFSS YAMSWVRQAPGKGLEWVSTISRVGFPTVYAD SVKGRFTISRDNSKNTLYLQMNSLRAEDTAV YYCAKRGHPFDYWGQGTLVTVSSPGPAPPTF GQGTKVEIKR | SEQ ID No. 11 |
| scFvN3 VL | DIQMTQSPSSLSASVGDRVTITCRASQSISS YLNWYQQKPGKAPKLLIYQASVLQSGVPSRF | SEQ ID No. 12 |

TABLE 1-continued

Note: (*) has been substituted with a glutamine residue (Q)

| Sequence Identifier | Sequence | Seq ID No: |
|---|---|---|
| | SGSGSGTDFTLTISSLQPEDFATYYCQQPGP APPTFGQGTKVEIKR | |
| scFvN3 CDRH1 | SYAMS | SEQ ID No. 13 |
| scFvN3 CDRH2 | TISRVGFPT | SEQ ID No. 14 |
| scFvN3 CDRH3 | RGHPFD | SEQ ID No. 15 |
| scFvN3 CDRL1 | RASQSISSYLN | SEQ ID No. 16 |
| scFvN3 CDRL2 | QASVLQSGVPSRFS | SEQ ID No. 17 |
| scFvN3 CDRL3 | PGPAPPT | SEQ ID No. 18 |
| RWD1 Heavy Chain | EVQLLESGGGLVQPGGSLRLSCAASGFTFSS YAMSWVRQAPGKGLEWVSLIHKAGHTTQYAD SVKGRFTISRDNSKNTLYLQMNSLRAEDTAV YYCAKGYRHFDYWGQGTLVTVSSASTKGPSV FPLAPSSKSTSGGTAALGCLVKDYFPEPVTV SWNSGALTSGVHTFPAVLQSSGLYSLSSVVT VPSSSLGTQTYICNVNHKPSNTKVDKKVEPK SCDKTHTCPPCPAPELLGGPSVFLFPPKPKD TLMISRTPEVTCVVVDVSHEDPEVKFNWYVD GVEVHNAKTKPREEQYNSTYRVVSVLTVLHQ DWLNGKEYKCKVSNKALPAPIEKTISKAKGQ PREPQVYTLPPSREEMTKNQVSLTCLVKGFY PSDIAVEWESNGQPENNYKTTPPVLDSDGSF FLYSKLTVDKSRWQQGNVFSCSVMHEALHNH YTQKSLSLSPGK | SEQ ID No. 19 |
| RWD1 Light Chain | DIQMTQSPSSLSASVGDRVAITCRASQSISS YLNWYQQKPGKAPKLLIYRASNLQSGVPSRF SGSGSGTDFTLTISSLQPEDFATYYCQQAVG SPRTFGQGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSLPVTKSFNRGE | SEQ ID No. 20 |

In a further embodiment of the present invention, there is provided an isolated monoclonal antibody or antigen-binding fragment or derivative thereof, comprising a heavy chain comprising at least one complementarity determining region (CDR) chosen from the CDRs of sequence SEQ ID No. 4, 5, 6, 13, 14 or 15, or at least one CDR whose sequence has at least 80% identity after optimum alignment with the sequence SEQ ID No. 4, 5, 6, 13, 14 or 15, or in that it comprises a light chain comprising at least one CDR chosen from the CDRs of sequence SEQ ID No. 7, 8, 9, 16, 17, or 18, or at least one CDR whose sequence has at least 80% identity after optimum alignment with the sequence SEQ ID No. 7, 8, 9, 16, 17, or 18.

In a further embodiment of the present invention, there is provided an isolated monoclonal antibody or antigen-binding fragment or derivative thereof, comprising a heavy chain comprising at least two complementarity determining regions (CDR) chosen from the CDRs of sequence SEQ ID No. 4, 5, 6, 13, 14 or 15, or at least two CDRs whose sequence has at least 80% identity after optimum alignment with the sequence SEQ ID No. 4, 5, 6, 13, 14 or 15, or in that it comprises a light chain comprising at least two CDRs chosen from the CDRs of sequence SEQ ID No. 7, 8, 9, 16, 17, or 18, or at least two CDRs whose sequence has at least 80% identity after optimum alignment with the sequence SEQ ID No. 7, 8, 9, 16, 17, or 18.

In a further embodiment of the present invention, there is provided an isolated monoclonal antibody or antigen-binding fragment or derivative thereof, comprising a heavy chain comprising three complementarity determining regions (CDR) chosen from the CDRs of sequence SEQ ID No. 4, 5, 6, 13, 14 or 15, or three CDRs whose sequence has at least 80% identity after optimum alignment with the sequence SEQ ID No. 4, 5, 6, 13, 14 or 15, or in that it comprises a light chain comprising at least two CDRs chosen from the CDRs of sequence SEQ ID No. 7, 8, 9, 16, 17, or 18, or at least two CDRs whose sequence has at least 80% identity after optimum alignment with the sequence SEQ ID No. 7, 8, 9, 16, 17, or 18.

In a further embodiment of the present invention, there is provided an isolated monoclonal antibody or antigen-binding fragment or derivative thereof, comprising a heavy chain comprising two of the three or the three complementarity determining regions (CDR) chosen from the CDRs of sequence SEQ ID No. 4, 5, or 6, or two of the three or the three CDRs whose sequence has at least 80% identity after optimum alignment with the sequence SEQ ID No. 4, 5, or 6.

In a further embodiment of the present invention, there is provided an isolated monoclonal antibody or antigen-binding fragment or derivative thereof, comprising a light chain comprising two of the three or the three complementarity determining regions (CDR) chosen from the CDRs of sequence SEQ ID No. 7, 8, or 9, or two of the three or the three CDRs whose sequence has at least 80% identity after optimum alignment with the sequence SEQ ID No. 7, 8, or 9.

In a further embodiment of the present invention, there is provided an isolated monoclonal antibody or antigen-binding fragment or derivative thereof, comprising a heavy chain comprising two of the three or the three complementarity determining regions (CDR) chosen from the CDRs of sequence SEQ ID No. 13, 14 or 15, or two of the three or the three CDRs whose sequence has at least 80% identity after optimum alignment with the sequence SEQ ID No. 13, 14 or 15.

In a further embodiment of the present invention, there is provided an isolated monoclonal antibody or antigen-binding fragment or derivative thereof, comprising a light chain comprising two of the three or the three complementarity determining regions (CDR) chosen from the CDRs of sequence SEQ ID No. 16, 17, or 18, or two of the three or the three CDRs whose sequence has at least 80% identity after optimum alignment with the sequence SEQ ID No. 16, 17, or 18.

The phrase "percent (%) identical" or "percent (%) identity" refers to the similarity between at least two different sequences. This percent identity can be determined by standard alignment algorithms, for example, the Basic Local Alignment Tool (BLAST) described by Altshul et al. ((1990) *J. Mol. Biol.*, 215: 403-410); the algorithm of Needleman et al. ((1970) *J. Mol. Biol.*, 48: 444-453); or the algorithm of Meyers et al. ((1988) *Comput. Appl. Biosci.*, 4: 11-17). The percent identity is usually calculated by comparing sequences of similar length.

The phrase "substantially identical" or "substantially homologous" means that the relevant amino acid or nucleotide sequence (e.g., CDR(s), VH, or VL domain) will be identical to or have insubstantial differences (through conserved amino acid substitutions) in comparison to the sequences which are set out. Insubstantial differences include minor amino acid changes, such as 1 or 2 substitutions in a 5 amino acid sequence of a specified region. In the case of antibodies, the second antibody has the same specificity and has at least 50% of the affinity of the first antibody.

Sequences substantially identical or homologous (e.g., at least about 85% sequence identity) to the sequences disclosed herein are also part of this application. In some embodiments, the sequence identity can be about 85%, 90%, 95%, 96%, 97%, 98%, 99% or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

In another embodiment, the present invention also provides for antibodies comprising a variable heavy ("VH") domain and/or a variable light ("VL") domain having an amino acid sequence of the VH domain and/or VL domain, respectively, of scFv3 (SEQ ID No: 2 and 3, respectively), or scFvN3 (SEQ ID No: 11 and 12, respectively) or a VH/VL sequence whose sequence has at least 80% identity after optimum alignment with the sequence SEQ ID No. 2, 3, 11, or 12. These sequences represent unique scFv sequences identified from a naïve scFv phage library. Such antibodies may further comprise any constant region known in the art, preferably any human constant region known in the art, including, but not limited to, human light chain kappa (κ), human light chain lambda (λ), the constant region of $IgG_1$, the constant region of $IgG_2$, the constant region of $IgG_3$ or the constant region of $IgG_4$.

In a preferred embodiment, the present invention provides an antibody comprising a variable heavy ("VH") domain and/or a variable light ("VL") domain having an amino acid sequence of the VH domain and/or VL domain, respectively, of scFv3 (SEQ ID No: 2 and 3, respectively) or a VH/VL sequence whose sequence has at least 80% identity after optimum alignment with the sequence SEQ ID No. 2 or 3, grafted onto a human $IgG_1$ backbone.

In a preferred embodiment, the present invention provides an antibody, designated RWD1, having a heavy and or light chain encoded by the sequence SEQ ID No. 19 or 20 respectively, or a sequence whose sequence has at least 80% identity after optimum alignment with the sequence SEQ ID No. 19 or 20.

The antibody of the invention can be full-length (e.g., include at least one complete heavy chain and at least one complete light chain) or can include only an antigen-binding fragment (e.g., a Fab, F(ab')$_2$, Fv, a single chain Fv fragment, a Fd fragment, or a dAb fragment). The antibody can include a constant region, or a portion thereof, chosen from any of: the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. The light chain constant region can be chosen from kappa or lambda. The antibody may be an IgG, or it may also be $IgG_{1\kappa}$ or $IgG_{1\gamma}$.

The anti-RYK antibody described herein can be derivatized or linked to another functional molecule (such as another peptide or protein (e.g., a Fab fragment)). For example, an antibody of the invention can be functionally linked (e.g., by chemical coupling, genetic fusion, non-covalent association or otherwise) to at least one other molecular entity, such as another antibody (e.g., a bispecific or a multispecific antibody), toxin, radioisotope, cytotoxic or cytostatic agent, among others.

Standard techniques known to those of skill in the art can be used to introduce mutations (e.g., deletions, additions, and/or substitutions) in the nucleotide sequence encoding an antibody of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule.

In a further embodiment, the derivatives have conservative amino acid substitutions made at one or more predicted non-essential amino acid residues (i.e., amino acid residues which are not critical for the antibody to specifically bind to the human RYK WIF domain). A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody can be expressed and the activity of the antibody can be determined.

In a specific embodiment, the present invention provides an antibody that specifically binds to the human RYK WIF domain comprising an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of scFv3 (SEQ ID No: 1), scFvN3 (SEQ ID No: 10) or RWD1 (SEQ ID No's: 19 and 20), or an antigen-binding fragment thereof.

In another embodiment, the present invention provides an antibody that specifically binds to the human RYK WIF domain comprising an amino acid sequence of a VH domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the VH domain of scFv3 (SEQ ID No: 2), scFvN3 (SEQ ID No: 11) or RWD1 (SEQ ID No: 19).

In another embodiment, the present invention provides an antibody that specifically binds to the human RYK WIF domain comprising an amino acid sequence of a VL domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the VL domain of scFv3 (SEQ ID No: 3), scFvN3 (SEQ ID No: 12) or RWD1 (SEQ ID No: 20).

In another embodiment, the present invention provides an antibody that specifically binds to the human RYK WIF domain comprising an amino acid sequence of one or more VL CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs (SEQ ID No's: 7-9 and 16-18) listed in Table 1. In another embodiment, an antibody that specifically binds to the human RYK WIF domain comprises an amino acid sequence of one or more VH CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of one of the VH CDRs (SEQ ID No's: 4-6 and 13-15) listed in Table 1.

In another embodiment, the invention provides an antibody that specifically binds to the human RYK WIF domain, said antibody being encoded by a nucleotide sequence that is at least 65%, preferably at least 70%, at least 75%, at least 80%, at least 85%, at least 90%, at least 95%, or at least 99% identical to the nucleotide sequence encoding scFv3 (SEQ ID No: 21).

In another embodiment, the invention provides an antibody that specifically binds to the human RYK WIF domain, said antibody comprising a VH domain and/or VL domain encoded by a nucleotide sequence that is at least 65%, preferably at least 70%, at least 75%, at least 80%, at least 85%, at least 90%, at least 95%, or at least 99% identical to the nucleotide sequence encoding the VH domain and/or VL domain of scFv3 (SEQ ID No's: 22 and 23).

In another embodiment, the invention provides an antibody that specifically binds to the human RYK WIF domain, said antibody comprising a VH CDR and/or a VL CDR encoded by a nucleotide sequence that is at least 65%, preferably at least 70%, at least 75%, at least 80%, at least 85%, at least 90%, at least 95%, or at least 99% identical to the nucleotide sequence encoding the VH CDRs (SEQ ID No's: 24-26) and/or VL CDRs (SEQ ID No's: 27-29) of scFv3.

In another embodiment, the invention provides an antibody that specifically binds to the human RYK WIF domain, said antibody encoded by a nucleotide sequence that is at least 65%, preferably at least 70%, at least 75%, at least 80%, at least 85%, at least 90%, at least 95%, or at least 99% identical to the nucleotide sequence encoding scFvN3 (SEQ ID No: 30).

In another embodiment, the invention provides an antibody that specifically binds to the human RYK WIF domain, said antibody comprising a VH domain and/or VL domain encoded by a nucleotide sequence that is at least 65%, preferably at least 70%, at least 75%, at least 80%, at least 85%, at least 90%, at least 95%, or at least 99% identical to the nucleotide sequence encoding the VH domain and/or VL domain of scFvN3 (SEQ ID No's: 31 and 32).

In another embodiment, the invention provides an antibody that specifically binds to the human RYK WIF domain, said antibody comprising a VH CDR and/or a VL CDR encoded by a nucleotide sequence that is at least 65%, preferably at least 70%, at least 75%, at least 80%, at least 85%, at least 90%, at least 95%, or at least 99% identical to the nucleotide sequence encoding the VH CDRs (SEQ ID No's: 33-35) and/or VL CDRs (SEQ ID No's: 36-38) of scFvN3.

In a specific embodiment, an antibody that specifically binds to the human RYK WIF domain is encoded by a nucleotide sequence that hybridizes to the nucleotide sequence encoding scFv3 (SEQ ID No: 21), scFvN3 (SEQ ID No: 30) or RWD1 (SEQ ID Nos: 39 and 40), or an antigen-binding fragment or derivative thereof, under stringent conditions (e.g., hybridization to filter-bound DNA in 6× sodium chloride/sodium citrate (SSC) at about 45° C., followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M., et al., eds., 1989, *Current Protocols in Molecular Biology*, Vol. 1, Green Publishing Associates, Inc. and John Wiley & Sons, Inc., New York at pages 6.3.1-6.3.6 and 2.10.3).

In another aspect, the present invention provides antibodies that compete with and/or substantially inhibit the interaction of RYK with Wnt proteins. The competition/inhibition of the interaction of RYK with Wnt proteins is associated with an inhibition of Wnt signaling. Accordingly, binding of an antibody of the present invention is associated with a modulation of RYK-mediated signal transduction. In an embodiment, the present invention provides an antibody that competes with and/or substantially inhibits the interaction of RYK with Wnt proteins.

In a preferred embodiment, the present invention provides an antibody that competes with and/or substantially inhibits the interaction of RYK with Wnt5a.

The present invention provides for antibodies that have a high binding affinity for human RYK WIF domain. In the determination of the binding affinity of an antibody such as by surface plasmon resonance imaging (SPRi) analysis, the person skilled in the art would understand that specific values determined for rates of association or dissociation of an antibody with its target may be altered by variations made to the conditions of the assay.

Such conditions include but are not limited to the temperature at which an assay is performed and the strength or pH of buffers and other solutions used for the assay.

In a specific embodiment, an antibody that specifically binds to the human RYK WIF domain has an association rate constant of at least $10^3$ $M^{-1}$ $s^{-1}$, at least $1.5 \times 10^3$ $M^{-1}$ $s^{-1}$, at least $2 \times 10^3$ $M^{-1}$ $s^{-1}$, at least $2.5 \times 10^3$ $M^{-1}$ $s^{-1}$, at least $5 \times 10^3$ $M^{-1}$ $s^{-1}$, at least $10^4$ $M^{-1}$ $s^{-1}$ or at least $5 \times 10^4$ $M^{-1}$ $s^{-1}$ as determined by SPRi analysis.

In a preferred embodiment, the present invention provides an antibody that specifically binds to the human RYK WIF domain has an association rate constant of at least about $8.8 \times 10^4$ $M^{-1}$ $s^{-1}$ as determined by surface plasmon resonance imaging (SPRi) analysis.

In another embodiment, an antibody that specifically binds to the human RYK WIF domain has an association rate constant of at most $10^8$ $M^{-1}$ $s^{-1}$, at most $10^9$ $M^{-1}$ $s^{-1}$, at most $10^{10}$ $M^{-1}$ $s^{-1}$, at most $10^{11}$ $M^{-1}$ $s^{-1}$, or at most $10^{12}$ $M^{-1}$ $s^{-1}$ as determined by SPRi analysis. In accordance with these embodiments, such antibodies may comprise a VH domain and/or a VL domain of scFv3, or scFvN3, or the heavy and/or light chains of RWD1.

In another embodiment, an antibody that specifically binds to the human RYK WIF domain has a dissociation rate constant of less than less than $5 \times 10^4$ $s^{-1}$, less than $10^{-3}$ $s^{-1}$, less than $5 \times 10^{-3}$ $s^{-1}$, less than $10^{-2}$ $s^{-1}$, less than $5 \times 10^{-2}$ $s^{-1}$, less than $10^{-1}$ $s^{-1}$, or less than $5 \times 10^{-1}$ $s^{-1}$, or $10^{-1}$-$10^{-5}$ $s^{-1}$, $10^{-3}$-$10^{-5}$ $s^{-1}$, or $10^{-3}$-$10^{-4}$ $s^{-1}$ as determined by SPRi analysis.

In a preferred embodiment, the present invention provides an antibody that specifically binds to the human RYK WIF domain has a dissociation rate constant of about $3.7 \times 10^{-4}$ $s^{-1}$ as determined by SPRi analysis.

In another embodiment, an antibody that specifically binds to the human RYK WIF domain has a dissociation rate constant of greater than $10^{-13}$ s$^{-1}$, greater than $10^{-12}$ s$^{-1}$, greater than $10^{-11}$ s$^{-1}$, greater than $10^{-10}$ s$^{-1}$, greater than $10^{-9}$ s$^{-1}$, or greater than $10^{-8}$ s$^{-1}$ as determined by SPRi analysis. In accordance with these embodiments, such antibodies may comprise a VH domain and/or a VL domain of scFv3, or scFvN3 or the heavy and/or light chains of RWD1.

In another embodiment, an antibody that specifically binds to the human RYK WIF domain has a dissociation constant or $K_D$ ($k_a/k_d$) of less than $5\times10^{-9}$ M, less than $10^{-8}$ M, less than $5\times10^{-8}$ M, less than $10^{-7}$ M, less than $5\times10^{-7}$ M, less than $10^{-6}$ M, less than $5\times10^{-6}$ M, less than $10^{-5}$ M, less than $5\times10^{-5}$ M, less than $10^{-4}$ M, less than $5\times10^{-4}$ M, less than $10^{-3}$ M, or less than $5\times10^{-3}$ M or $10^{-2}$ M-$5\times10^{-5}$ M, or $10^{-6}$-$10^{-8}$ M as determined by SPRi analysis.

In a preferred embodiment, the present invention provides an antibody that specifically binds to the human RYK WIF domain with a $K_D$ of about $4.2\times10^{-9}$ M as determined by SPRi analysis.

In another embodiment, an antibody that specifically binds to the human RYK WIF domain has a $K_D$ of greater than $10^{-9}$ M, greater than $5\times10^{-10}$ M, greater than $10^{-10}$ M, greater than $5\times10^{-11}$ M, greater than $10^{-11}$ M, greater than $5\times10^{-12}$ M, greater than $10^{-12}$ M, greater than $5\times10^{-13}$ M, greater than $10^{-13}$ M, greater than $5\times10^{-14}$ M, greater than $10^{-14}$ M or greater than $10^{-9}$ M-$10^{-14}$ M. In accordance with these embodiments, such antibodies may comprise a VH domain and/or a VL domain of scFv3, or scFvN3, or the heavy and/or light chains of RWD1.

Although the embodiments illustrated in the Examples comprise a "matching" pair of VH and VL domains, a skilled artisan will recognize that alternative embodiments may comprise antigen-binding fragments containing only a single CDR from either VL or VH domain. Either one of the single chain specific antigen-binding domains can be used to screen for complementary domains capable of forming a two-domain specific antigen-binding fragment capable of, for example, binding to the human RYK WIF domain. The screening may be accomplished by phage display screening methods known to those in the art. In this approach, an individual colony containing either a H or L chain clone is used to infect a complete library of clones encoding the other chain (L or H), and the resulting two-chain specific antigen-binding domain is selected in accordance with phage display techniques as described.

In some alternative embodiments, the anti-RYK antibodies can be linked to a protein (e.g., albumin) by chemical cross-linking or recombinant methods. The disclosed antibodies may also be linked to a variety of nonproteinaceous polymers (e.g., polyethylene glycol, polypropylene glycol, or polyoxyalkylenes). The antibodies can be chemically modified by covalent conjugation to a polymer, for example, to increase their half-life in blood circulation.

The disclosed antibodies can be modified to alter their glycosylation; that is, at least one carbohydrate moiety can be deleted or added to the antibody. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the antibody. Removal of carbohydrate moieties can also be accomplished chemically or enzymatically.

Methods for altering an antibody constant region are known in the art. Antibodies with altered function (e.g., altered affinity for an effector ligand such as FcR on a cell or the C1 component of complement) can be produced by replacing at least one amino acid residue in the constant portion of the antibody with a different residue. Similar types of alterations could be described which if applied to a murine or other species antibody would reduce or eliminate similar functions.

For example, it is possible to alter the affinity of an Fc region of an antibody (e.g., an IgG, such as a human IgG) for FcR (e.g., Fc gamma R1). The affinity may be altered by replacing at least one specified residue with at least one residue having an appropriate functionality on its side chain, or by introducing a charged functional group, such as glutamate or aspartate, or perhaps an aromatic non-polar residue such as phenylalanine, tryptophan or tyrosine.

Modified antibodies can be produced which have a reduced interaction with an Fc receptor. For example, it has been shown that in human IgG3, which binds to the human Fc gamma R1 receptor, changing Leu 235 to Glu destroys its interaction with the receptor. Mutations on adjacent or close sites in the hinge link region of an antibody (e.g., replacing residues 234, 236 or 237 with Ala) can also be used to affect antibody affinity for the Fc gamma R1 receptor.

Additional methods for altering the lytic activity of an antibody, for example, by altering at least one amino acid in the N-terminal region of the CH2 domain, are also known in the art.

The antibodies of this invention may be tagged with a detectable or functional label. These labels include radiolabels (e.g., $^{131}$I or $^{99}$Tc), enzymatic labels (e.g., horseradish peroxidase or alkaline phosphatase), and other chemical moieties (e.g., biotin).

In another aspect, the invention features a pharmaceutical composition containing at least one human anti-RYK antibody and a pharmaceutically acceptable carrier. In a preferred embodiment, the pharmaceutical composition can further include a combination of at least one anti-RYK antibody and at least one therapeutic agent selected from the group comprising cytokines and growth factor inhibitors, immunosuppressants, anti-inflammatory agents, metabolic inhibitors, enzyme inhibitors, cytotoxic agents, cytostatic agents, or combinations thereof.

The present invention provides peptides, polypeptides and/or proteins comprising one or more variable or hypervariable regions of the antibodies described herein. Preferably, peptides, polypeptides or proteins comprising one or more variable or hypervariable regions of antibodies of the invention further comprise a heterologous amino acid sequence. In certain embodiments, such a heterologous amino acid sequence comprises at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 75 contiguous amino acid residues, at least 100 contiguous amino acid residues or more contiguous amino acid residues. Such peptides, polypeptides and/or proteins may be referred to as fusion proteins.

In a specific embodiment, peptides, polypeptides or proteins comprising one or more variable or hypervariable regions of the antibodies of the invention are 10 amino acid residues, 15 amino acid residues, 20 amino acid residues, 25 amino acid residues, 30 amino acid residues, 35 amino acid residues, 40 amino acid residues, 45 amino acid residues, 50 amino acid residues, 75 amino acid residues, 100 amino acid residues, 125 amino acid residues, 150 amino acid residues or more amino acid residues in length. In certain embodiments, peptides, polypeptides, or proteins comprising one or more variable or hypervariable regions of an antibody of the invention specifically bind to the human RYK WIF domain.

In certain embodiments, peptides, polypeptides or proteins comprising one or more variable or hypervariable regions of the antibodies of the invention are a heterologous amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical with a hypervariable region of an antibody of the invention.

In a specific embodiment, the present invention provides peptides, polypeptides and/or proteins comprising a VH domain and/or VL domain of one of the antibodies described herein (see Table 1). In another embodiment, the present invention provides peptides, polypeptides and/or proteins comprising one or more CDRs having the amino acid sequence of any of the CDRs listed in Table 1. In accordance with these embodiments, the peptides, polypeptides or proteins may further comprise a heterologous amino acid sequence.

Peptides, polypeptides or proteins comprising one or more variable or hypervariable regions have utility, e.g., in the production of anti-idiotypic antibodies which in turn may be used to prevent, treat, and/or ameliorate one or more symptoms associated with a condition, disease or disorder (e.g., cancer). The anti-idiotypic antibodies produced can also be utilized in immunoassays, such as, e.g., ELISAs, for the detection of antibodies which comprise a variable or hypervariable region contained in the peptide, polypeptide or protein used in the production of the anti-idiotypic antibodies.

According to another aspect, the invention relates to mammalian cells capable of secreting monoclonal antibodies according to the present invention, especially anti-RYK IgG/CHO cells such as deposited by Applicants under the terms of the Budapest Treaty with the International Strain Depositary CellBank Australia (CBA) 214 Hawkesbury Rd, Westmead, NSW Australia, 2145, on 1 Mar. 2013 and having the accession number CBA20130025.

In another aspect, the present invention provides polynucleotides that hybridize under high stringency, intermediate or lower stringency hybridization conditions, to polynucleotides that encode an antibody of the invention. In a specific embodiment, the invention provides a nucleic acid comprising a nucleotide sequence encoding 1, 2 or 3 CDRs of the heavy chain variable domain or a light chain variable domain of an antibody of the invention.

In a specific embodiment, the invention provides an isolated nucleic acid comprising a nucleotide sequence encoding a heavy chain variable domain and/or a light chain variable domain of an antibody of the invention (e.g., scFv3 or scFvN3; Seq ID No's: 1 and 10, respectively).

In another specific embodiment, the invention provides an isolated nucleic acid comprising a nucleotide sequence encoding a heavy chain variable domain and/or a light chain variable domain of an antibody of the invention (e.g., scFv3 or scFvN3; Seq ID No's: 3 and 12, respectively) that has been humanized or chimerized.

In another embodiment, the invention provides an isolated nucleic acid comprising a nucleotide sequence encoding a heavy chain or a light chain of an antibody of the invention (e.g., RWD1, Seq ID No. 19 and 20, respectively).

As used herein, the term "stringent" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and non-aqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5 M sodium phosphate, 7% SDS at 65° C., followed by at least one wash at 0.2×SSC, 1% SDS at 65° C.

The polynucleotides may be obtained, and the nucleotide sequence of the polynucleotides determined, by any method known in the art. Since the amino acid sequences of the antibodies have been determined by the inventors, nucleotide sequences encoding these antibodies can be determined using methods well known in the art, i.e., nucleotide codons known to encode particular amino acids are assembled in such a way to generate a nucleic acid that encodes the antibody or fragment thereof of the invention. Such a polynucleotide encoding the antibody may be assembled from chemically synthesized oligonucleotides (e.g., as described in Kutmeier et al., 1994, *BioTechniques* 17:242), which, briefly, involves the synthesis of overlapping oligonucleotides containing portions of the sequence encoding the antibody, annealing and ligating those oligonucleotides, and then amplification of the ligated oligonucleotides by PCR.

Alternatively, a polynucleotide encoding an antibody may be generated from a nucleic acid from a suitable source. If a clone containing a nucleic acid encoding a particular antibody is not available, but the sequence of the antibody molecule is known, (see e.g., FIGS. 7-10), a nucleic acid encoding the immunoglobulin may be chemically synthesized or obtained from a suitable source (e.g., an antibody cDNA library, or a cDNA library generated from nucleic acid, preferably poly A+ RNA, isolated from any tissue or cells expressing the antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2nd Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs of the present invention is inserted within framework regions using routine recombinant DNA techniques. The framework regions may be naturally occurring or consensus framework regions, and preferably human framework regions. Preferably, the polynucleotide generated by the combination of the framework regions and CDRs encodes an antibody that specifically binds to the human RYK WIF domain. Preferably, as discussed above, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Recombinant expression of an antibody of the invention, derivative, analog or fragment thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In further embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *BioTechnology* 8:2). In a specific embodiment, the expression of nucleotide sequences encoding antibodies or fragments thereof which specifically bind to the human RYK WIF domain is regulated by a constitutive promoter, inducible promoter or tissue specific promoter.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO* 12:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, *Methods in Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, BT483, Hs578T, HTB2, BT2O, NS1, and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transfected with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, *Cell* 11:223), glutamine synthase, hypoxanthine guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:8-17) genes can be employed in tk-, gs-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Wu and Wu, 1991, *Biotherapy* 3:87; Tolstoshev, 1993, *Ann. Rev. Pharmacol. Toxicol.* 32:573; Mulligan, 1993, *Science* 260: 926; and Morgan and Anderson, 1993, *Ann. Rev. Biochem.* 62: 191; May, 1993, *TIB TECH* 11:155-); and hygro, which confers resistance to hygromycin (Santerre et al., 1984, *Gene* 30:147). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds), *Current Protocols in Human Genetics*, John Wiley & Sons, NY (1994); Colberre-Garapin et al., 1981, *J. Mol. Biol.* 150:1, which are incorporated by reference herein in their entireties.

The expression levels of an antibody molecule can be increased by vector amplification. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature* 322:52; and Kohler, 1980, *Proc. Natl. Acad. Sci. USA* 77:2197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

The present invention encompasses methods for treating, preventing, or managing a condition, disease or disorder associated with RYK, preferably peripheral nerve or spinal cord injury or cancer, in a subject comprising administering one or more anti-RYK antibodies In general, increased RYK expression is associated with various cancers. Accordingly, detection of aberrant expression of RYK, or a reduction in RYK expression with a particular treatment indicates the presence of cancer or that the treatment is reducing the cancer, respectively. In a specific embodiment, the disorder to be treated, prevented, or managed is malignant cancer. In another specific embodiment, the disorder to be treated, prevented, or managed is a pre-cancerous condition associated with cells that overexpress RYK.

As used herein, the terms "therapeutic agent" and "therapeutic agents" refer to any substance(s) that treats or assists in treating a medical condition or disorder. In certain embodiments, the term "therapeutic agent" refers to an anti-RYK antibody. In certain other embodiments, the terms "therapeutic agent" and "therapeutic agents" refer to cancer chemotherapeutics, radiation therapy, hormonal therapy, and biological therapy/immunotherapy. In other embodiments, more than one therapeutic agent may be administered in combination.

As used herein, a "therapeutically effective amount" of an anti-RYK antibody refers to an amount of an antibody which is effective, upon single or multiple dose administration to a subject (such as a human patient) at treating, preventing, curing, delaying, reducing the severity of, and/or modulating at least one symptom of a condition, disease or disorder, or prolonging the survival of the subject beyond that expected in the absence of such treatment. As a non-limiting example, the term "effective amount" refers to a dosage or amount that is sufficient to regulate RYK activity to modulate clinical symptoms, e.g. improved recovery following nerve injury or improved prognosis or survival in cancer, or to achieve a desired biological outcome, e.g. such as through decreased neurite outgrowth and decreased axon retraction, decreased cellular proliferation or suppression of tumor growth, etc.

As used herein, the terms "treat," "treating" and "treatment" refer to the eradication, reduction or amelioration of symptoms of a condition, disease or disorder. As used herein, the term "amelioration" means that signs or symptoms associated with the condition, disease or disorder are lessened. In certain embodiments, such terms refer to the minimizing or delaying the spread of cancer or the eradication, removal, modification or control of cancer resulting from the administration of one or more therapeutic agents to a subject with such a disease.

As used herein, the terms "prevent," "preventing" and "prevention" refer to the prevention of the occurrence, recurrence or spread of a condition, disease or disorder in a subject resulting from the administration of a prophylactic or therapeutic agent.

As used herein, the term "in combination" refers to the use of more than one prophylactic and/or therapeutic agent. The use of the term "in combination" does not restrict the order in which prophylactic and/or therapeutic agents are administered to a subject. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

As used herein, the term "RYK-associated activity" refers to a function performed by RYK including the ability of RYK to specifically bind to or otherwise modulate Wnt, and/or Frizzled, and/or Dishevelled. The term "RYK-associated activity" also refers to a function performed by RYK that is associated with other Wnt pathways not involving Frizzled and a function performed by RYK that is independent of Wnt proteins. Accordingly, an agent that modulates RYK-associated activity will also modulate RYK mediated signal transduction activity (e.g., reduce or inhibit). As used herein, the term "RYK mediated signal transduction activity" refers to the signaling pathway that is initiated by the binding of Wnt to RYK or to RYK and Frizzled, is transmitted via Dishevelled, and ends in expression of one or more genes (e.g., TCF) or the activation of one or more proteins (e.g. RhoA).

The phrase "inhibit" or "antagonize" RYK-associated activity and its cognates refer to a reduction, inhibition, or otherwise diminution of at least one activity of RYK due to binding an anti-RYK antibody, wherein the reduction is relative to the activity of RYK in the absence of the same antibody. The activity can be measured using any technique known in the art, including, for example, as described in Example 6. Inhibition or antagonism does not necessarily indicate a total elimination of the biological activity of RYK. A reduction in activity may be about 10%, 20%, 30%, 40%, 50%, 60%, 70%, 80%, 90%, or more.

As used herein the term "RYK-associated condition" refers to a physiological or pathophysiological state where expression or overexpression of RYK in a cell or tissue leads to increased RYK mediated signal transduction and consequent gene expression. Such gene expression can result in increased cellular growth and/or proliferation and/or differentiation. As a non-limiting example, a RYK-associated condition can be cancer. In a further non-limiting example, a RYK-associated condition can be peripheral nerve or spinal cord injury.

As used herein, the term "cancer" refers to a disease involving cells that have the potential to metastasize to distal sites and exhibit phenotypic traits that differ from those of non-cancer cells. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

In one embodiment, the antibodies of the invention can be administered in combination with one or more other therapeutic or prophylactic agents useful in the treatment, prevention or management of cancer. In certain embodiments, one or more anti-RYK antibodies of the invention are administered to a mammal, preferably a human, concurrently with one or more other therapeutic agents useful for the treatment of a condition, disease or disorder associated with RYK, The term "concurrently" is not limited to the administration of prophylactic or therapeutic agents at exactly the same time, but rather it is meant that the anti-RYK antibodies of the invention and the other agent are administered to a subject in a sequence and within a time interval such that the antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In other embodiments, the anti-RYK antibodies of the invention are administered before, concurrently or after surgery. Preferably the surgery completely removes localized tumors or reduces the size of large tumors. Surgery can also be done as a preventive measure or to relieve pain.

As used herein, the terms "prophylactic agent" and "prophylactic agents" refer to any agent(s) that can be used in the prevention of the onset, recurrence or spread of a disorder associated with RYK overexpression, particularly cancer. In certain embodiments, the term "prophylactic agent" refers to anti-RYK antibody. In certain other embodiments, the terms "prophylactic agent" and "prophylactic agents" refer to cancer chemotherapeutics, radiation therapy, hormonal therapy, biological therapy (e.g., immunotherapy), and/or anti-RYK antibodies of the invention. In other embodiments, more than one prophylactic agent may be administered in combination.

In one embodiment, the one or more anti-RYK antibodies of the invention comprise scFv3, scFvN3, or RWD1. In other embodiments, variants of scFv3, scFvN3, or RWD1, e.g., with one or more amino acid substitutions, particularly in the variable domain, are provided that have increased activity, binding ability, etc., as compared to scFv3, scFvN3, or RWD1.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In further embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physicians' Desk Reference* (58$^{th}$ ed., 2004).

The invention provides methods for treating, preventing, and managing a condition, disease or disorder by administering to a subject a therapeutically or prophylactically effective amount of one or more anti-RYK antibodies of the invention. In another embodiment, the anti-RYK antibodies of the invention can be administered in combination with one or more other therapeutic agents. The subject is preferably a mammal such as non-primate (e.g., cows, pigs, horses, cats, dogs, rats, etc.) and a primate (e.g., monkey, such as a cynomolgous monkey and a human). In a further embodiment, the subject is a human.

Specific examples of cancers that can be treated by the methods encompassed by the invention include, but are not limited to, cancers that overexpress RYK. In a further embodiment, the cancer is of an epithelial origin. Examples of such cancers are selected from the group comprising cancer of the lung, colon, prostate, breast, and skin. In particular embodiments, methods of the invention can be used to treat and/or prevent metastasis from primary tumors.

The methods and compositions of the invention comprise the administration of one or more anti-RYK antibodies of the invention to subjects/patients suffering from or expected to suffer from cancer, e.g., have a genetic predisposition for a particular type of cancer, have been exposed to a carcinogen, or are in remission from a particular cancer. As used herein, "cancer" refers to primary or metastatic cancers. Such patients may or may not have been previously treated for cancer. The methods and compositions of the invention may be used as a first line or second line cancer treatment. Included in the invention is also the treatment of patients undergoing other cancer therapies and the methods and compositions of the invention can be used before any adverse effects or intolerance of these other cancer therapies occurs. The invention also encompasses methods for administering one or more anti-RYK antibodies of the invention to treat or ameliorate symptoms in refractory patients. In a certain embodiment, that a cancer is refractory to a therapy means that at least some significant portion of the cancer cells are not killed or their cell division arrested. The determination of whether the cancer cells are refractory can be made either in vivo or in vitro by any method known in the art for assaying the effectiveness of treatment on cancer cells, using the art-accepted meanings of "refractory" in such a context. In various embodiments, a cancer is refractory where the number of cancer cells has not been significantly reduced, or has increased. The invention also encompasses methods for administering one or more anti-RYK antibodies to prevent the onset or recurrence of cancer in patients predisposed to having cancer. In one embodiment, the monoclonal antibody is scFv3, scFvN3, or RWD1.

In particular embodiments, the anti-RYK antibodies of the invention, or other therapeutics that reduce RYK expression, are administered to reverse resistance or reduce sensitivity of cancer cells to certain hormonal, radiation and chemotherapeutic agents thereby resensitizing the cancer cells to one or more of these agents, which can then be administered (or continue to be administered) to treat or manage cancer, including to prevent metastasis.

In alternate embodiments, the invention provides methods for treating patients' cancer by administering one or more anti-RYK antibodies of the invention in combination with any other treatment or to patients who have proven refractory to other treatments but are no longer on these treatments. In one embodiment, the anti-RYK antibody is scFv3, scFvN3, or RWD1. In certain embodiments, the patients being treated by the methods of the invention are patients already being treated with chemotherapy, radiation therapy, hormonal therapy, or biological therapy/immunotherapy. Among these patients are refractory patients and those with cancer despite treatment with existing cancer therapies. In other embodiments, the patients have been treated and have no disease activity and one or more antibodies of the invention are administered to prevent the recurrence of cancer.

In certain embodiments, the existing treatment is chemotherapy. In particular embodiments, the existing treatment includes administration of chemotherapies including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbazine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, etc. Among these patients are patients treated with radiation therapy, hormonal therapy and/or biological therapy/immunotherapy. Also among these patients are those who have undergone surgery for the treatment of cancer.

Alternatively, the invention also encompasses methods for treating patients undergoing or having undergone radiation therapy. Among these are patients being treated or previously treated with chemotherapy, hormonal therapy and/or biological therapy/immunotherapy. Also among these patients are those who have undergone surgery for the treatment of cancer.

In other embodiments, the invention encompasses methods for treating patients undergoing or having undergone hormonal therapy and/or biological therapy/immunotherapy. Among these are patients being treated or having been treated with chemotherapy and/or radiation therapy. Also among these patients are those who have undergone surgery for the treatment of cancer.

Additionally, the invention also provides methods of treatment of cancer as an alternative to chemotherapy, radiation therapy, hormonal therapy, and/or biological therapy/immunotherapy where the therapy has proven or may prove too toxic, i.e., results in unacceptable or unbearable side effects, for the subject being treated. The subject being treated with the methods of the invention may, optionally, be treated with other cancer treatments such as surgery, chemotherapy, radiation therapy, hormonal therapy or biological therapy, depending on which treatment was found to be unacceptable or unbearable.

In other embodiments, the invention provides administration of one or more monoclonal antibodies of the invention without any other cancer therapies for the treatment of cancer, but who have proved refractory to such treatments. In specific embodiments, patients refractory to other cancer therapies are administered one or more monoclonal antibodies in the absence of cancer therapies.

Cancers and related disorders that can be treated or prevented by methods and compositions of the present invention include but are not limited to cancers of an epithelial cell origin. Examples of such cancers include the following: bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; ovarian cancers such as but not limited to, ovarian epithelial carcinoma, borderline tumor, germ cell tumor, and stromal tumor; In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

It is also contemplated that cancers caused by aberrations in apoptosis would also be treated by the methods and compositions of the invention. Such cancers may include but are not be limited to carcinomas with p53 mutations, hormone-dependent tumors of the ovary. In specific embodiments, malignancy or dysproliferative changes (such as metaplasias and dysplasias), or hyperproliferative disorders, are treated or prevented in the bone and connective tissue, brain or ovary.

In some embodiments, the cancer is malignant and overexpresses RYK. In other embodiments, the disorder to be treated is a pre-cancerous condition associated with cells that overexpress RYK.

In preferred embodiment, the present invention provides methods and compositions for the treatment and/or prevention of ovarian, brain or bone cancer.

In some embodiments, therapy by administration of one or more monoclonal antibodies is combined with the administration of one or more therapies such as, but not limited to, chemotherapies, radiation therapies, hormonal therapies, and/or biological therapies/immunotherapies. Prophylactic/therapeutic agents include, but are not limited to, proteinaceous molecules, including, but not limited to, peptides, polypeptides, proteins, including post-translationally modified proteins, antibodies etc.; or small molecules (less than 1000 daltons), inorganic or organic compounds; or nucleic acid molecules including, but not limited to, double-stranded or single-stranded DNA, or double-stranded or single-stranded RNA, as well as triple helix nucleic acid molecules. Prophylactic/therapeutic agents can be derived from any known organism (including, but not limited to, animals, plants, bacteria, fungi, and protista, or viruses) or from a library of synthetic molecules.

In a specific embodiment, the methods of the invention encompass administration of an antibody of the invention in combination with the administration of one or more prophylactic/therapeutic agents that are inhibitors of kinases such as, but not limited to, ABL, ACK, AFK, AKT (e.g., AKT-1, AKT-2, and AKT-3), ALK, AMP-PK, ATM, Aurora1, Aurora2, bARK1, bArk2, BLK, BMX, BTK, CAK, CaM kinase, CDC2, CDK, CK, COT, CTD, DNA-PK, EGF-R, ErbB-1, ErbB-2, ErbB-3, ErbB-4, ERK (e.g., ERK1, ERK2, ERK3, ERK4, ERK5, ERK6, ERK7), ERT-PK, FAK, FGR (e.g., FGF1R, FGF2R), FLT (e.g., FLT-1, FLT-2, FLT-3, FLT-4), FRK, FYN, GSK (e.g., GSK1, GSK2, GSK3-alpha, GSK3-beta, GSK4, GSK5), G-protein coupled receptor kinases (GRKs), HCK, HER2, HKII, JAK (e.g., JAK1, JAK2, JAK3, JAK4), JNK (e.g., JNK1, JNK2, JNK3), KDR, KIT, IGF-1 receptor, IKK-1, IKK-2, INSR (insulin receptor), IRAK1, IRAK2, IRK, ITK, LCK, LOK, LYN, MAPK, MAPKAPK-1, MAPKAPK-2, MEK, MET, MFPK, MHCK, MLCK, MLK3, NEU, NIK, PDGF receptor alpha, PDGF receptor beta, PHK, PI-3 kinase, PKA, PKB, PKC, PKG, PRK1, PYK2, p38 kinases, p135tyk2, p34cdc2, p42cdc2, p42mapk, p44mpk, RAF, RET, RIP, RIP-2, RK, RON, RS kinase, SRC, SYK, S6K, TAK1, TEC, TIE1, TIE2, TRKA, TXK, TYK2, UL13, VEGFR1, VEGFR2, YES, YRK, ZAP-70, and all subtypes of these kinases (see e.g., Hardie and Hanks (1995) The Protein Kinase Facts Book, I and II, Academic Press, San Diego, Calif.).

In further embodiments, an antibody of the invention is administered in combination with the administration of one or more prophylactic/therapeutic agents that are inhibitors of RYK or other RTKs, or inhibitors of Wnt signaling. In yet another embodiment, an antibody of the invention is administered in combination with the administration of one or more prophylactic/therapeutic agents that are inhibitors of RYK.

In another specific embodiment, the methods of the invention encompass administration of an antibody of the invention in combination with the administration of one or more prophylactic/therapeutic agents that are angiogenesis inhibitors such as, but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); fibronectin fragment; Gro-beta; Halofuginone; heparinases; heparin hexasaccharide fragment; HMV833; human chorionic gonadotropin (hCG); IM-862; interferon alpha/beta/gamma; interferon inducible protein (IP-10); interleukin-12; kringle 5 (plasminogen fragment); Marimastat; metalloproteinase inhibitors (TIMPs); 2-methoxyestradiol; MMI 270 (CGS 27023A); MoAb IMC-1C11; Neovastat; NM-3; Panzem; PI-88; placental ribonuclease inhibitor; plasminogen activator inhibitor; platelet factor-4 (PF4); Prinomastat; prolactin 16 kD fragment; proliferin-related protein (PRP); PTK 787/ZK 222594; retinoids; Solimastat; Squalamine; SS3304; SU5416; SU6668; SU11248; tetrahydrocortisol-S; tetrathiomolybdate; thalidomide; thrombospondin-1 (TSP-1); TNP-470; transforming growth factor-beta (TGF-β); Vasculostatin; Vasostatin (calreticulin fragment); ZD6126; ZD6474; farnesyl transferase inhibitors (FTI); and bisphosphonates.

In another specific embodiment, the methods of the invention encompass administration of an antibody of the invention in combination with the administration of one or more prophylactic/therapeutic agents that are anti-cancer agents such as, but not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha-2a, interferon alpha-2b, interferon alpha-n1, interferon alpha-n3, interferon beta-1a, interferon gamma-1b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogens, antiestrogens, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, hereguline, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A/mycobacterium cell wall skeleton, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors (microalgal), protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer. Preferred additional anti-cancer drugs are 5-fluorouracil and leucovorin.

In more particular embodiments, the present invention also comprises the administration of one or more monoclonal antibodies of the invention in combination with the administration of one or more therapies such as, but not limited to anti-cancer agents such as those disclosed in Table 2.

TABLE 2

| Therapeutic Agent | Administration | Dose | Intervals |
| --- | --- | --- | --- |
| doxorubicin hydrochloride (Adriamycin RDF ® and Adriamycin PFS ®) | Intravenous | 60-75 mg/m$^2$ on Day 1 | 21 day intervals |
| epirubicin hydrochloride (Ellence ™) | Intravenous | 100-120 mg/m$^2$ on Day 1 of each cycle or divided equally and given on Days 1-8 of the cycle | 3-4 week cycles |
| fluorouracil | Intravenous | How supplied: 5 ml and 10 ml vials (containing 250 and 500 mg flourouracil respectively) | |
| docetaxel (Taxotere ®) | Intravenous | 60-100 mg/m$^2$ over 1 hour | Once every 3 weeks |
| paclitaxel | Intravenous | 175 mg/m$^2$ over 3 hours | Every 3 weeks for 4 |

TABLE 2-continued

| Therapeutic Agent | Administration | Dose | Intervals |
| --- | --- | --- | --- |
| (Taxol ®) | | | courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 ml or 20 unit mark) | Once a day |
| flutamide (Eulexin ®) | Oral (capsule) | 250 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/ml | |
| ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 ml of 20 mg/ml solution (100 mg) | |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | Wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: solution of 1 mg/ml in multi-dose vials of 50 mL and 100 mL | |
| mitomycin | Injection | Supplied in 5 mg and 20 mg vials (containing 5 mg and 20 mg mitomycin) | |
| gemcitabine HCl (Gemzar ®) | Intravenous | For NSCLC: 2 schedules have been investigated and the optimum schedule has not been determined. 4 week schedule-administration intravenously at 1000 mg/m$^2$ over 30 minutes; 3 week schedule-Gemzar administered intravenously at 1250 mg/m$^2$ over 30 minutes | 4 week schedule-Days 1, 8 and 15 of each 28-day cycle. Cisplatin intravenously at 100 mg/m$^2$ on day 1 after the infusion of Gemzar. 3 week schedule-Days 1 and 8 of each 21 day cycle. Cisplatin at dosage of 100 mg/m$^2$ administered intravenously after administration of Gemzar on day 1. |
| carboplatin (Paraplatin ®) | Intravenous | Single agent therapy: 360 mg/m$^2$ I.V. on day 1 (infusion lasting 15 minutes or longer) | Every 4 weeks |

TABLE 2-continued

| Therapeutic Agent | Administration | Dose | Intervals |
|---|---|---|---|
| | | Other dosage calculations: Combination therapy with cyclophosphamide, dose adjustment recommendations, formula dosing, etc. | |
| ifosamide (Ifex ®) | Intravenous | 1.2 g/m² daily | 5 consecutive days. Repeat every 3 weeks or after recovery from hematologic toxicity |
| topotecan hydrochloride (Hycamtin ®) | Intravenous | 1.5 mg/m² by intravenous infusion over 30 minutes daily | 5 consecutive days, starting on day 1 of 21 day course |

The invention also encompasses administration of the anti-RYK antibodies of the invention in combination with radiation therapy comprising the use of x-rays, gamma rays and other sources of radiation to destroy the cancer cells. In further embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physicians' Desk Reference* (58$^{th}$ ed., 2004).

The invention also provides a method of inhibiting neurodegeneration and/or promoting functional recovery in a human patient suffering, or at risk of developing, a stroke or other neurological disease/disorder or injury, which comprises administering to said human in need thereof an effective amount of an anti-RYK antibody of the present invention or an antigen-binding fragment thereof.

As used herein, "neurodegeneration" refers to the progressive loss of structure or function of neurons, including death of neurons. As used herein, the term "neurological disease/disorder" or "neurological injury" refers to a disease, disorder or injury to the central or peripheral nervous system.

In addition, the invention provides the use of an anti-RYK antibody of the present invention or an antigen-binding fragment thereof in the preparation of a medicament for inhibiting neurodegeneration and/or promoting functional recovery in a human patient afflicted with, or at risk of developing, a stroke and other neurological disease/disorder or injury.

"Neurological diseases" or "-disorders" as used herein includes, but is not limited to, traumatic brain injury, spinal cord injury, fronto-temporal dementias (tauopathies), peripheral neuropathy, Parkinson's disease, Huntington's disease, Alzheimer's disease, multiple sclerosis or amyotrophic lateral sclerosis (ALS).

In a further aspect there is provided a method of treating stroke (particularly ischemic stroke), brain injury, spinal cord injury, fronto-temporal dementias (tauopathies), peripheral neuropathy, peripheral nerve injury, Parkinson's disease, Huntington's disease, multiple sclerosis and Alzheimer's disease in a human patient which method comprises the administration of a therapeutically effective amount of an anti-RYK antibody of the invention or an antigen-binding fragment thereof.

In a further aspect of the present invention there is provided a method of inhibiting corticospinal tract axon retraction in a human subject which method comprises administering a therapeutically effective amount of an anti-RYK antibody of the present invention or an antigen-binding fragment thereof.

The invention also provides a method of promoting axonal growth and regeneration comprising the step of contacting a human axon with an anti-RYK antibody of the present invention or an antigen-binding fragment thereof. This method may be performed in vitro or in vivo; preferably the method is performed in vivo.

In a further aspect of the invention there is provided a method of inhibiting neurite outgrowth in a human subject which method comprises administering a therapeutically effective amount of an anti-RYK antibody of the present invention or an antigen-binding fragment thereof.

In a further aspect of the present invention there is provided the use of an anti-RYK antibody of the present invention (e.g. an anti-RYK antibody comprising the CDRs set forth herein) or an antigen-binding fragment thereof, in the manufacture of a medicament for the treatment of stroke (particularly ischemic stroke), brain injury, spinal cord injury, fronto-temporal dementias (tauopathies), peripheral neuropathy, peripheral nerve injury, Parkinson's disease, Huntington's disease, Alzheimer's disease, multiple sclerosis or amyotrophic lateral sclerosis (ALS) in a human patient.

In a further aspect of the present invention there is provided the use of an anti-RYK antibody of the present invention (e.g. an anti-RYK antibody comprising the CDRs set forth herein) or an antigen-binding fragment thereof, in the manufacture of a medicament for the inhibition of axon retraction in a subject in need thereof.

In a further aspect of the present invention there is provided the use of an anti-RYK antibody of the present invention (e.g. an anti-RYK antibody comprising the CDRs set forth herein) or an antigen-binding fragment thereof, in the manufacture of a medicament for the promotion of axonal growth and regeneration in a subject in need thereof.

In a further aspect of the present invention there is provided the use of an anti-RYK antibody of the present invention (e.g. an anti-RYK antibody comprising the CDRs set forth herein) or an antigen-binding fragment thereof, in the manufacture of a medicament for the inhibition of neurite outgrowth in a subject in need thereof.

Stem cells and progenitor cells are characterized by their capacity for self-renewal and their ability to differentiate into various functional cell types. Various categories of stem cells include totipotent, pluripotent, multipotent and monopotent stem cells. Totipotency refers to the ability of a stem cell to form all cell types including extraembryonic tissue. Pluripotent stem cells are capable of unlimited self-renewal and can differentiate into any adult cell type (e.g. embryonic stem cells (ESCs) and induced pluripotent cells (iPS) cells). Multipotent stem cells have the ability to differentiate into a limited number of different cell types (e.g. hematopoietic stem cells (HSCs)). Multipotent stem cells can give rise to progenitor cells which can be multipotent (e.g. cardiac progenitor cells can differentiate into endothelial cells, smooth muscle cells or cardiomyocytes) or monopotent, giving rise to only one cell type (e.g. myeloid progenitor cells, endothelial progenitor cells).

Given their role in development, and in maintaining and repairing senescent or diseased adult tissues, stem and progenitor cells represent a means by which aged or diseased tissues may be treated or regenerated. Additionally, the capacity to reprogram fully differentiated adult cells to pluripotency and direct the differentiation of these cells to specific cell types can facilitate disease modeling, drug screening, and patient-specific cell therapy.

Wnt signaling has been reported to play a role in the maintenance of pluripotency in murine and human pluripotent stem cells, in the self-renewal of undifferentiated adult stem cells in multiple tissues as well as the induction of pluripotency in somatic cells. Additionally, recent evidence suggests that manipulation of Wnt signaling can modulate the clonogenic potential, survival and differentiation of human stem cells.

Accordingly, in another aspect, the present invention provides a method of modulating the self-renewal or differentiation of a stem or progenitor cell comprising the step of contacting a stem or progenitor cell with an anti-RYK antibody of the present invention, or an antigen-binding fragment thereof.

Wnt signaling has been implicated in directing the differentiation of cells towards mesodermal and endodermal lineages and blocking differentiation towards the neuroectodermal lineage. In a particular embodiment, the method is directed towards modulating the neuroectodermal potential of a stem or progenitor cell.

In another aspect, the invention provides a method of generating a neural stem cell, neuroepithelial progenitor cell, an astrocyte, oligodendrocyte or neuron comprising the step of contacting a cell with an anti-RYK antibody of the present invention, or an antigen-binding fragment thereof.

As used herein the term "differentiation" and derivatives thereof, refers to the process of the elaboration of particular characteristics, such as marker expression, associated with an end-stage or specialized cell or a cell in the process of becoming a specialized cell. The term is also intended to refer to the process of a specialized or "differentiated" cell of one identity or type transitioning or changing to an alternate identity or type.

In a further aspect of the present invention there is provided a neural stem cell, neuroepithelial progenitor cell, an astrocyte, oligodendrocyte or neuron produced by the method of contacting a cell with an anti-RYK antibody of the present invention, or an antigen-binding fragment thereof.

Antibodies of the invention specifically bind to the WIF domain of human RYK and may inhibit the interaction of Wnt and RYK as well as inhibit downstream Wnt signaling including phosphorylation of Dishevelled protein (Dvl2 and Dvl3). Any method known in the art to assay either the level of binding to the WIF domain of human RYK or phosphorylation of Dishevelled, or downstream activity or gene expression associated with Wnt signaling can be used to assay candidate anti-RYK antibodies to determine their activity.

Thus, based on the knowledge of the antibodies of the present invention, the invention provides methods of assaying and screening for anti-RYK antibodies by incubating antibodies that bind the extracellular domain of human RYK, particularly that specifically bind to the WIF domain of human RYK, with RYK protein or protein constructs or cells that express human RYK. Such methods are set forth in the Examples 1 and 3 below.

Any method known in the art to determine candidate anti-RYK antibody binding/localization on a cell can be used to screen candidate antibodies for desirable binding properties. In one embodiment, flow cytometry is used to determine the binding characteristics of an antibody. In another embodiment, cell-based or immunoassays are used to determine the binding characteristics of an antibody. In this embodiment, antibodies that can compete with a RYK ligand (e.g., Wnt 1, Wnt3a or Wnt5a) for binding to RYK can also be identified. The RYK ligand used in this assay can be soluble protein (e.g., recombinantly expressed) or expressed on a cell so that it is anchored to the cell surface.

In a specific embodiment, the protein construct is fused to the Fc region of human $IgG_1$. In this embodiment, antibodies may be detected using an enzyme immune assay. In another specific embodiment, the antibodies are selected for their ability to compete with ligands (e.g., cell-anchored or purified ligands) that interact with the extracellular domain of human RYK. These antibodies may be screened using routine immunological techniques, including cell-based or ELISA assays.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to normal cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The activity of the therapies used in accordance with the present invention also can be determined by using various experimental animal models for the study of cancer or peripheral nerve injury or spinal cord injury, such as the SCID mouse model or transgenic mice where a murine RYK is replaced with the human RYK, nude mice with human xenografts, or any animal model (including hamsters, rabbits, etc.) known in the art and described in *Relevance of Tumor Models for Anticancer Drug Development* (1999, eds. Fiebig and Burger); *Contributions to Oncology* (1999, Karger); *The Nude Mouse in Oncology Research* (1991, eds. Boven and Winograd); *Anticancer Drug Development Guide* (1997 ed. Teicher) and *Animal Models of Acute Neurological injuries Contemporary Neuroscience* (2008 eds. Chen, Xu, Xu and Zhang), herein incorporated by reference in their entireties.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such a protocol upon the tissue sample is observed, e.g., decreased Wnt signaling or phosphorylation of Dishevelled. A lower level of proliferation or survival of the contacted cells indicates that the therapeutic agent is effective to treat the condition in the patient. Alternatively, decreased Wnt-induced neurite outgrowth in neurons indicates that the therapeutic agent is effective to treat the condition in the patient. Alternatively, instead of culturing cells from a patient, therapeutic agents and methods may be screened using cells of a cell line, including a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of a condition, disease or disorder as discussed herein.

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of one or more anti-RYK antibodies of the invention and a pharmaceutically acceptable carrier. In a further embodiment, the composition of the invention further comprises an additional anti-cancer agent. In a specific embodiment, additional anti-cancer agents include, but are not limited to, chemotherapeutic agents, radiation therapeutic agents, hormonal therapeutic agents, biological therapeutics and immunotherapeutic agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water-free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer a monoclonal antibody of the invention or the combination of a monoclonal antibody of the invention and a prophylactic agent or therapeutic agent useful for preventing or treating cancer, e.g., encapsulation in liposomes, microparticles, microcapsules, recombinant cells capable of expressing the antibody or antibody fragment, receptor-mediated endocytosis (see, e.g., Wu and Wu, 1987, *J. Biol. Chem.* 262:4429-4432), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural, and mucosal (e.g., intranasal, inhaled, and oral routes). In a specific embodiment, prophylactic or therapeutic agents of the invention are administered intramuscularly, intravenously, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In yet another embodiment, the prophylactic or therapeutic agent can be delivered in a controlled release or sustained release system. In one embodiment, a pump may be used to achieve controlled or sustained release (see Langer, supra; Sefton, 1987, *CRC Grit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the antibodies of the invention or fragments thereof (see e.g., Medical Applications of Controlled Release Technology, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; International Publication Nos. WO 99/15154 and WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a further embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in *Medical Applications of Controlled Release Technology*, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Pharm. Sci. Technol* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

Pharmaceutical compositions for use in accordance with the present invention may be formulated in conventional manner using one or more physiologically acceptable carriers or excipients.

Thus, the anti-RYK antibodies of the invention and their physiologically acceptable salts and solvates may be formulated for administration by inhalation or insufflation (either through the mouth or the nose) or oral, parenteral or mucosal (such as buccal, vaginal, rectal, sublingual) administration. In a further embodiment, local or systemic parenteral administration is used.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the prophylactic or therapeutic agents for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The prophylactic or therapeutic agents may also be formulated in rectal compositions such as suppositories or retention enemas, e.g., containing conventional suppository bases such as cocoa butter or other glycerides.

In addition to the formulations described previously, the prophylactic or therapeutic agents may also be formulated as a depot preparation. Such long-acting formulations may be administered by implantation (for example subcutaneously or intramuscularly) or by intramuscular injection. Thus, for example, the prophylactic or therapeutic agents may be formulated with suitable polymeric or hydrophobic materials (for example as an emulsion in an acceptable oil) or ion exchange resins, or as sparingly soluble derivatives, for example, as a sparingly soluble salt.

The invention also provides that a prophylactic or therapeutic agent is packaged in a hermetically sealed container such as an ampoule or sachet indicating the quantity. In one embodiment, the prophylactic or therapeutic agent is supplied as a dry sterilized lyophilized powder or water-free concentrate in a hermetically sealed container and can be reconstituted, e.g., with water or saline to the appropriate concentration for administration to a subject.

In a further embodiment of the invention, the formulation and administration of various chemotherapeutic, biological/immunotherapeutic and hormonal therapeutic agents are known in the art and often described in the *Physicians' Desk Reference*, (58$^{th}$ ed., 2004). The typical doses of various cancer therapeutics known in the art are provided in Table 2.

In other embodiments of the invention, radiation therapy agents such as radioactive isotopes can be given orally as liquids in capsules or as a drink. Radioactive isotopes can also be formulated for intravenous injections. The skilled oncologist can determine the preferred formulation and route of administration.

In certain embodiments the monoclonal antibodies of the invention, are formulated at 1 mg/ml, 5 mg/ml, 10 mg/ml, 25 mg/ml, and 50 mg/ml for intravenous injections and at 5 mg/ml, 10 mg/ml, and 80 mg/ml for repeated subcutaneous administration and intramuscular injection. In other embodiments the monoclonal antibodies of the invention are formulated at between about 0.1 mg/ml and about 1 mg/ml, between about 1 mg/ml and about 5 mg/ml, between about 5 mg/ml and about 10 mg/ml, between about 10 mg/ml and about 25 mg/ml, and between about 25 mg/ml and about 50 mg/ml.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The amount of the composition of the invention which will be effective in the treatment, prevention or management of cancer can be determined by standard research techniques. For example, the dosage of the composition which will be effective in the treatment, prevention or management of cancer can be determined by administering the composition to an animal model such as, e.g., the animal models disclosed herein or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the cancer, and should be decided according to the judgment of the practitioner and each patient's circumstances. Effective doses may be extrapolated from dose-response curves derived from in vitro or animal model test systems. For antibodies, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg, or 0.01 to 0.10 mg/kg of the patient's body weight. Generally, human and humanized antibodies have a longer half-life within the human body than antibodies from other species due to the immune response to the foreign polypeptides. Thus, lower dosages of human antibodies and less frequent administration is often possible. For other cancer therapeutic agents administered to a patient, the typical doses of various cancer therapeutics known in the art are provided in Table 2. Given the invention, certain embodiments will encompass the administration of lower dosages in combination treatment regimens than dosages recommended for the administration of single agents.

The invention provides for any method of administering lower doses of known prophylactic or therapeutic agents than previously thought to be effective for the prevention, treatment, management or amelioration of cancer. In certain embodiments, lower doses of known anti-cancer therapies are administered in combination with lower doses of monoclonal antibodies of the invention.

The invention provides a pharmaceutical pack or kit comprising one or more containers filled with an anti-RYK antibody of the invention. Additionally, one or more other prophylactic or therapeutic agents useful for the treatment of a cancer can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more anti-RYK antibodies of the invention. In another embodiment, a kit further comprises one or more other prophylactic or therapeutic agents useful for the treatment of cancer or for inhibiting neurodegeneration and/or promoting functional recovery in a human patient suffering, or at risk of developing, a stroke or other neurological disease/disorder, in one or more containers. In certain embodiments the anti-RYK antibody of the invention is scFv3, scFvN3, or RWD1. In further embodiments, the other prophylactic or therapeutic agent is a chemotherapeutic. In other embodiments, the prophylactic or therapeutic agent is a biological or hormonal therapeutic.

EXAMPLES

Example 1. Generation of Monoclonal Antibodies to the RYK Extracellular Domain and Epitope Mapping Materials and Methods:
Cell Lines and Drug Treatment HEK293T, CHO-K1, AtT-20/D16v-F2, MCF-7, A431, MDCK, HCT-8, L cells and NIH 3T3 cells were from the American Type Culture Collection. Mouse embryonic fibroblasts (MEFs) were derived from wild-type mouse embryos as described (Wurst W, et al., 1995, Production of targeted embryonic stem cell clones. In: Richwoiod D, Hames B D, editors. *Gene Targeting: A Practical Approach*. Oxford: IRL Press. pp. 33-61). COS-7 cells were from Brian Seed (Harvard University). 293-EBNA cells were from Life Technologies. Cells were maintained in DMEM or RPMI 1640 (Life Technologies) supplemented with 10% heat-inactivated FBS. H-RYK-FLAG/CHO cells were maintained in glutamine-free GMEM (SAFC) supplemented with 10% heat-inactivated and dialyzed FBS, GS supplement (SAFC) and 25 µM methionine sulfoximine (glutamine synthase inhibitor; Sigma-Aldrich). Hybridomas were maintained in Hybridoma-SFM (Life Technologies) with 10% heat-inactivated FBS. SN4741 cells were maintained in DMEM with 10% FBS, 50 U/ml penicillin/streptomycin and 0.6% glucose. All cell lines were incubated at 37° C. in 5% or 10% $CO_2$. Drugs used were: actinonin (Sigma-Aldrich); TAPI-0, -1 and -2 compounds (Peptides International; Louisville, Ky.); SB203580, U0126, GM6001 and its inactive analogue (Calbiochem); phosphoramidon (Roche Diagnostics).

cDNA Constructs

The human RYK extracellular domain constructs pApex-3.hRYK.Fc.FLAG and pApex-3.hRYKWD.Fc.FLAG were described previously (Blakely B D, et al., 2011, *PLoS One* 6: e1837). Human RYK extracellular domain construct H-RYK-FLAG, encoding the human RYK extracellular domain fused to a FLAG epitope tag at the carboxyl terminus, was cloned into the pEE6-CMV vector encoding the glutamine synthase cDNA, thus producing pEE6/H-RYK-FLAG. Full-length human RYK with a 2×Myc epitope tag (pcDNA3.Myc2.hRYK) was described previously (Macheda M L, et al., 2012, *J Biol Chem*). Full-length RYK, with an IL-3 signal peptide at the amino terminus and a FLAG epitope tag inserted near the carboxyl terminus (between residues 598 and 599 of GenBank accession number NP_002949.2), was subcloned into pVITRO3-mcs (InvivoGen) to produce pVITRO3.hRYKFCT.

A double-tagged version of the mouse RYK cDNA was created from pcDNA3.Myc2.RYK (see Halford M M, et al., 2000, *Nat Genet* 25: 414-418), by inserting in-frame a sequence encoding a FLAG epitope tag near the RYK carboxyl terminus between residues 585 and 586 (GenBank accession number NP_038677.3), and was named Myc2.RYK.FLAG.CT (M2RFCT). Mutants of pcDNA3.M2RFCT were produced using the QuikChange Site-Directed Mutagenesis Kit (Stratagene). These substitutions to the RYK proprotein convertase (PC) consensus cleavage sites were: K186Q (monobasic mutant, MB), KK181 to QQ181 (dibasic mutant, DB), KRRK176 to QQQQ176 (tetrabasic mutant, TB) and KRRK176; KK181; K186 to QQQQ176; QQ181; 0186 (compound mutant, CM). Mouse RYK extracellular domain constructs pApex-3.RYKEC.Fc.FLAG, pApex-3.RYKDWD.Fc.FLAG, pApex-3.RYKWD.Fc.FLAG, pApex-3.RYKDN.Fc.FLAG and pApex-3.RYKDC.Fc.FLAG were described previously (Keeble T R, et al., 2006, *J Neurosci* 26: 5840-5848; Macheda M L, et al., 2012, *J Biol Chem*). A glutathione S-transferase (GST) fusion to the intracellular domain of mouse RYK was used for generation of affinity-purified rabbit anti-RYK$^{ICD}$ antibody. *E. coli* BL21-SI (Life Technologies) was transformed with the pET.GEX.CT vector (Sharrocks A D, 1994, *Gene* 138: 105-108), containing the entire mouse RYK intracellular domain (residues 240-594; GST.mRYKICD).

A FLAG-tagged $\alpha_1$-antitrypsin Portland ($\alpha_1$-PDX) cDNA (Jean F, et al., 1998, *Proc Natl Acad Sci USA* 95: 7293-7298) was subcloned into pcDNA3. The mouse c-Met cDNA was amplified by RT-PCR using mouse post-natal day 1 head cDNA template, with a reverse primer that added a carboxyl-terminal FLAG epitope tag, and was cloned into the Hind III and Not I sites of pcDNA3 to produce pcDNA3.c-Met.FLAG. Mouse Wnt constructs pcDNA3.Wnt1.Myc5, pcDNA3.Wnt3a.Myc5 and pcDNA3.Wnt5a.Myc5 were described previously (Macheda M L, et al., 2012, *J Biol Chem*).

Protein Production and Purification

Stable cell lines hRYK.Fc/CHO and hRYKWD.Fc/CHO were generated as described previously (Blakely B D, et al., 2011, *PLoS One* 6: e1837). CHO-K1 cells were transfected with pEE6/H-RYK-FLAG using FuGENE 6 (Roche Diagnostics) and selection was applied after 24 h using medium containing 25 µM methionine sulfoximine. H-RYK-FLAG/CHO, hRYK.Fc/CHO and H-RYK-FLAG/CHO cells were seeded into pleated surface roller bottles (BD Biosciences) and incubated at 37° C. in a normal air atmosphere. Conditioned medium was collected after five days, at which time new medium was added and collected again after a further three days, hRYK.Fc and hRYKWD.Fc proteins were produced as described. To produce RYKEC.Fc.FLAG, RYKD-WD.Fc.FLAG, RYKWD.Fc.FLAG, RYKDN.Fc.FLAG and RYKDC.Fc.FLAG proteins, 293-EBNA cells were transiently transfected with the plasmid and conditioned medium was collected after five days. Conditioned medium was filtered using 0.22 µm filters (Millipore) and secreted protein was purified using anti-FLAG M2 affinity gel (Sigma-Aldrich) as described previously (Stacker S A, et al., 1999, *J Biol Chem* 274: 32127-32136).

RYK Monoclonal Antibody Production and Purification

Two BALB/c mice were injected three times with H-RYK-FLAG protein (WEHI Monoclonal Antibody Facility, Bundoora, Australia). Mouse sera were screened for antibody production by flow cytometry, using HEK293T cells transiently transfected with pcDNA3.Myc2.hRYK by FuGENE 6. Anti-Myc 9E10 antibody (WEHI Monoclonal Antibody Facility) was used as a positive control for cell transfection, while propidium iodide (Sigma-Aldrich) was used to exclude dead cells. Mice shown to have anti-RYK antibodies were boosted once more with H-RYK-FLAG, then four days later the spleens of the mice were isolated and splenocytes were fused to myeloma cells to produce hybridomas (WEHI Monoclonal Antibody Facility). Hybridoma supernatants were screened by flow cytometry as described above.

To produce and purify anti-RYK mouse monoclonal antibodies, the hybridoma clones were seeded into pleated surface roller bottles in Hybridoma-SFM supplemented with 1% heat-inactivated FBS, and were incubated at 37° C. in a normal air atmosphere for nine days. Conditioned medium was filtered through 0.22 µm filters, then antibodies were isolated using Protein A sepharose (Fast Flow 4; GE), followed by IgG elution with 50 mM glycine, pH 3.0, into tubes containing 1:5 volume of 1 M Tris, pH 8.0. Antibody fractions were buffer exchanged with phosphate-buffered saline (PBS) and concentrated using Amicon Ultra centrifuge filters (Millipore).

RYK Polyclonal Antibodies Used for Western Blot Analysis

Two polyclonal antibodies to RYK were generated in rabbits. GST.mRYKICD was used to generate rabbit anti-RYK$^{ICD}$ serum. The whole rabbit serum was heat inactivated, 0.22 µm filtered, depleted of antibodies to GST by incubation with GST-coupled AffiGel 15 matrix (Bio-Rad Laboratories), affinity purified using GST.mRYKICD-coupled AffiGel 15, eluted and buffer exchanged with PBS by ultrafiltration (Amicon Ultra). Purified hRYK.Fc was used to generate rabbit anti-RYK$^{ECD}$ serum. The whole serum was affinity purified using hRYK.Fc as described for anti-RYK$^{ICD}$.

Epitope Mapping of Antibodies by Western Blot Analysis and Peptide Library ELISA To begin epitope mapping of anti-RYK monoclonal antibodies, RYKEC.Fc.FLAG constructs (45 ng) were run on 4-12% NuPAGE Novex Bis-Tris gels (Life Technologies). Western blotting was performed as described previously (Keeble T R, et al., 2006. J Neurosci 26: 5840-5848; Macheda M L, et al., 2012, J Biol Chem), using a 1:20 dilution of hybridoma supernatants containing anti-RYK monoclonal antibody.

To finely map the binding epitope of anti-RYK antibodies, two PepSet peptide libraries of the human RYK extracellular domain were created (Mimotopes, Clayton, Australia). The first PepSet library comprised the entire extracellular domain, consisting of 46 peptides of 16 amino acids with a four amino acid offset. The second PepSet library comprised the region to which anti-RYK monoclonal antibodies bound in the first PepSet library (residues 199-226 of human RYK), consisting of 19 peptides of 10 amino acids with a one amino acid offset. Peptides from both PepSet libraries had an amino-terminal biotin followed by a four amino acid spacer, allowing peptide conjugation to streptavidin-coated 96-well plates (Mimotopes). ELISAs were performed by using purified monoclonal antibodies at 2 µg/ml, or purified scFv proteins at 5 µg/ml. Secondary antibodies were goat anti-mouse IgG-HRP (Bio-Rad Laboratories) and goat anti-human IgG-HRP (Zymed; Life Technologies).

Results:

Fusions of mouse splenocytes with myeloma cells were performed after immunization with different recombinant versions of the human RYK extracellular domain. Mice immunized with H-RYK-FLAG resulted in several monoclonal antibodies of the IgG isotype to RYK, named 1B4, 1G8, 5E3 and 6G1. These antibodies were able to detect RYK by flow cytometry, using cells expressing full-length human RYK (hRYKFCT) (FIG. 1A).

To map the binding site of the anti-RYK monoclonal antibodies, purified mouse RYK extracellular domain constructs (FIG. 1B) were analyzed by Western blotting. All the antibodies recognized wild-type RYK (mRYKEC.Fc) and RYK constructs containing the region at the carboxyl terminus of the extracellular domain, but not a WIF domain-only construct (RYKWD.Fc) or one with deletion of the region carboxyl-terminal to the WIF domain (RYKDC.Fc; FIG. 1C).

A synthetic peptide library comprising the extracellular domain of human RYK was used to further map the epitope (s) recognized by the anti-RYK monoclonal antibodies. A solid phase binding assay showed that the four RYK monoclonal antibodies all detected the same cluster of peptides (40-2), which mapped to the region carboxyl-terminal to the WIF domain (FIG. 1D). A second peptide library allowed mapping of the epitope of all four antibodies to the amino acid sequence RTIYD, which corresponds to residues 212-16 of human RYK. The human RYK WIF domain comprises residues 66-194 (mouse residues 50-178). Therefore, the epitope recognized by the anti-RYK antibodies maps to a region carboxyl-terminal to the WIF domain.

FIG. 1. Generation of Monoclonal Antibodies to the RYK Extracellular Domain and Epitope Mapping.

(A) Flow cytometry using purified anti-RYK mouse monoclonal antibodies 1B4, 1G8, 5E3 and 6G1 on 293-EBNA cells stably expressing pVITRO3-mcs (empty vector control; V) or hRYKFCT (RYK). All antibodies detected RYK in hRYKFCT-transfected but not vector-transfected cells. (B) Schematic of the mouse RYK deletion constructs used in this study. (C) Western blot analysis of purified mouse RYK deletion constructs using anti-RYK monoclonal antibodies 1B4 and 6G1. The pattern of binding was the same for both antibodies. The presence of all the deletion constructs was demonstrated by stripping the membrane and reprobing with anti-RYK$^{ECD}$ polyclonal antibody. Molecular mass standard are shown at left in kDa. IB, immunoblot. (D) ELISA results using anti-RYK monoclonal antibodies 1B4 and 6G1 on an immobilized peptide library of the entire human RYK extracellular domain. Peptides 3 to 37: RYK WIF domain; peptide 47: FLAG epitope (incubated with M2 antibody; positive control); well 48: empty (negative control). The antibodies were used at 2 µg/ml. All antibodies bound to the same epitope, in peptides 40-2. The location of the epitope is shown schematically (bottom). Epitopes for the 1G8 and 5E3 antibodies were identical (data not shown). OD, optical density.

Example 2. Constitutive Proteolytic Processing of the RYK Extracellular Domain

Materials and Methods

Mouse RYK constructs encoding substitutions in the proprotein convertase (PC) consensus sites were transiently transfected into COS-7 cells using FuGENE 6. Medium was changed 24 h later, and cells were treated with the furin inhibitor decanoyl-RVKR-chloromethylketone (Bachem) or an equal volume of DMSO for 12 h before harvesting. Forty-eight hours post-transfection, cells were washed twice with cold PBS before lysis in 1 ml of lysis buffer (50 mM Tris pH 7.5, 150 mM NaCl, 1% Triton X-100) supplemented with 1 mM Na$_3$VO$_4$ and 1× complete protease inhibitor cocktail (Roche Diagnostics), for 30 min. Insoluble material was removed by centrifugation at 16,000 g, 15 min, 4° C. and the supernatant was used for analysis. Protein concentrations were determined using the BCA Protein Assay (Pierce; Thermo Scientific) and immunoprecipitations were performed from equal amounts of lysate protein using anti-FLAG M2 affinity gel. Immunoprecipitates were washed three times with 0.1% Triton X-100/PBS, and bound proteins were eluted in sample buffer. M2-HRP (Sigma-Aldrich) was utilized in Western blotting to detect FLAG-tagged proteins.

For treatments with protease inhibitors, COS-7 cells were transiently transfected with pcDNA3.M2RFCT using FuGENE 6. Cells were treated 36 h post-transfection with inhibitors in fresh medium for 12 h. Conditioned medium was collected and clarified by centrifugation at 10,000 g, adjusted to 0.2% Triton X-100, 0.05% NaN$_3$, 100 mM HEPES pH 7.4, and concentrated 10× by ultrafiltration using Centricon YM-10 filters (Millipore). Concentrated conditioned medium was used for immunoprecipitation experiments with anti-Myc monoclonal antibody 9E10-conjugated sepharose as described above.

Results:

It has previously been shown that mouse RYK is cleaved in a stepwise fashion. The first cleavage step, which liberates a soluble WIF domain-containing extracellular domain (RYK-NTF) and forms a transmembrane carboxyl-terminal fragment (RYK-CTF), must occur before the second cleavage step by γ-secretase can take place, as is observed with other γ-secretase substrates such as amyloid precursor protein and Notch. Transient transfection of a variety of cell lines with full-length mouse RYK showed that although four cell lines were resistant to transfection, the other nine expressed full-length RYK (RYK-FL) and generated a cell-associated ~45 kDa RYK-CTF detectable with the anti-RYK$^{ICD}$ polyclonal antibody (FIG. 2A). Therefore, constitutive proteolytic processing of RYK takes place in many cell lines.

The RYK extracellular domain contains the motif KRRK-MCYKKLEEVK in human, mouse, and rat protein (basic residues bolded), which represents multiple proprotein convertase (PC) consensus cleavage sites (FIG. 2B). Similar basic motifs in secretory proteins are cleaved by PCs during transit through the endoplasmic reticulum and Golgi apparatus.

To determine whether the PC consensus cleavage sites are important for RYK-CTF generation, COS-7 cells were transiently transfected with full-length mouse RYK or derivatives that had basic residues (lysine or arginine) substituted with glutamine. A 55 kDa RYK-CTF was constitutively generated in cells overexpressing wild-type RYK (FIG. 2C, lane 1). RYK-CTF levels were substantially reduced by the tetrabasic mutant substitutions (FIG. 2C, lane 5) and completely abolished by the compound substitutions (FIG. 2C, lane 6). This result suggests that the PC consensus sites, including the KRRK motif, are required for RYK-CTF generation. However, PC-specific inhibition using $\alpha_1$-PDX or a small molecule furin-specific inhibitor, decanoyl-RVKR-chloromethylketone, which were effective in preventing proteolytic processing of c-Met (FIG. 2C, lanes 8, 9, 12 and 13), did not inhibit RYK-CTF generation (FIG. 2C, lanes 7, 10 and 11). It thus remains possible that a PC other than furin, and which is relatively insensitive to inhibition by $\alpha_1$-PDX, is responsible for RYK cleavage.

To define the class of protease responsible for constitutive RYK extracellular domain shedding, M2RFCT-transfected COS-7 cells were treated with a panel of protease inhibitors. The metalloproteinase-specific inhibitors TAPI-0, -1 and -2 and GM6001, but not the inactive analogue GM6001-, reduced the levels of soluble RYK extracellular domain shed into the conditioned medium (FIG. 2D). TAPI-2 reduced shedding of RYK-NTF to a level that was barely detectable (FIG. 2D, lane 6). SB203580 and U0126, specific inhibitors of p38 and MEK mitogen-activated protein kinases that regulate constitutive and growth factor-inducible receptor extracellular domain shedding, respectively, did not affect constitutive shedding of RYK-NTF (FIG. 2D). Therefore, cleavage of the RYK extracellular domain to generate RYK-CTF is likely to be mediated by a matrix metalloproteinase. The CTF remains embedded in the plasma membrane and exposes a short extracellular domain with unknown function. It is likely that RYK-CTF possesses a very immunogenic epitope, as all the anti-RYK mouse monoclonal antibodies generated by the inventors bind to an epitope in the extracellular region of RYK-CTF.

Figure 2:
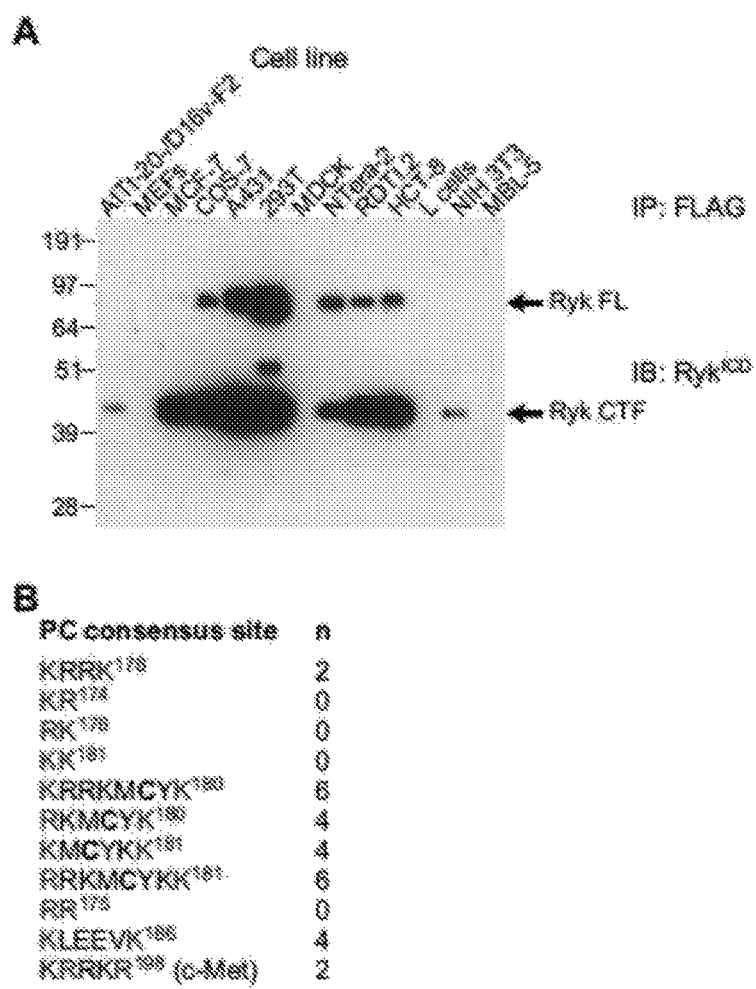
FIG. 2 shows the constitutive proteolytic processing of the RYK extracellular domain. (A) Proteolysis of RYK in mammalian cell lines. (B) Consensus cleavage sites in the mouse RYK extracellular domain (single-letter amino acid code) for proprotein convertases (PCs). (C) The PC consensus sites of RYK are partly required for proteolytic generation of RYK-CTF. (D) Transiently transfected COS-7 cells treated with metalloproteinase inhibitors to inhibit constitutive extracellular domain shedding.
Figure 2:
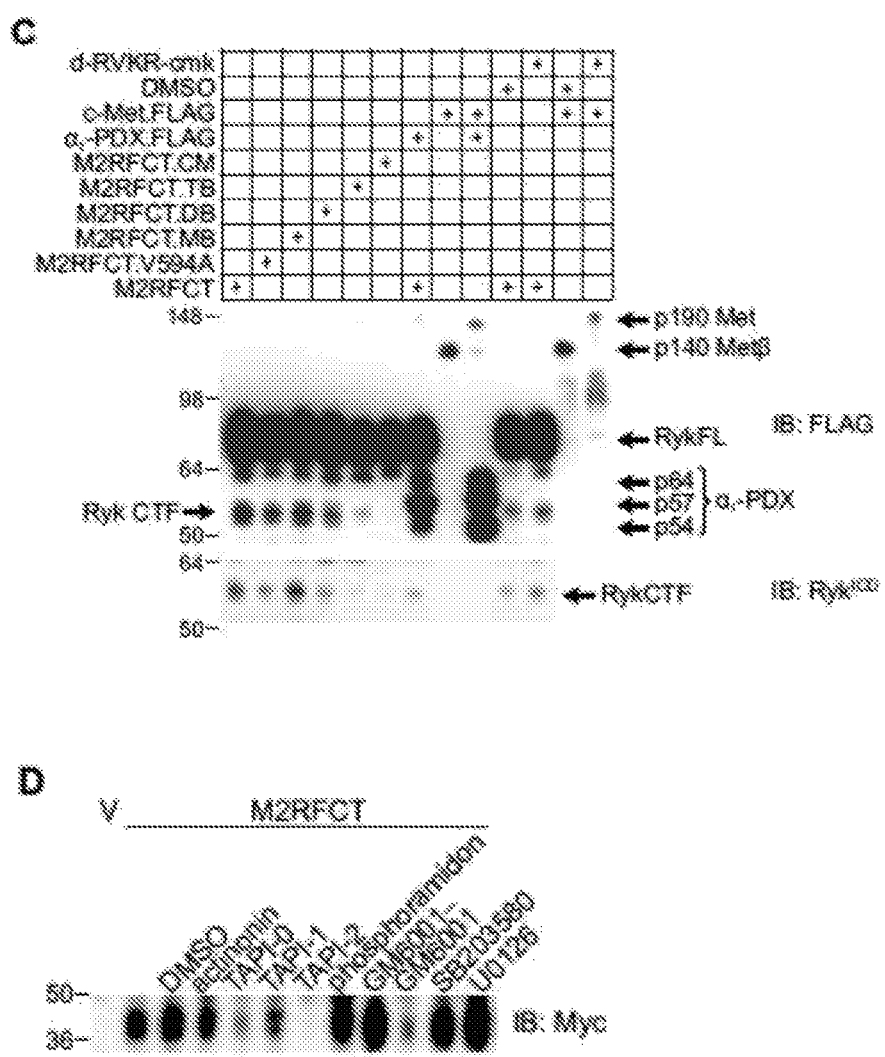

FIG. 2. Constitutive Proteolytic Processing of the RYK Extracellular Domain May Hinder Antibody Generation.

(A) Proteolysis of RYK in mammalian cell lines. Cells were transiently transfected with full-length mouse RYK (pcDNA3.M2RFCT; encoding an amino-terminal 2× Myc epitope tag, and a FLAG epitope tag nine residues from the carboxyl terminus) and lysed 48 h later. Anti-FLAG immunoprecipitates (IP) from 0.8 mg cell lysate were immunoblotted (IB) with anti-RYK$^{ICD}$ polyclonal antibody. Molecular mass standards are shown at left in kDa. RYK-FL, full-length uncleaved RYK; RYK-CTF, RYK carboxyl-terminal fragment; MEFs, mouse embryonic fibroblasts; RDTI.2, RYK-deficient large T antigen-immortalized fibroblasts derived from a RYK$^{-/-}$ embryo. (B) Consensus cleavage sites in the mouse RYK extracellular domain (single-letter amino acid code) for proprotein convertases (PCs). Residues are numbered (in superscript) according to the GenBank sequence NP_038677.3 and cleavage occurs at the carboxyl-terminal side of the consensus sequence. Basic residues at both ends of each consensus site are in blue. The likely furin cleavage site in the mouse c-Met extracellular domain is shown for comparison. The PC consensus cleavage site is $(K/R)X_n(K/R)\downarrow$, where X is any residue except cysteine (rare in this position and therefore shown in bold) or proline, and n=0, 2, 4 or 6. (C) The PC consensus sites of RYK are partly required for proteolytic generation of RYK-CTF. COS-7 cells were transiently transfected with full-length mouse RYK (M2RFCT) or mutant derivatives: V594A; K186Q (MB); KK181→QQ181 (DB); KRRK176→QQQQ176 (TB): and QQQQ176; QQ181; Q186 (CM). The $\alpha_1$-PDX.FLAG protein (p54, p57 and p64 isoforms indicated) was expressed to inhibit endogenous PCs. Mouse c-Met.FLAG was expressed as a positive control for inhibition of furin. The furin inhibitor decanoyl-RVKR-chloromethylketone (d-RVKR-cmk) was used at 50 µM for 12 h. Immunoprecipitates (anti-FLAG) were prepared from 1 mg of lysate protein. The location and identity of RYK-CTF was confirmed using anti-RYK$^{ICD}$ polyclonal antibody (bottom panel). Molecular mass standards are shown at left in kDa. (D) Transiently transfected COS-7 cells were treated with metalloproteinase inhibitors, added 36 h post-transfection in fresh medium for 12 h, to inhibit constitutive extracellular domain shedding. Conditioned medium was concentrated and anti-Myc immunoprecipitates were immunoblotted with anti-Myc to detect shed soluble RYK-NTF. Molecular mass standard are shown at left in kDa. V, empty vector (pcDNA3)-transfected cells.

Example 3. Generation of RYK Inhibitory Antibodies by Screening a Human scFv Phage Display Library Materials and Methods
Generation of a RYK WIF Domain-Specific Chimeric Protein To generate antibodies directed specifically to the RYK WIF domain, we produced a construct that contains the WIF domain of RYK, lacking the carboxyl-terminal cleavage site, fused to the Fc region of human IgG1, termed hRYKWD.Fc. This construct generated a stable 53 kDa protein in CHO-K1 cells. When purified, the fusion protein retained the ability to bind to Wnt proteins, as shown by co-immunoprecipitation (FIG. 3A).

Phage Display Antibody Screening

A phage display antibody library screen was performed using a combination of a direct binding assay to purified hRYKWD.Fc and a competitive ELISA assay (CD BioSciences Inc., NY, USA). The screening protein, purified hRYKWD.Fc, was used on a human scFv naïve phage display library in three rounds of screening. The final (third) round of screening was performed using recombinant mouse Wnt3a protein (R&D Systems) in competitive ELISA. The cDNA of phage clones was sequenced, and the two phage clones able to compete with Wnt3a for binding to hRYK-WD.Fc (scFv3 and scFvN3) were codon optimized to remove stop codons contained in the scFv sequence, thus allowing expression of the scFvs in bacteria (CD BioSciences Inc.). Small-scale purification of both scFv proteins was performed on a nickel sepharose high-performance column via the carboxyl-terminal 6×His epitope the proteins contain, and eluted material resuspended in 50 mM Iris, 50 mM NaCl, 0.1 mM EDTA, 10% glycerol.

Anti-RYK scFv and IgG Antibody Inhibition of RYK Binding to Wnts In Vitro

HEK293T cells were transiently transfected with pcDNA3.Wnt3a.Myc5 or pcDNA3.Wnt5a.Myc5. Cells were lysed 24 h post-transfection as described above. Pre-incubation of 250 ng purified hRYK.Fc with 20 µg scFv or IgG was performed at 4° C. for 1 h, at which time lysate from Wnt3a.Myc5- or Wnt5a.Myc5-transfected cells (10-20 µg) and M2 affinity gel were added, and incubated at 4° C. for 1 h. Immunoprecipitates were washed twice with each of: wash 1, 150 mM NaCl, 50 mM Tris, 0.1% Triton X-100, pH 7.5; wash 2, 500 mM NaCl; and wash 3, 50 mM Tris, pH 7.5. Immunoprecipitated proteins were eluted in sample buffer. Western blotting utilized M2 (Sigma-Aldrich) conjugated to IRDye 800CW (LI-COR Biosciences) to detect FLAG-tagged hRYK.Fc, or anti-Myc tag rabbit polyclonal antibody (Abcam) followed by goat anti-rabbit IgG IRDye 680 (LI-COR Biosciences) secondary antibody to detect Myc-tagged Wnts.

Results:

To avoid issues of poorly immunogenic protein sequences or proteolytic processing that may compromise the integrity or availability of the RYK WIF domain, we screened a human naïve single chain fragment variable (scFv) phage display library to obtain antibodies specific to the RYK WIF domain. The phage display library was screened by an enzyme immunoassay for binding to the purified hRYK-WD.Fc protein (two rounds). A third round of screening was performed for binding to RYK in the presence of recombinant Wnt3a protein, to select clones that can compete with Wnt3a binding to the RYK WIF domain. Of the 98 phage clones screened by competitive ELISA, five clones were identified as being able to compete with Wnt3a for binding to RYK. The phage DNA of these clones was sequenced and found to represent two unique scFv sequences, scFv3 and scFvN3.

To confirm the activity of the scFv proteins and their capacity to compete with the binding of Wnts, we established an assay where the purified scFvs were used to inhibit the binding of Wnts to FLAG-tagged hRYK.Fc, a recombinant fusion protein containing the entire human RYK extracellular domain. ScFv3 inhibited co-immunoprecipitation of Wnt5a but not Wnt3a with hRYK.Fc, while scFvN3 did not alter the amount of either Wnt3a or Wnt5a bound to hRYK.Fc (FIG. 3B). These results suggest that scFv3, but not scFvN3, is able to interfere with RYK binding to Wnts.

Mapping of epitopes recognized by the scFv proteins was performed using the same peptide library utilized to map the epitope recognized by the anti-RYK mouse monoclonal antibodies. Neither of the scFvs bound to consecutive peptides (FIG. 3C), suggesting that the epitope to which each scFv binds is discontinuous and that the scFvs are likely to bind RYK in conformation-dependent manner.

Figure 3:
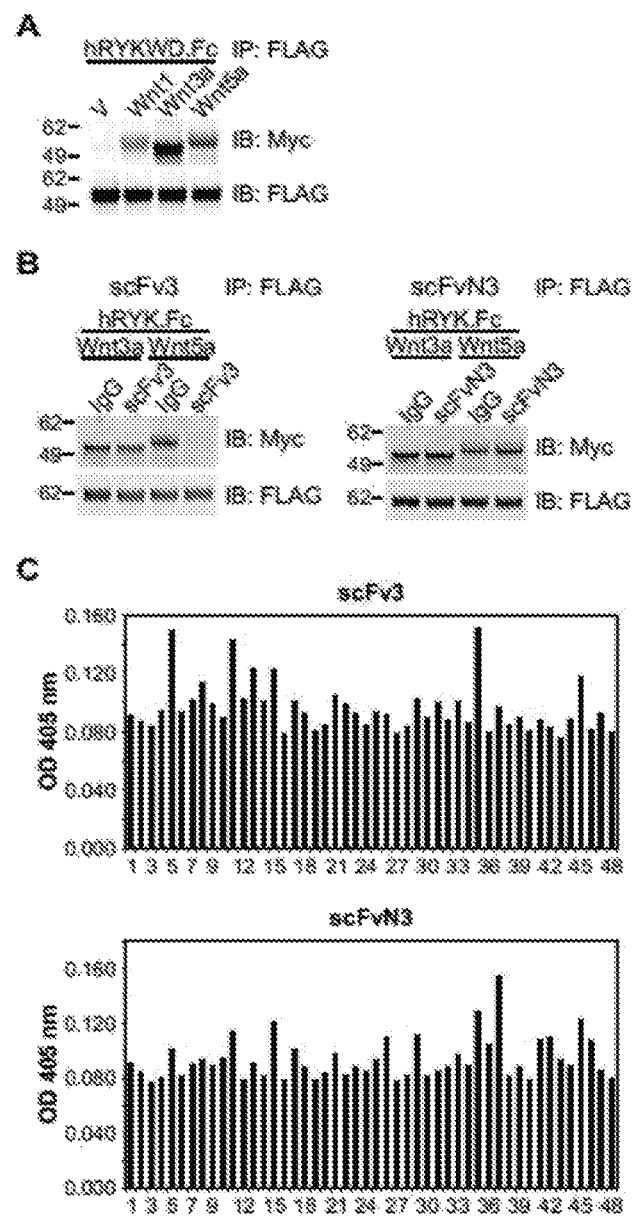
FIG. 3 shows the generation of RYK inhibitory antibodies by screening a human scFv phage display library. (A) Co-immunoprecipitation of Wnt1.Myc5, Wnt3a.Myc5 and Wnt5a.Myc5 with a fusion protein containing the human RYK WIF domain. (B) Co-immunoprecipitation assay with a recombinant fusion protein containing the entire human RYK extracellular domain, Wnt3a or Wnt5a and anti-RYK scFvs. (C) ELISA results using anti-RYK scFvs on an immobilized peptide library of the entire human RYK extracellular domain.

FIG. 3. Generation of RYK Inhibitory Antibodies by Screening a Human scFv Phage Display Library.

(A) Co-immunoprecipitation of Wnt1.Myc5, Wnt3a.Myc5 and Wnt5a.Myc5 from lysate (200 µg) of transfected HEK293T cells with 1 µg purified hRYKWD.Fc protein. Anti-FLAG immunoprecipitations (IP) were performed to pull down hRYKWD.Fc (FLAG-tagged) and these were immunoblotted (IB) with an anti-Myc tag antibody to detect co-precipitated Wnt. Molecular mass standards are shown at the left in kDa. V, empty vector (pcDNA3)-transfected cells. (B) Purified anti-RYK scFv3 and scFvN3 (20 µg) were used in immunoprecipitation experiments to determine whether they could inhibit hRYK.Fc binding to Wnt3a.Myc5 or Wnt5a.Myc5 (10 µg and 20 µg, respectively, of transfected HEK293T cell lysate). Immunoprecipitations (IP) were performed to pull down hRYK.Fc (250 ng), then immunoblotted (IB) as shown. Molecular mass standards are shown at the left in kDa. IgG, normal human IgG (control). (C) ELISA results using anti-RYK scFv proteins (5 µg/ml) on an immobilized peptide library of the entire human RYK extracellular domain (peptides 1 to 46; peptide 47: FLAG epitope; well 48: empty). No epitopes were identified. OD, optical density.

Example 4. Characterization of the Anti-RYK IgG Inhibitory Antibody

Materials and Methods
Production of Full-Length IgG from scFv3

The cDNAs of heavy chain and light chain variable regions from scFv3 were subcloned into two separate vectors, one encoding human IgG κ light chain (pSTDLH3.RYK) and the other human IgG$_1$ γ heavy chain (pSTDHH3.RYK; CD BioSciences Inc.). The vectors encoding heavy and light chains were transiently transfected into FreeStyle 293-F cells using FreeStyle MAX Expression System (Life Technologies). The antibody was purified from conditioned medium six days post-transfection using protein A chromatography (GE) and buffer exchanged with PBS.

Large-scale purification of RWD1 antibody was performed using a stable cell line. CHO-K1 cells were transfected with pSTDHH3.RYK and pSTDLH3.RYK (6:4 ratio) using Lipofectamine 2000 (Life Technologies) and selection was applied after 24 h by adding 300 µg/ml zeocin (Life Technologies) to the medium. Colonies were picked after 7-9 days. The RWD1/CHO stable cell line was seeded into a medium FiberCell cartridge, 20 kDa (FiberCell Systems), using DMEM+10% FBS+200 µg/ml zeocin, and then maintained in DMEM+10% CDM-HD serum replacement (FiberCell Systems)+150 µg/ml zeocin. Extracapillary space medium was collected every 2-3 days. Antibody purification was performed as described above.

Results

To better evaluate the inhibitory effect of anti-RYK scFvs, the blocking antibody scFv3 was grafted onto a human IgG$_1$ backbone to generate a fully human monoclonal antibody called RWD1. Purified RWD1 was tested in vitro by co-immunoprecipitation experiments, which demonstrated that the antibody was able to inhibit hRYK.Fc binding to Wnt5a (FIG. 4A). Epitope mapping of the recombinant IgG antibody using the RYK extracellular domain peptide library confirmed that there was no binding to consecutive peptides (FIG. 4B). Binding of the antibody to RYK was confirmed by ELISA, which showed that there was increased binding of hRYK.Fc ligand to immobilized RWD1 antibody with increasing concentrations of either antibody or ligand (FIG. 4C).

Figure 4:
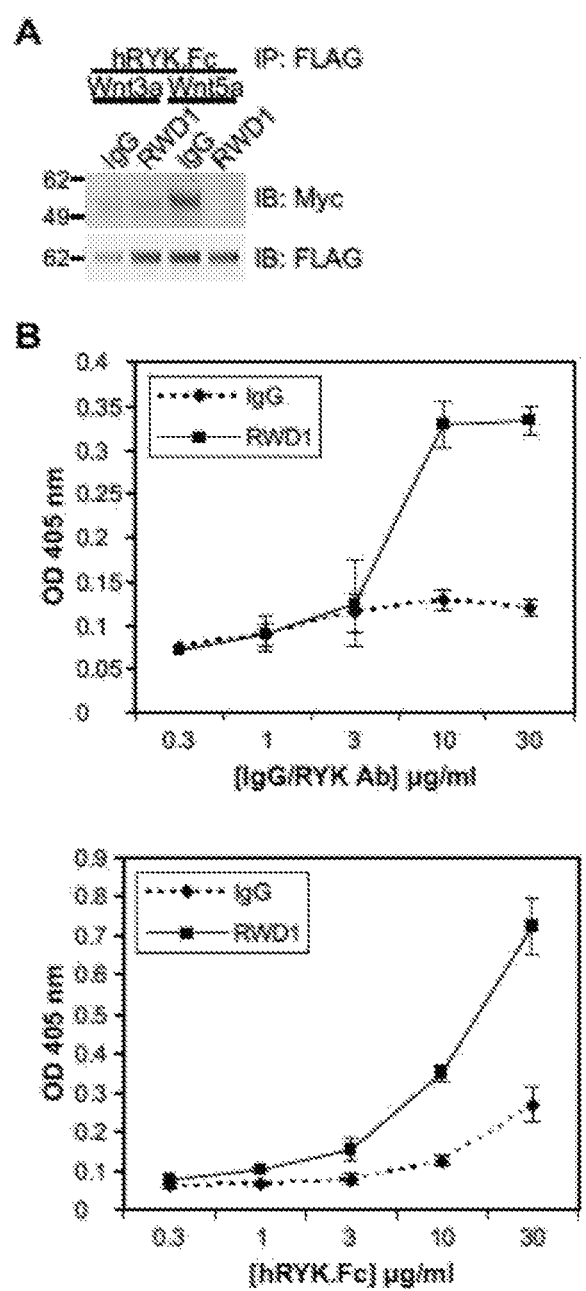
FIG. 4 shows the characterization of the full-length IgG anti-RYK inhibitory antibody RWD1. (A) A co-immunoprecipitation assay with a recombinant fusion protein containing the entire human RYK extracellular domain, purified RWD1 and Wnt3a and Wnt5a. (B) ELISA results of immobilized RWD1 antibody probed with a recombinant fusion protein containing the entire human RYK extracellular domain.

FIG. 4. Characterization of the Full-Length IgG Anti-RYK Inhibitory Antibody RWD1. (A)

Purified RWD1 antibody (20 µg) was used in immunoprecipitation experiments, to determine its ability to inhibit hRYK.Fc binding to Wnt3a.Myc5 or Wnt5a.Myc5 (10 µg and 20 µg, respectively; of transfected HEK293T cell lysate). Immunoprecipitations (IP) were performed to pull down hRYK.Fc (250 ng), then immunoblotted (IB) with an anti-Myc tag antibody to detect Wnt binding. Molecular mass standards are shown at the left in kDa. IgG, normal human IgG. (B) ELISA results of immobilized RWD1 antibody probed with hRYK.Fc protein. Increased hRYK.Fc binding to the antibody was observed with higher concentrations of either immobilized RWD1 or hRYK.Fc protein used for detection. Results represent the mean±standard deviation of two to three independent experiments. IgG, normal human IgG; OD, optical density.

Example 5. RWD1 Antibody Affinity for RYK Using ELISA and Surface Plasmon Resonance Imaging (SPRi) Analysis Materials and Methods
RWD1 Antibody Affinity for RYK Using ELISA and Surface Plasmon Resonance Imaging (SPRi) Analysis RYK binding was determined by ELISA as described previously (Davydova N, et al., 2011, *J Mol Biol* 407: 581-593), using bound RWD1 and probed with purified hRYK.Fc. All SPRi analyses were performed at 25° C. using HBST (10 mM HEPES, pH 7.4, 150 mM NaCl, 0.05% (v/v) Tween-20) as the running buffer. A ProteOn XPR36 SPRi biosensor, GLC sensor chips and coupling reagents (10 mM sodium acetate, pH 4.5; sulfo-N-hydroxysuccinimide (SNHS); 1-ethyl-3-(3-dimethylaminopropyl)-carbodiimide hydrochloride (EDC); and ethanolamine) were purchased from Bio-Rad Laboratories. All antibodies and ligands used for kinetic analysis were buffer exchanged with PBS. Immobilizations were performed at 30 µl/min on the GLC chip. Prior to immobilization, chips were preconditioned with two sequential 10 sec pulses of 50 mM NaOH, 100 mM HCl and 0.5% SDS, followed by equilibration with HBST. For surface activation, 0.4 M EDC and 0.1 M SNHS were each diluted 50-fold in water and mixed together to give a final composition of 8 mM EDC in 2 mM SNHS. Separate vertical channels were activated with 150 µl of the EDC/SNHS mixture. IgGs for immobilization (RWD1 antibody and normal human IgG (R&D Systems; control)) were diluted to 50 µg/ml in 10 mM acetate, pH 4.5, and coupled (3×150 µl) along separate vertical channels followed by an injection of ethanolamine (150 µl) to block the reaction spots. A second pulse of ethanolamine was injected in the horizontal direction. Final immobilization levels were 2046 RU for RWD1 and 1556 RU for normal human IgG.

hRYKWD.Fc (500 nM, 250 nM, 125 nM, 62.5 nM and 31.25 nM) was injected (100 µl at a flow rate of 100 µl/min) in order of increasing concentration along each horizontal channel, allowing a full set of data for kinetic analysis to be obtained. Dissociation was followed for a further 10 min. Following "one-shot kinetic analysis", possible due to the sensor chip configuration of the ProteOn instrument, surfaces were regenerated using 0.85% phosphoric acid (30 µl) at a flow rate of 100 µl/min for repeat analyses.

All binding sensorgrams were collected, processed and analyzed using the integrated ProteOn Manager software (Bio-Rad Laboratories). Following a two-step background subtraction, using an interspot reference followed by the signals generated from the control antibody channel, resulting binding curves were fitted using the Langmuir model describing 1:1 binding stoichiometry or with the Langmuir and mass transfer limitation model. Captured antibody interacting with the five concentrations of antigen was fitted globally to derive the ka, kd and KD.

Figure 5:
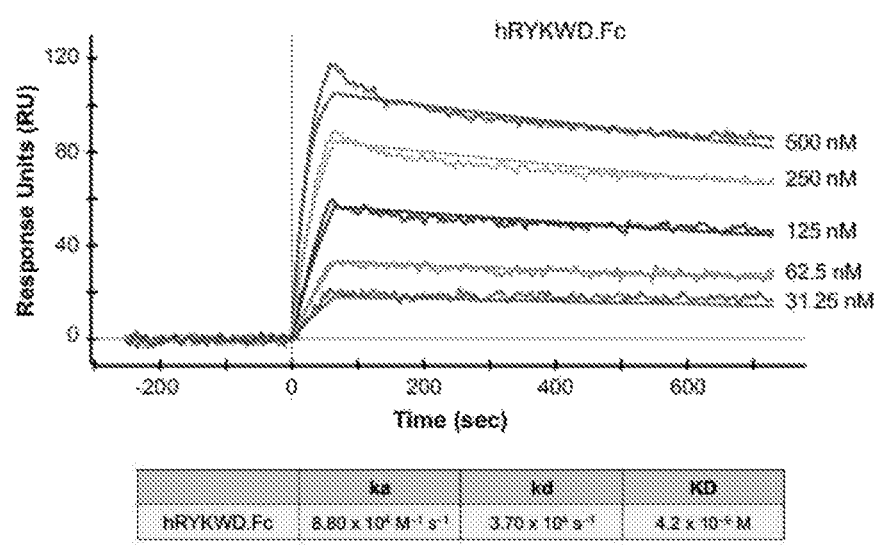
FIG. 5 shows the surface plasmon resonance imaging (SPRi) analysis of the interaction between immobilized RWD1 antibody and purified fusion protein containing the human RYK WIF domain. The kinetic constants derived are shown in the table.

Results:
Surface plasmon resonance imaging was used to determine the affinity of RWD1 antibody for the RYK WIF domain. Purified hRYKWD.Fc was used as the specific binding domain to assess antibody binding. Following a double reference background subtraction protocol, data were fitted globally using a model describing a 1:1 Langmuirian interaction with mass transfer (FIG. 5). These studies revealed an association rate constant (ka) of $8.80 \times 10^4$ M$^{-1}$ sec$^{-1}$ and a dissociation rate constant (kd) of $3.70 \times 10^4$ sec$^{-1}$, giving a calculated dissociation constant (KD) of $4.2 \times 10^{-9}$ M.

FIG. 5. Surface Plasmon Resonance Imaging (SPRi) Analysis of the Interaction Between Immobilized RWD1 Antibody and hRYKWD.Fc.

Experiments were performed using a ProteOn XPR36 SPRi biosensor equipped with a GLC chip as described in Materials and Methods. Using the rotatable sensor chip, live concentrations of ligand (as indicated) and a buffer blank can be analyzed simultaneously, precluding the need for multiple regeneration cycles (one-shot kinetics), Following a two-step background subtraction (an interspot reference and the control antibody channel), resulting binding curves were fitted globally using a model describing a simple 1:1 Langmuirian interaction with mass transfer limitation. The kinetic constants derived are shown in the table.

Example 6. RWD1 Antibody Inhibits Wnt Signaling and RYK Function in Neurons

Materials and Methods:
To assess inhibition of Wnt signaling by RWD1 antibody in SN4741 cells, 100,000 cells per well were seeded into 12-well plates and grown overnight in the absence of serum. Cells were pre-incubated for 45 min in the same medium with normal human IgG (R&D Systems; 50 µg/ml) or RWD1 antibody (50 µg/ml), then stimulated for 2 h with Wnt5a (R&D Systems; 300 ng/ml). Preparation of lysates and immunoblotting were carried out as previously described (Blakely B D, et al., 2011, *PLoS One* 6: e1837).
Neurite Outgrowth Assay Embryos were isolated from Swiss mice time-mated overnight, with visualization of a vaginal plug on the following morning taken as embryonic day (E) 0.5. The cortices of E15.5 mice were microdissected in chilled L15 medium (Life Technologies) and enzymatically dissociated in HBSS containing 0.05% trypsin and 0.1% DNase for 20 min at 37° C. The resultant cell suspension was resuspended in serum-free N2 medium consisting of a 1:1 mixture of F12 and MEM supplemented with 15 mM HEPES buffer, 1 mM glutamine, 6 mg/ml glucose (Sigma-Aldrich), 1.5 mg/ml bovine serum albumin and N2 supplement (all purchased from Life Technologies). Cells were seeded at a density of 35,000 cells per well in a 48-well plate at 37° C., with 5% $CO_2$.

After 72 h in culture, human $IgG_1$ (Ancell Corporation; 50 µg/ml) or RWD1 antibody (50 µg/ml) was added to the cultures, and where appropriate, Wnt5a (R&D Systems; 300 ng/ml) was added 45 min thereafter. The cells remained in culture for a further 72 h before fixing with 4% paraformaldehyde and staining for pill tubulin immunoreactivity (TUJ$^+$). TUJ$^+$ neurons were analyzed from four independent primary cultures. Under all culture conditions, sampling was commenced in the second field of view from the left-hand side of the culture well. The first 30 TUJ$^+$ cells found to be measurable (neurites intact and distinguishable from other stained neurites, i.e. not intertwined with other TUJ$^+$ neurites) were quantified in order to avoid any potential sampling bias. Photomicrographs of each neuron were taken using a 20× objective (Olympus IX71) and measurements of total neurite length obtained using Cell D software (Olympus). Groups were compared using a one-way ANOVA with Tukey's Multiple Comparison post-hoc test.
Results:
The mouse cell line SN4741 was used to confirm that RWD1 can inhibit Wnt-induced signaling. SN4741 cells respond to Wnt5a treatment by phosphorylation of Dishevelled (Dvl) 2 and Dvl3, which are cytoplasmic proteins that transduce both Wnt/β-catenin and β-catenin-independent Wnt signals. Cells treated with Wnt5a showed increased levels of phosphorylated Dvl2, while co-treatment with RWD1 inhibited Wnt5a-mediated Dvl2 phosphorylation (FIG. 6A).

RYK can stimulate axonal growth during embryonic development in rodents. To determine whether RWD1 antibody was able to inhibit RYK function, a neurite outgrowth assay was performed using embryonic day (E) 15.5 mouse cortical neurons. Treatment of neurons with RWD1 alone did not affect neurite outgrowth compared to $IgG_1$ control-treated cells (FIG. 6B). Wnt5a treatment significantly increased total neurite length, while co-treatment with RWD1 significantly inhibited Wnt5a-induced neurite outgrowth (FIG. 6B). These results demonstrate that RWD1 antibody can antagonize Wnt5a-induced signaling, as assessed by inhibition of Dvl2 phosphorylation and of neurite outgrowth.

Figure 6:
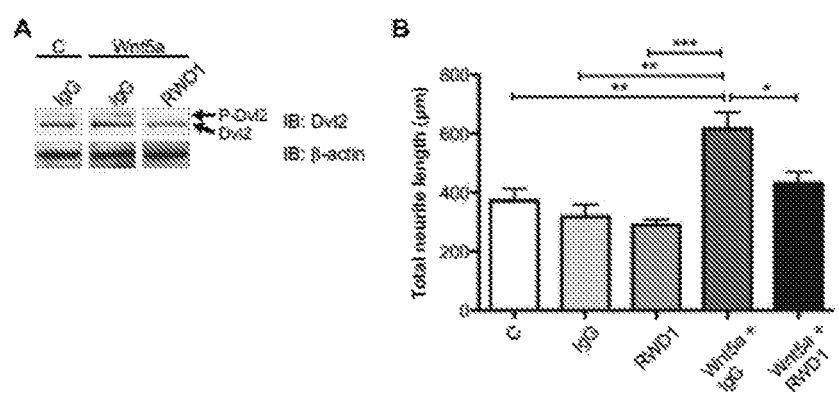
FIG. 6 shows the RWD1 antibody inhibits Wnt signaling and RYK function in neurons. (A) Western blot analysis of lysates from of SN4741 cells treated with Wnt5a and with normal human IgG or RWD1. Lysates were immunoblotted (IB) with anti-Dvl2 and anti-β-actin antibodies. (B) Quantification of neurite growth from E15.5 mouse cortical neurons treated with normal human IgG, RWD1, Wnt5a, or diluent.

FIG. 6. RWD1 Antibody Inhibits Wnt Signaling and RYK Function in Neurons.

(A) Western blot analysis of lysates from SN4741 cells treated with Wnt5a (300 ng/ml) or diluent (PBS; C) and with normal human IgG (50 µg/ml) or RWD1 (50 µg/ml). Lysates were immunoblotted (IB) with anti-Dvl2 and anti-β-actin antibodies. P-Dvl2, phosphorylated Dvl2. Molecular mass standards are shown at the left in kDa. (B) Quantification of neurite growth from E15.5 mouse cortical neurons treated with normal human IgG (50 µg/ml), RWD1 (50 µg/ml), Wnt5a (300 ng/ml), or diluent (PBS; C). Results represent the mean±SEM of four independent experiments. *$P<0.05$; $P<0.01$; *$P<0.001$.

The claims defining the invention are as follows:

1. An antibody produced by the host cell deposited with CellBank Australia having the accession number CBA20130025.

2. A host cell deposited with CellBank Australia having the accession number CBA20130025.

* * * * *

SEQUENCE LISTING

<160> NUMBER OF SEQ ID NOS: 46

<210> SEQ ID NO 1
<211> LENGTH: 240
<212> TYPE: PRT
<213> ORGANISM: Mus musculus

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile His Lys Ala Gly His Thr Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Arg His Phe Asp Tyr Trp Gly Gln Gly Thr Leu Val
            100                 105                 110

Thr Val Ser Ser Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Ala Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Asn Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Val
    210                 215                 220

Gly Ser Pro Arg Thr Phe Gly Gln Gly Thr Lys Val Glu Ile Lys Arg
225                 230                 235                 240

<210> SEQ ID NO 2

```
<211> LENGTH: 116
<212> TYPE: PRT
<213> ORGANISM: Mus musculus

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile His Lys Ala Gly His Thr Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Arg His Phe Asp Tyr Trp Gly Gln Gly Thr Leu Val
            100                 105                 110

Thr Val Ser Ser
        115

<210> SEQ ID NO 3
<211> LENGTH: 108
<212> TYPE: PRT
<213> ORGANISM: Mus musculus

<400> SEQUENCE: 3

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Gly Ser Pro Arg
                85                  90                  95

Thr Phe Gly Gln Gly Thr Lys Val Glu Ile Lys Arg
            100                 105

<210> SEQ ID NO 4
<211> LENGTH: 5
<212> TYPE: PRT
<213> ORGANISM: Mus musculus

<400> SEQUENCE: 4

Ser Tyr Ala Met Ser
1               5

<210> SEQ ID NO 5
<211> LENGTH: 18
<212> TYPE: PRT
<213> ORGANISM: Mus musculus

<400> SEQUENCE: 5

Leu Ile His Lys Ala Gly His Thr Thr Gln Tyr Ala Asp Ser Val Lys
```

```
1               5                   10                  15

Gly Val

<210> SEQ ID NO 6
<211> LENGTH: 6
<212> TYPE: PRT
<213> ORGANISM: Mus musculus

<400> SEQUENCE: 6

Gly Tyr Arg His Phe Asp
1               5

<210> SEQ ID NO 7
<211> LENGTH: 11
<212> TYPE: PRT
<213> ORGANISM: Mus musculus

<400> SEQUENCE: 7

Arg Ala Ser Gln Ser Ile Ser Ser Tyr Leu Asn
1               5                   10

<210> SEQ ID NO 8
<211> LENGTH: 11
<212> TYPE: PRT
<213> ORGANISM: Mus musculus

<400> SEQUENCE: 8

Arg Ala Ser Asn Leu Gln Ser Gly Val Pro Ser
1               5                   10

<210> SEQ ID NO 9
<211> LENGTH: 7
<212> TYPE: PRT
<213> ORGANISM: Mus musculus

<400> SEQUENCE: 9

Ala Val Gly Ser Pro Arg Thr
1               5

<210> SEQ ID NO 10
<211> LENGTH: 240
<212> TYPE: PRT
<213> ORGANISM: Mus musculus

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Thr Ile Ser Arg Val Gly Phe Pro Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly His Pro Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125
```

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gln Ala Ser Val Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Pro Gly
    210                 215                 220

Pro Ala Pro Pro Thr Phe Gly Gln Gly Thr Lys Val Glu Ile Lys Arg
225                 230                 235                 240

<210> SEQ ID NO 11
<211> LENGTH: 134
<212> TYPE: PRT
<213> ORGANISM: Mus musculus

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Arg Val Gly Phe Pro Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly His Pro Phe Asp Tyr Trp Gly Gln Gly Thr Leu Val
            100                 105                 110

Thr Val Ser Ser Pro Gly Pro Ala Pro Pro Thr Phe Gly Gln Gly Thr
        115                 120                 125

Lys Val Glu Ile Lys Arg
    130

<210> SEQ ID NO 12
<211> LENGTH: 108
<212> TYPE: PRT
<213> ORGANISM: Mus musculus

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Gly Pro Ala Pro Pro
                85                  90                  95

Thr Phe Gly Gln Gly Thr Lys Val Glu Ile Lys Arg
            100                 105

<210> SEQ ID NO 13
<211> LENGTH: 5
<212> TYPE: PRT
<213> ORGANISM: Mus musculus

<400> SEQUENCE: 13

Ser Tyr Ala Met Ser
1               5

<210> SEQ ID NO 14
<211> LENGTH: 9
<212> TYPE: PRT
<213> ORGANISM: Mus musculus

<400> SEQUENCE: 14

Thr Ile Ser Arg Val Gly Phe Pro Thr
1               5

<210> SEQ ID NO 15
<211> LENGTH: 6
<212> TYPE: PRT
<213> ORGANISM: Mus musculus

<400> SEQUENCE: 15

Arg Gly His Pro Phe Asp
1               5

<210> SEQ ID NO 16
<211> LENGTH: 11
<212> TYPE: PRT
<213> ORGANISM: Mus musculus

<400> SEQUENCE: 16

Arg Ala Ser Gln Ser Ile Ser Ser Tyr Leu Asn
1               5                   10

<210> SEQ ID NO 17
<211> LENGTH: 14
<212> TYPE: PRT
<213> ORGANISM: Mus musculus

<400> SEQUENCE: 17

Gln Ala Ser Val Leu Gln Ser Gly Val Pro Ser Arg Phe Ser
1               5                   10

<210> SEQ ID NO 18
<211> LENGTH: 7
<212> TYPE: PRT
<213> ORGANISM: Mus musculus

<400> SEQUENCE: 18

Pro Gly Pro Ala Pro Pro Thr
1               5

<210> SEQ ID NO 19
<211> LENGTH: 446
<212> TYPE: PRT
<213> ORGANISM: Mus musculus

<400> SEQUENCE: 19

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Leu Ile His Lys Ala Gly His Thr Thr Gln Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Tyr Arg His Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 20
<211> LENGTH: 213
<212> TYPE: PRT
<213> ORGANISM: Mus musculus

<400> SEQUENCE: 20

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Gly Ser Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu
    210

<210> SEQ ID NO 21
<211> LENGTH: 720
<212> TYPE: DNA
<213> ORGANISM: Mus musculus

<400> SEQUENCE: 21
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcactg attcataagg ctggtcatac tacacagtac     180
gcagactccg tgaagggccg gttcaccatc tccagagaca attccaagaa cacgctgtat     240
ctgcaaatga acagcctgag agccgaggac acggccgtat attactgtgc gaaaggttat     300
cgtcattttg actactgggg ccagggaacc ctggtcaccg tctcgagcgg tggaggcggt     360
tcaggcggag gtggcagcgg cggtggcggg tcgacggaca tccagatgac ccagtctcca     420

```
tcctccctgt ctgcatctgt aggagacaga gtcgccatca cttgccgggc aagtcagagc      480
attagcagct atttaaattg gtatcagcag aaaccaggga aagcccctaa gctcctgatc      540
tatcgggcat ccaatttgca aagtggggtc ccatcaaggt tcagtggcag tggatctggg      600
acagatttca ctctcaccat cagcagtctg caacctgaag attttgcaac ttactactgt      660
caacaggctg ttggttctcc tcgtacgttc ggccaaggga ccaaggtgga aatcaaacgg      720
```

<210> SEQ ID NO 22
<211> LENGTH: 348
<212> TYPE: DNA
<213> ORGANISM: Mus musculus

<400> SEQUENCE: 22

```
gaggtgcagc tgttggagtc tgggggaggc ttggtacagc ctggggggtc cctgagactc       60
tcctgtgcag cctctggatt caccttagc agctatgcca tgagctgggt ccgccaggct      120
ccagggaagg ggctggagtg ggtctcactg attcataagg ctggtcatac tacacagtac      180
gcagactccg tgaagggccg gttcaccatc tccagagaca attccaagaa cacgctgtat      240
ctgcaaatga acagcctgag agccgaggac acggccgtat attactgtgc gaaaggttat      300
cgtcattttg actactgggg ccagggaacc ctggtcaccg tctcgagc                   348
```

<210> SEQ ID NO 23
<211> LENGTH: 324
<212> TYPE: DNA
<213> ORGANISM: Mus musculus

<400> SEQUENCE: 23

```
gacatccaga tgacccagtc tccatcctcc ctgtctgcat ctgtaggaga cagagtcgcc       60
atcacttgcc gggcaagtca gagcattagc agctatttaa attggtatca gcagaaacca      120
gggaaagccc ctaagctcct gatctatcgg gcatccaatt tgcaaagtgg ggtcccatca      180
aggttcagtg gcagtggatc tgggacagat ttcactctca ccatcagcag tctgcaacct      240
gaagattttg caacttacta ctgtcaacag gctgttggtt ctcctcgtac gttcggccaa      300
gggaccaagg tggaaatcaa acgg                                              324
```

<210> SEQ ID NO 24
<211> LENGTH: 15
<212> TYPE: DNA
<213> ORGANISM: Mus musculus

<400> SEQUENCE: 24

```
agctatgcca tgagc                                                         15
```

<210> SEQ ID NO 25
<211> LENGTH: 51
<212> TYPE: DNA
<213> ORGANISM: Mus musculus

<400> SEQUENCE: 25

```
ctgattcata aggctggtca tactacacag tacgcagact ccgtgaaggg c                51
```

<210> SEQ ID NO 26
<211> LENGTH: 18
<212> TYPE: DNA
<213> ORGANISM: Mus musculus

<400> SEQUENCE: 26

```
ggttatcgtc attttgac                                                      18
```

```
<210> SEQ ID NO 27
<211> LENGTH: 33
<212> TYPE: DNA
<213> ORGANISM: Mus musculus

<400> SEQUENCE: 27
cgggcaagtc agagcattag cagctatttta aat                                33

<210> SEQ ID NO 28
<211> LENGTH: 33
<212> TYPE: DNA
<213> ORGANISM: Mus musculus

<400> SEQUENCE: 28
cgggcatcca atttgcaaag tggggtccca tca                                33

<210> SEQ ID NO 29
<211> LENGTH: 21
<212> TYPE: DNA
<213> ORGANISM: Mus musculus

<400> SEQUENCE: 29
gctgttggtt ctcctcgtac g                                             21

<210> SEQ ID NO 30
<211> LENGTH: 720
<212> TYPE: DNA
<213> ORGANISM: Mus musculus

<400> SEQUENCE: 30
gaggtgcagc tgttggagtc tgggggaggc ttggtatagc ctgggggtc cctgagactc    60 tcctgtgcag cctctggatt caccttagc agctatgcca tgagctgggt ccgccaggct   120
ccagggaagg ggctggagtg gtctcaacg atttcgcggg ttggttttcc gacagtttac   180
gcagactccg tgaagggccg gttcaccatc tccagagaca attccaagaa cacgctgtat   240
ctgcaaatga acagcctgag agccgaggac acggccgtat attactgtgc gaaacgtggt   300
catccgtttg actactgggg ccagggaacc ctggtcaccg tctcgagcgg tggaggcggt   360
tcaggcggag gtggcagcgg cggtggcggg tcgacggaca tccagatgac ccagtctcca   420
tcctccctgt ctgcatctgt aggagacaga gtcaccatca cttgccgggc aagtcagagc   480
attagcagct atttaaattg gtatcagcag aaaccaggga agcccctaa gctcctgatc   540 tatcaggcat ccgttttgca aagtgggtc ccatcaaggt tcagtggcag tggatctggg   600
acagatttca ctctcaccat cagcagtctg caacctgaag attttgcaac ttactactgt   660
caacagccgg gtcctgctcc tccgacgttc ggccaaggga ccaaggtgga atcaaacgg   720

<210> SEQ ID NO 31
<211> LENGTH: 348
<212> TYPE: DNA
<213> ORGANISM: Mus musculus

<400> SEQUENCE: 31
gaggtgcagc tgttggagtc tgggggaggc ttggtatagc ctgggggtc cctgagactc    60 tcctgtgcag cctctggatt caccttagc agctatgcca tgagctgggt ccgccaggct   120
ccagggaagg ggctggagtg gtctcaacg atttcgcggg ttggttttcc gacagtttac   180
gcagactccg tgaagggccg gttcaccatc tccagagaca attccaagaa cacgctgtat   240
```

```
ctgcaaatga acagcctgag agccgaggac acggccgtat attactgtgc gaaacgtggt    300
catccgtttg actactgggg ccagggaacc ctggtcaccg tctcgagc                 348
```

<210> SEQ ID NO 32
<211> LENGTH: 324
<212> TYPE: DNA
<213> ORGANISM: Mus musculus

<400> SEQUENCE: 32

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatcag gcatccgttt tgcaaagtgg ggtcccatca    180
aggttcagtg gcagtggatc tgggacagat ttcactctca ccatcagcag tctgcaacct    240
gaagattttg caacttacta ctgtcaacag ccgggtcctg ctcctccgac gttcggccaa    300
gggaccaagg tggaaatcaa acgg                                           324
```

<210> SEQ ID NO 33
<211> LENGTH: 15
<212> TYPE: DNA
<213> ORGANISM: Mus musculus

<400> SEQUENCE: 33

```
agctatgcca tgagc                                                      15
```

<210> SEQ ID NO 34
<211> LENGTH: 60
<212> TYPE: DNA
<213> ORGANISM: Mus musculus

<400> SEQUENCE: 34

```
acgatttcgc gggttggttt tccgacagtt tacgcagact ccgtgaaggg ccggttcacc     60
```

<210> SEQ ID NO 35
<211> LENGTH: 18
<212> TYPE: DNA
<213> ORGANISM: Mus musculus

<400> SEQUENCE: 35

```
cgtggtcatc cgtttgac                                                   18
```

<210> SEQ ID NO 36
<211> LENGTH: 33
<212> TYPE: DNA
<213> ORGANISM: Mus musculus

<400> SEQUENCE: 36

```
cgggcaagtc agagcattag cagctattta aat                                  33
```

<210> SEQ ID NO 37
<211> LENGTH: 42
<212> TYPE: DNA
<213> ORGANISM: Mus musculus

<400> SEQUENCE: 37

```
caggcatccg tttttgcaaag tggggtccca tcaaggttca gt                       42
```

<210> SEQ ID NO 38
<211> LENGTH: 30
<212> TYPE: DNA
<213> ORGANISM: Mus musculus

<400> SEQUENCE: 38
ccgggtcctg ctcctccgac gttcggccaa                                30

<210> SEQ ID NO 39
<211> LENGTH: 1395
<212> TYPE: DNA
<213> ORGANISM: Mus musculus

<400> SEQUENCE: 39
atggaactgg gcctgagctg gatcttcctg ctggccatcc tgaagggcgt gcagtgcgag    60
gtgcagctgt tggagtctgg gggaggcttg gtacagcctg gggggtccct gagactctcc   120
tgtgcagcct ctggattcac ctttagcagc tatgccatga gctgggtccg ccaggctcca   180
gggaaggggc tggagtgggt ctcactgatt cataaggctg gtcatactac acagtacgca   240
gactccgtga agggccggtt caccatctcc agagacaatt ccaagaacac gctgtatctg   300
caaatgaaca gcctgagagc cgaggacacg gccgtatatt actgtgcgaa aggttatcgt   360
cattttgact actggggcca gggaaccctg gtcaccgtct ccagcgctag caccaagggc   420
ccatcggtct tccccctggc accctcctcc aagagcacct ctgggggcac agcggccctg   480
ggctgcctgg tcaaggacta cttccccgaa ccggtgacgg tgtcgtggaa ctcaggcgcc   540
ctgaccagcg gcgtgcacac cttcccggct gtcctacagt cctcaggact ctactccctc   600
agcagcgtgg tgaccgtgcc ctccagcagc ttgggcaccc agacctacat ctgcaacgtg   660
aatcacaagc ccagcaacac caaggtggac aagaaagttg agcccaaatc ttgtgacaaa   720
actcacacat gcccaccgtg cccagcacct gaactcctgg ggggaccgtc agtcttcctc   780
ttccccccaa acccaaggac acccctcatg atctcccgga cccctgaggt cacatgcgtg   840
gtggtggacg tgagccacga agaccctgag gtcaagttca actggtacgt ggacggcgtg   900
gaggtgcata atgccaagac aaagccgcgg gaggagcagt acaacagcac gtaccgtgtg   960
gtcagcgtcc tcaccgtcct gcaccaggac tggctgaatg gcaaggagta caagtgcaag  1020
gtctccaaca aagccctccc agcccccatc gagaaaacca tctccaaagc caaagggcag  1080
ccccgagaac cacaggtgta caccctgccc ccatcccggg aggagatgac caagaaccag  1140
gtcagcctga cctgcctggt caaaggcttc tatcccagcg acatcgccgt ggagtgggag  1200
agcaatgggc agccggagaa caactacaag accacgcctc ccgtgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                  1395

<210> SEQ ID NO 40
<211> LENGTH: 699
<212> TYPE: DNA
<213> ORGANISM: Mus musculus

<400> SEQUENCE: 40
atgcgcgtgc tgcccagct gctgggcctg ctcctgctgt ggctgcccgg caccccggtgc   60 gacatccaga tgacccagtc tccatcctcc ctgtctgcat ctgtaggaga cagagtcgcc  120
atcacttgcc gggcaagtca gagcattagc agctatttaa attggtatca gcagaaacca  180
gggaaagccc ctaagctcct gatctatcgg catccaattt gcaaagtgg ggtcccatca   240 aggttcagtg gcagtggatc tgggacagat ttcactctca ccatcagcag tctgcaacct  300

```
gaagattttg caacttacta ctgtcaacag gctgttggtt ctcctcgtac cttcggccaa    360
gggaccaagg tggaaatcaa acgaactgtg gctgcaccat ctgtcttcat cttcccgcca    420
tctgatgagc agttgaaatc tggaactgcc tctgttgtgt gcctgcttaa taacttctat    480
cccagggagg ccaaagtaca gtggaaggtg ataacgccc tccaatcggg taactcccag     540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagcttgc ccgtcacaaa gagcttcaac aggggagag                           699
```

<210> SEQ ID NO 41
<211> LENGTH: 2942
<212> TYPE: DNA
<213> ORGANISM: Homo sapiens

<400> SEQUENCE: 41

```
cggctcgggg ctgtgagcgg ctcggggccg ggggtgggcg gcggtgcggc gggcggccga     60
cgctcctctt cggcggcggc ggcggcggcc atgcgtgggg cggcgcggct ggggcggccg    120
ggccggagtt gcctcccggg ggcccgcggc ctgagggccc cgccgccgcc gccgctgctg    180
cttctgcttg cgctgttgcc gctgctgccc gcgcctggcg ctgccgccgc ccccgccccg    240
cggcccccgg agctgcagtc ggcttccgcg gggcccagcg tgagtctcta cctgagcgag    300
gacgaggtgc gccggctgat cggtcttgat gcagaacttt attatgtgag aaatgacctt    360
attagtcact acgctctatc ctttagtctg ttagtaccca gtgagacaaa tttcctgcac    420
ttcacctggc atgcgaagtc caaggttgaa tataagctgg gattccaagt ggacaatgtt    480
ttggcaatgg atatgcccca ggtcaacatt tctgttcagg gggaagttcc acgcacttta    540
tcagtgtttc gggtagagct ttcctgtact ggcaaagtag attctgaagt tatgatacta    600
atgcagctca acttgacagt aaattcttca aaaaatttta ccgtcttaaa ttttaaacga    660
aggaaaatgt gctacaaaaa acttgaagaa gtaaaaactt cagccttgga caaaaacact    720
agcagaacta tttatgatcc tgtacatgca gctccaacca cttctacgcg tgtgttttat    780
attagtgtag ggtttgttg tgcagtaata tttctcgtag caataatatt agctgttttg     840
caccttcata gtatgaaaag gattgaactg gatgacagca ttagtgccag cagtagttcc    900
caagggctgt ctcagccatc cacccagacg actcagtatc tgagagcaga cacgcccaac    960
aatgcaactc ctatcaccag ctccttaggt tatcctacct tgcggataga aagaacgac    1020 ttgagaagtg tcactctttt ggaggccaaa ggcaaggtga aggatatagc aatatccaga   1080
gagaggataa ctctaaaaga tgtactccaa gaaggtactt ttgggcgtat tttccatggg   1140 atttaatag atgaaaaaga tccaaataaa gaaaaacaag catttgtcaa aacagttaaa   1200
gatcaagctt ctgaaattca ggtgacaatg atgctcactg aaagttgtaa gctgcgaggt   1260
cttcatcaca gaaatcttct tcctattact catgtgtgta tagaagaagg agaaaagccc   1320
atggtgatat tgccttacat gaattggggg aatcttaaat tgttttacg acagtgcaag    1380 ttagtagagg ccaataatcc acaggcaatt tctcagcaag acctggtaca catggctatt   1440
cagattgcct gtggaatgag ctacctggcc agaaggaag tcatccacaa agacctggct    1500
gccaggaact gtgtcattga tgacacactt caagttaaga tcacagacaa tgccctctcc   1560
agagacttgt tccccatgga ctatcactgt ctgggggaca tgaaaacag gccagttcgt    1620 tggatggctc ttgaaagtct ggttaataac gagttctcta cgctagtga tgtgtgggcc    1680 tttggagtga cgctgtggga actcatgact ctgggccaga ctccctacgt ggacattgac   1740
```

```
cccttcgaga tggccgcata cctgaaagat ggttaccgaa tagcccagcc aatcaactgt   1800
cctgatgaat tatttgctgt gatggcctgt tgctgggcct tagatccaga ggagaggccc   1860
aagtttcagc agctggtaca gtgcctaaca gagtttcatg cagccctggg ggcctacgtc   1920
tgactcctct ccaatcccac accatcagga agaaggtgcc tgtcggggct cacttgaagc   1980
ctgtcaggga tgctttgtat ctaacacaac gccaacagaa gcacatttgt cttccagaac   2040
accgtgcctt agaaatgctt tagaatctga acttttaaag acagacttaa taatgtggca   2100
tattttctag atatcacttt tattaggttg aactgaaagg ttttgtaa atttttggc      2160 caaaattttt taaaacatac ttactttgga ctaggggtac attcttacaa aataaataaa   2220 cagttttaa aattgtttag acacagatat ttggaattag ctatcttagt gccaactgct    2280 tttatttt ttacttcatc aaggtgatgt aagtgactca cctttaaagt ttttttagtg     2340 ttattttta tcactactct gggaaatggt ttgtcttcaa gatgcaatac ttttcttagt    2400
aaaggaaaaa cagcataaaa agatacctgg tctgccttgt acaagaaaag gcaatattag   2460
aggaagaaaa tttaaagaaa agctagagga aaaaaaatt ttttaaaaa tacttattag     2520 aagcaaactg cccttgcatg gaaaactgtt tattttttc agtgaaaagg aattctgctt    2580
tcgtgttttt gggaaagcag gaactgagtt cattacatct ttaatttggc agaaattagc   2640
ctttctgtga accagatgtg gtttggggca gatctgtagt aaacaatggt gattttattt   2700
atttttactc tctggaaaag gagataatac aattccagaa agtgaactca tatttctaag   2760
gttaagattc cctttattg cacctagaat agtgctatgc acagagcggg tgcttgagtt    2820
gttgtcgttt tttgtttgtt ttaaatgt aaactggtaa attttgtgct tatcttcaag     2880
gctggcttaa gtataaaatt gttttttaaa cacttgaaaa attaaaggat ttgttttata   2940
tt                                                                   2942
```

<210> SEQ ID NO 42
<211> LENGTH: 610
<212> TYPE: PRT
<213> ORGANISM: Homo sapiens

<400> SEQUENCE: 42

```
Met Arg Gly Ala Ala Arg Leu Gly Arg Pro Gly Arg Ser Cys Leu Pro
1               5                   10                  15

Gly Ala Arg Gly Leu Arg Ala Pro Pro Pro Leu Leu Leu Leu
            20                  25                  30

Leu Ala Leu Leu Pro Leu Leu Pro Ala Pro Gly Ala Ala Ala Pro
        35                  40                  45

Ala Pro Arg Pro Pro Glu Leu Gln Ser Ala Ser Ala Gly Pro Ser Val
    50                  55                  60

Ser Leu Tyr Leu Ser Glu Asp Glu Val Arg Arg Leu Ile Gly Leu Asp
65                  70                  75                  80

Ala Glu Leu Tyr Tyr Val Arg Asn Asp Leu Ile Ser His Tyr Ala Leu
                85                  90                  95

Ser Phe Ser Leu Leu Val Pro Ser Glu Thr Asn Phe Leu His Phe Thr
            100                 105                 110

Trp His Ala Lys Ser Lys Val Glu Tyr Lys Leu Gly Phe Gln Val Asp
        115                 120                 125

Asn Val Leu Ala Met Asp Met Pro Gln Val Asn Ile Ser Val Gln Gly
    130                 135                 140

Glu Val Pro Arg Thr Leu Ser Val Phe Arg Val Glu Leu Ser Cys Thr
```

```
            145                 150                 155                 160
Gly Lys Val Asp Ser Glu Val Met Ile Leu Met Gln Leu Asn Leu Thr
                165                 170                 175
Val Asn Ser Ser Lys Asn Phe Thr Val Leu Asn Phe Lys Arg Arg Lys
                180                 185                 190
Met Cys Tyr Lys Lys Leu Glu Glu Val Lys Thr Ser Ala Leu Asp Lys
                195                 200                 205
Asn Thr Ser Arg Thr Ile Tyr Asp Pro Val His Ala Ala Pro Thr Thr
                210                 215                 220
Ser Thr Arg Val Phe Tyr Ile Ser Val Gly Val Cys Cys Ala Val Ile
225                 230                 235                 240
Phe Leu Val Ala Ile Ile Leu Ala Val Leu His Leu His Ser Met Lys
                245                 250                 255
Arg Ile Glu Leu Asp Asp Ser Ile Ser Ala Ser Ser Ser Gln Gly
                260                 265                 270
Leu Ser Gln Pro Ser Thr Gln Thr Thr Gln Tyr Leu Arg Ala Asp Thr
                275                 280                 285
Pro Asn Asn Ala Thr Pro Ile Thr Ser Ser Leu Gly Tyr Pro Thr Leu
                290                 295                 300
Arg Ile Glu Lys Asn Asp Leu Arg Ser Val Thr Leu Leu Glu Ala Lys
305                 310                 315                 320
Gly Lys Val Lys Asp Ile Ala Ile Ser Arg Glu Arg Ile Thr Leu Lys
                325                 330                 335
Asp Val Leu Gln Glu Gly Thr Phe Gly Arg Ile Phe His Gly Ile Leu
                340                 345                 350
Ile Asp Glu Lys Asp Pro Asn Lys Glu Lys Gln Ala Phe Val Lys Thr
                355                 360                 365
Val Lys Asp Gln Ala Ser Glu Ile Gln Val Thr Met Met Leu Thr Glu
                370                 375                 380
Ser Cys Lys Leu Arg Gly Leu His His Arg Asn Leu Leu Pro Ile Thr
385                 390                 395                 400
His Val Cys Ile Glu Glu Gly Glu Lys Pro Met Val Ile Leu Pro Tyr
                405                 410                 415
Met Asn Trp Gly Asn Leu Lys Leu Phe Leu Arg Gln Cys Lys Leu Val
                420                 425                 430
Glu Ala Asn Asn Pro Gln Ala Ile Ser Gln Gln Asp Leu Val His Met
                435                 440                 445
Ala Ile Gln Ile Ala Cys Gly Met Ser Tyr Leu Ala Arg Arg Glu Val
                450                 455                 460
Ile His Lys Asp Leu Ala Ala Arg Asn Cys Val Ile Asp Asp Thr Leu
465                 470                 475                 480
Gln Val Lys Ile Thr Asp Asn Ala Leu Ser Arg Asp Leu Phe Pro Met
                485                 490                 495
Asp Tyr His Cys Leu Gly Asp Asn Glu Asn Arg Pro Val Arg Trp Met
                500                 505                 510
Ala Leu Glu Ser Leu Val Asn Asn Glu Phe Ser Ser Ala Ser Asp Val
                515                 520                 525
Trp Ala Phe Gly Val Thr Leu Trp Glu Leu Met Thr Leu Gly Gln Thr
                530                 535                 540
Pro Tyr Val Asp Ile Asp Pro Phe Glu Met Ala Ala Tyr Leu Lys Asp
545                 550                 555                 560
Gly Tyr Arg Ile Ala Gln Pro Ile Asn Cys Pro Asp Glu Leu Phe Ala
                565                 570                 575
```

Val Met Ala Cys Cys Trp Ala Leu Asp Pro Glu Glu Arg Pro Lys Phe
            580                 585                 590

Gln Gln Leu Val Gln Cys Leu Thr Glu Phe His Ala Ala Leu Gly Ala
        595                 600                 605

Tyr Val
    610

<210> SEQ ID NO 43
<211> LENGTH: 2936
<212> TYPE: DNA
<213> ORGANISM: Homo sapiens

<400> SEQUENCE: 43

| | | | | | |
|---|---|---|---|---|---|
| cggctcgggg | ctgtgagcgg | ctcggggccg | ggggtgggcg | gcggtgcggc | gggcggccga | 60 |
| cgctcctctt | cggcggcggc | ggcggcggcc | atgcgtgggg | cggcgcggct | ggggcggccg | 120 |
| ggccggagtt | gcctcccggg | ggcccgcggc | ctgagggccc | cgccgccgcc | gccgctgctg | 180 |
| cttctgcttg | cgctgttgcc | gctgctgccc | gcgcctggcg | ctgccgccgc | ccccgccccg | 240 |
| cggccccccgg | agctgcagtc | ggcttccgcg | gggcccagcg | tgagtctcta | cctgagcgag | 300 |
| gacgaggtgc | gccggctgat | cggtcttgat | gcagaacttt | attatgtgag | aaatgacctt | 360 |
| attagtcact | acgctctatc | ctttagtctg | ttagtaccca | gtgagacaaa | tttcctgcac | 420 |
| ttcacctggc | atgcgaagtc | caaggttgaa | tataagctgg | gattccaagt | ggacaatgtt | 480 |
| ttggcaatgg | atatgcccca | ggtcaacatt | tctgttcagg | gggaagttcc | acgcacttta | 540 |
| tcagtgtttc | gggtagagct | ttcctgtact | ggcaaagtag | attctgaagt | tatgatacta | 600 |
| atgcagctca | acttgacagt | aaattcttca | aaaaatttta | ccgtcttaaa | ttttaaacga | 660 |
| aggaaaatgt | gctacaaaaa | acttgaagaa | gtaaaaactt | cagccttgga | caaaaacact | 720 |
| agcagaacta | tttatgatcc | tgtacatgca | gctccaacca | cttctacgcg | tgtgttttat | 780 |
| attagtgtag | ggtttgttg | tgcagtaata | tttctcgtag | caataatatt | agctgttttg | 840 |
| caccttcata | gtatgaaaag | gattgaactg | gatgacagca | ttagtgccag | cagtagttcc | 900 |
| caagggctgt | ctcagccatc | cacccagacg | actcagtatc | tgagagcaga | cacgcccaac | 960 |
| aatgcaactc | ctatcaccag | ttatcctacc | ttgcggatag | agaagaacga | cttgagaagt | 1020 |
| gtcactcttt | tggaggccaa | aggcaaggtg | aaggatatag | caatatccag | agagaggata | 1080 |
| actctaaaag | atgtactcca | agaaggtact | tttgggcgta | ttttccatgg | gattttaata | 1140 |
| gatgaaaaag | atccaaataa | agaaaaacaa | gcatttgtca | aaacagttaa | agatcaagct | 1200 |
| tctgaaattc | aggtgacaat | gatgctcact | gaaagttgta | agctgcgagg | tcttcatcac | 1260 |
| agaaatcttc | ttcctattac | tcatgtgtgt | atagaagaag | gagaaaagcc | catggtgata | 1320 |
| ttgccttaca | tgaattgggg | gaatcttaaa | ttgttttac | gacagtgcaa | gttagtagag | 1380 |
| gccaataatc | cacaggcaat | ttctcagcaa | gacctggtac | acatggctat | tcagattgcc | 1440 |
| tgtggaatga | gctacctggc | cagaagggaa | gtcatccaca | aagacctggc | tgccaggaac | 1500 |
| tgtgtcattg | atgacacact | tcaagttaag | atcacagaca | atgccctctc | cagagacttg | 1560 |
| ttccccatgg | actatcactg | tctgggggac | aatgaaaaca | ggccagttcg | ttggatggct | 1620 |
| cttgaaagtc | tggttaataa | cgagttctct | agcgctagtg | atgtgtgggc | ctttggagtg | 1680 |
| acgctgtggg | aactcatgac | tctgggccag | actccctacg | tggacattga | ccccttcgag | 1740 |
| atggccgcat | acctgaaaga | tggttaccga | atagcccagc | caatcaactg | tcctgatgaa | 1800 |
| gctttatttg | ctgtgatggc | ctgttgctgg | gccttagatc | cagaggagag | gcccaagttt | 1860 |

```
cagcagctgg tacagtgcct aacagagttt catgcagccc tgggggccta cgtctgactc    1920
ctctccaatc ccacaccatc aggaagaagg tgcctgtcgg ggctcacttg aagcctgtca    1980
gggatgcttt gtatctaaca caacgccaac agaagcacat ttgtcttcca gaacaccgtg    2040
ccttagaaat gctttagaat ctgaactttt taagacagac ttaataatgt ggcatatttt    2100
ctagatatca cttttattag gttgaactga aagggttttt gtaaattttt tggccaaaat    2160 ttttaaaac atacttactt tggactaggg gtacattctt acaaaataaa taaacagttt     2220
ttaaaattgt ttagacacag atatttggaa ttagctatct tagtgccaac tgctttttat    2280
ttttttactt catcaaggtg atgtaagtga ctcaccttta aagttttttt agtgttattt    2340
tttatcacta ctctgggaaa tggtttgtct tcaagatgca atacttttct tagtaaagga    2400
aaaacagcat aaaagatac ctggtctgcc ttgtacaaga aaaggcaata ttagaggaag     2460
aaaatttaaa gaaagctag aggaaaaaaa aattttttta aaatactta ttagaagcaa      2520 actgcccttg catggaaaac tgtttatttt tttcagtgaa aaggaattct gctttcgtgt    2580
ttttgggaaa gcaggaactg agttcattac atctttaatt tggcagaaat tagcctttct    2640
gtgaaccaga tgtggtttgg ggcagatctg tagtaaacaa tggtgatttt atttatttt    2700 actctctgga aaaggagata atacaattcc agaaagtgaa ctcatatttc taaggttaag    2760 attcccttt attgcaccta gaatagtgct atgcacagag cgggtgcttg agttgttgtc    2820
gttttttgtt tgttttttaa atgtaaactg gtaaattttg tgcttatctt caaggctggc   2880
ttaagtataa aattgttttt taaacacttg aaaaattaaa ggatttgttt tatatt       2936
```

<210> SEQ ID NO 44
<211> LENGTH: 607
<212> TYPE: PRT
<213> ORGANISM: Homo sapiens

<400> SEQUENCE: 44

```
Met Arg Gly Ala Ala Arg Leu Gly Arg Pro Gly Arg Ser Cys Leu Pro
1               5                   10                  15

Gly Ala Arg Gly Leu Arg Ala Pro Pro Pro Pro Leu Leu Leu Leu
            20                  25                  30

Leu Ala Leu Leu Pro Leu Leu Pro Ala Pro Gly Ala Ala Ala Pro
        35                  40                  45

Ala Pro Arg Pro Pro Glu Leu Gln Ser Ala Ser Ala Gly Pro Ser Val
    50                  55                  60

Ser Leu Tyr Leu Ser Glu Asp Glu Val Arg Arg Leu Ile Gly Leu Asp
65                  70                  75                  80

Ala Glu Leu Tyr Tyr Val Arg Asn Asp Leu Ile Ser His Tyr Ala Leu
                85                  90                  95

Ser Phe Ser Leu Leu Val Pro Ser Glu Thr Asn Phe Leu His Phe Thr
            100                 105                 110

Trp His Ala Lys Ser Lys Val Glu Tyr Lys Leu Gly Phe Gln Val Asp
        115                 120                 125

Asn Val Leu Ala Met Asp Met Pro Gln Val Asn Ile Ser Val Gln Gly
    130                 135                 140

Glu Val Pro Arg Thr Leu Ser Val Phe Arg Val Glu Leu Ser Cys Thr
145                 150                 155                 160

Gly Lys Val Asp Ser Glu Val Met Ile Leu Met Gln Leu Asn Leu Thr
                165                 170                 175

Val Asn Ser Ser Lys Asn Phe Thr Val Leu Asn Phe Lys Arg Arg Lys
```

```
            180                 185                 190
Met Cys Tyr Lys Lys Leu Glu Glu Val Lys Thr Ser Ala Leu Asp Lys
            195                 200                 205

Asn Thr Ser Arg Thr Ile Tyr Asp Pro Val His Ala Ala Pro Thr Thr
            210                 215                 220

Ser Thr Arg Val Phe Tyr Ile Ser Val Gly Val Cys Cys Ala Val Ile
225                 230                 235                 240

Phe Leu Val Ala Ile Ile Leu Ala Val Leu His Leu His Ser Met Lys
                    245                 250                 255

Arg Ile Glu Leu Asp Asp Ser Ile Ser Ala Ser Ser Ser Ser Gln Gly
            260                 265                 270

Leu Ser Gln Pro Ser Thr Gln Thr Gln Tyr Leu Arg Ala Asp Thr
            275                 280                 285

Pro Asn Asn Ala Thr Pro Ile Thr Ser Tyr Pro Thr Leu Arg Ile Glu
            290                 295                 300

Lys Asn Asp Leu Arg Ser Val Thr Leu Leu Glu Ala Lys Gly Lys Val
305                 310                 315                 320

Lys Asp Ile Ala Ile Ser Arg Glu Arg Ile Thr Leu Lys Asp Val Leu
                    325                 330                 335

Gln Glu Gly Thr Phe Gly Arg Ile Phe His Gly Ile Leu Ile Asp Glu
                340                 345                 350

Lys Asp Pro Asn Lys Glu Lys Gln Ala Phe Val Lys Thr Val Lys Asp
            355                 360                 365

Gln Ala Ser Glu Ile Gln Val Thr Met Met Leu Thr Glu Ser Cys Lys
            370                 375                 380

Leu Arg Gly Leu His His Arg Asn Leu Leu Pro Ile Thr His Val Cys
385                 390                 395                 400

Ile Glu Glu Gly Glu Lys Pro Met Val Ile Leu Pro Tyr Met Asn Trp
                    405                 410                 415

Gly Asn Leu Lys Leu Phe Leu Arg Gln Cys Lys Leu Val Glu Ala Asn
                420                 425                 430

Asn Pro Gln Ala Ile Ser Gln Gln Asp Leu Val His Met Ala Ile Gln
            435                 440                 445

Ile Ala Cys Gly Met Ser Tyr Leu Ala Arg Arg Glu Val Ile His Lys
            450                 455                 460

Asp Leu Ala Ala Arg Asn Cys Val Ile Asp Asp Thr Leu Gln Val Lys
465                 470                 475                 480

Ile Thr Asp Asn Ala Leu Ser Arg Asp Leu Phe Pro Met Asp Tyr His
                    485                 490                 495

Cys Leu Gly Asp Asn Glu Asn Arg Pro Val Arg Trp Met Ala Leu Glu
                500                 505                 510

Ser Leu Val Asn Asn Glu Phe Ser Ser Ala Ser Asp Val Trp Ala Phe
            515                 520                 525

Gly Val Thr Leu Trp Glu Leu Met Thr Leu Gly Gln Thr Pro Tyr Val
            530                 535                 540

Asp Ile Asp Pro Phe Glu Met Ala Ala Tyr Leu Lys Asp Gly Tyr Arg
545                 550                 555                 560

Ile Ala Gln Pro Ile Asn Cys Pro Asp Glu Leu Phe Ala Val Met Ala
                    565                 570                 575

Cys Cys Trp Ala Leu Asp Pro Glu Glu Arg Pro Lys Phe Gln Gln Leu
                580                 585                 590

Val Gln Cys Leu Thr Glu Phe His Ala Ala Leu Gly Ala Tyr Val
            595                 600                 605
```

<210> SEQ ID NO 45
<211> LENGTH: 1398
<212> TYPE: DNA
<213> ORGANISM: Mus musculus

<400> SEQUENCE: 45

| | | | | | |
|---|---|---|---|---|---|
| atggaactgg | gcctgagctg | gatcttcctg | ctggccatcc | tgaagggcgt | gcagtgcgag | 60 |
| gtgcagctgt | tggagtctgg | gggaggcttg | gtacagcctg | gggggtccct | gagactctcc | 120 |
| tgtgcagcct | ctggattcac | ctttagcagc | tatgccatga | gctgggtccg | ccaggctcca | 180 |
| gggaaggggc | tggagtgggt | ctcactgatt | cataaggctg | gtcatactac | acagtacgca | 240 |
| gactccgtga | agggccggtt | caccatctcc | agagacaatt | ccaagaacac | gctgtatctg | 300 |
| caaatgaaca | gcctgagagc | cgaggacacg | gccgtatatt | actgtgcgaa | aggttatcgt | 360 |
| cattttgact | actggggcca | gggaaccctg | gtcaccgtct | ccagcgctag | caccaagggc | 420 |
| ccatcggtct | tccccctggc | accctcctcc | aagagcacct | ctgggggcac | agcggccctg | 480 |
| ggctgcctgg | tcaaggacta | cttccccgaa | ccggtgacgg | tgtcgtggaa | ctcaggcgcc | 540 |
| ctgaccagcg | gcgtgcacac | cttcccggct | gtcctacagt | cctcaggact | ctactccctc | 600 |
| agcagcgtgg | tgaccgtgcc | ctccagcagc | ttgggcaccc | agacctacat | ctgcaacgtg | 660 |
| aatcacaagc | ccagcaacac | caaggtggac | aagaaagttg | agcccaaatc | ttgtgacaaa | 720 |
| actcacacat | gcccaccgtg | cccagcacct | gaactcctgg | ggggaccgtc | agtcttcctc | 780 |
| ttccccccaa | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaagccgcgg | gaggagcagt | acaacagcac | gtaccgtgtg | 960 |
| gtcagcgtcc | tcaccgtcct | gcaccaggac | tggctgaatg | gcaaggagta | caagtgcaag | 1020 |
| gtctccaaca | aagccctccc | agcccccatc | gagaaaacca | tctccaaagc | caaagggcag | 1080 |
| ccccgagaac | cacaggtgta | caccctgccc | ccatcccggg | aggagatgac | caagaaccag | 1140 |
| gtcagcctga | cctgcctggt | caaaggcttc | tatcccagcg | acatcgccgt | ggagtgggag | 1200 |
| agcaatgggc | agccggagaa | caactacaag | accacgcctc | ccgtgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaatga | | | | | 1398 |

<210> SEQ ID NO 46
<211> LENGTH: 699
<212> TYPE: DNA
<213> ORGANISM: Mus musculus

<400> SEQUENCE: 46

| | | | | | |
|---|---|---|---|---|---|
| atgcgcgtgc | tgcccagct | gctgggcctg | ctcctgctgt | ggctgcccgg | cacccggtgc | 60 |
| gacatccaga | tgacccagtc | tccatcctcc | ctgtctgcat | ctgtaggaga | cagagtcgcc | 120 |
| atcacttgcc | gggcaagtca | gagcattagc | agctatttaa | attggtatca | gcagaaacca | 180 |
| gggaaagccc | ctaagctcct | gatctatcgg | gcatccaatt | tgcaaagtgg | ggtcccatca | 240 |
| aggttcagtg | gcagtggatc | tgggacagat | ttcactctca | ccatcagcag | tctgcaacct | 300 |
| gaagattttg | caacttacta | ctgtcaacag | gctgttggtt | ctcctcgtac | cttcggccaa | 360 |
| gggaccaagg | tggaaatcaa | acgaactgtg | gctgcaccat | ctgtcttcat | cttcccgcca | 420 |

-continued

```
tctgatgagc agttgaaatc tggaactgcc tctgttgtgt gcctgcttaa taacttctat    480
cccagggagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagcttgc ccgtcacaaa gagcttcaac aggggagag                           699
```